United States Patent
Ika et al.

(10) Patent No.: US 10,357,428 B2
(45) Date of Patent: Jul. 23, 2019

(54) MEDICATION ORGANIZER TRAY APPARATUS

(71) Applicant: RxAdvance Corporation, Southborough, MA (US)

(72) Inventors: Ravi V. Ika, Southborough, MA (US); Yogendra K. Jain, Wellesley, MA (US); Anand M. Tati, Westborough, MA (US); Paul Ducey, Sudbury, MA (US); James Lee, Acton, MA (US); Prakash Tallabattula, Northborough, MA (US); Kamal Patel, Framingham, MA (US); Satish Kumar Cheepurpalli, Westborough, MA (US)

(73) Assignee: RxAdvance Corporation, Southborough, MA (US)

( * ) Notice: Subject to any disclaimer, the term of this patent is extended or adjusted under 35 U.S.C. 154(b) by 37 days.

(21) Appl. No.: 15/641,221

(22) Filed: Jul. 4, 2017

(65) Prior Publication Data
US 2017/0296432 A1 Oct. 19, 2017

Related U.S. Application Data

(62) Division of application No. 14/555,560, filed on Nov. 26, 2014, now Pat. No. 9,757,305.

(51) Int. Cl.
*A61J 1/03* (2006.01)
*A61J 7/00* (2006.01)
*G06F 19/00* (2018.01)

(52) U.S. Cl.
CPC ................. *A61J 1/03* (2013.01); *A61J 1/035* (2013.01); *A61J 7/0069* (2013.01); *A61J 7/0084* (2013.01); *G06F 19/3462* (2013.01); *A61J 2200/30* (2013.01); *A61J 2205/10* (2013.01); *A61J 2205/30* (2013.01); *A61J 2205/60* (2013.01)

(58) Field of Classification Search
CPC .. A61J 1/03; A61J 1/035; A61J 7/0069; A61J 7/0084; A61J 2200/30; A61J 2205/10; A61J 2205/30; A61J 2205/60; G06F 19/3456; G06F 19/3462
USPC ...... 340/572.1, 572.8; 40/368; 156/69, 73.1; 206/459.1, 534; 705/2; 382/103
See application file for complete search history.

(56) References Cited

U.S. PATENT DOCUMENTS

2013/0195326 A1* 8/2013 Bear ................... G06F 19/3456
382/128

* cited by examiner

*Primary Examiner* — Andrew D Perreault
(74) *Attorney, Agent, or Firm* — Ashok Tankha

(57) ABSTRACT

A method and a medication organizer tray apparatus for organizing medications and collecting medication adherence information are provided. The medication organizer tray apparatus includes a support frame, multiple medication bins accommodating multiple medications, a bin cover layer with multiple customized bin labels, and a conductive circuit layer. The support frame includes multiple apertures positioned at predefined intervals from each other for placement of the medication bins. The customized bin labels having medical information printed thereon seal openings of the medication bins. The conductive circuit layer includes conductive lines running along one or more of a lower surface of the bin cover layer, around each medication bin, and a lower surface of each medication bin. The conductive circuit layer electrically communicates with a receptacle base to enable detection of removal of each medication bin from the support frame and detection of tampering of the medication bins.

30 Claims, 38 Drawing Sheets

| DOUG JORDAN | 85 HOLLY GROVE | | ABC PHARMACY | | DATE: 10/31/2001 |
|---|---|---|---|---|---|
| BIRTH 07/21/1967 | WILLIAMSBURG, VA 23185 (757)-123-4567 | | 123 FILL RIGHT PKWY | | FILE: ABC012345 |
| LOC: 12/15 | USE BY: 12/31/2011 | | SOUTHBOROUGH, MA 01172 | | |
| | | | (123)-456-7890 | | |

| NDC CODE | $R_x$ | DRUG NAME | FORM | DRUG DESCRIPTION | QTY | R | INSTRUCTIONS | PRESCRIBER | M | D | D | N |
|---|---|---|---|---|---|---|---|---|---|---|---|---|
| 00000 | 1234567 | TRAZODONE HCL 100 mg | TAB | | 30 | 5 | 1 TABLET EVERY NIGHT | DR. SMITH | | | | 1 |
| 11111 | 1523434 | SUBOXONE 2 mg-0.5 mg | TAB | | 30 | 5 | 1 TABLET AT NOON | DR. SMITH | | 1 | | |
| 22222 | 9876543 | CYMBALTA 60 mg | CAP | | 30 | 5 | 1 CAPSULE EVERY NIGHT | DR. ROBERTSON | | | | 1 |
| 33333 | 6789123 | NEXIUM 40 mg | CAP | | 30 | 5 | 1 CAPSULE EVERY MORNING | DR. ROBERTSON | 1 | | | |

| MORNING | MORNING | MORNING | MORNING | MORNING | MORNING | MORNING |
|---|---|---|---|---|---|---|
| ABC PHARMACY | ABC PHARMACY | ABC PHARMACY | ABC PHARMACY | ABC PHARMACY | ABC PHARMACY | ABC PHARMACY |
| DOUG JORDAN | DOUG JORDAN | DOUG JORDAN | DOUG JORDAN | DOUG JORDAN | DOUG JORDAN | DOUG JORDAN |
| #ABC012345 | #ABC012345 | #ABC012345 | #ABC012345 | #ABC012345 | #ABC012345 | #ABC012345 |
| 1-NEXIUM 40mg | 1-NEXIUM 40mg | 1-NEXIUM 40mg | 1-NEXIUM 40mg | 1-NEXIUM 40mg | 1-NEXIUM 40mg | 1-NEXIUM 40mg |
| 1-LISENOPRIL 10mg | 1-LISENOPRIL 10mg | 1-LISENOPRIL 10mg | 1-LISENOPRIL 10mg | 1-LISENOPRIL 10mg | 1-LISENOPRIL 10mg | 1-LISENOPRIL 10mg |
| 1-ASPIRIN 250mg | 1-ASPIRIN 250mg | 1-ASPIRIN 250mg | 1-ASPIRIN 250mg | 1-ASPIRIN 250mg | 1-ASPIRIN 250mg | 1-ASPIRIN 250mg |
| DAY | DAY | DAY | DAY | DAY | DAY | DAY |
| ABC PHARMACY | ABC PHARMACY | ABC PHARMACY | ABC PHARMACY | ABC PHARMACY | ABC PHARMACY | ABC PHARMACY |
| DOUG JORDAN | DOUG JORDAN | DOUG JORDAN | DOUG JORDAN | DOUG JORDAN | DOUG JORDAN | DOUG JORDAN |
| #ABC012345 | #ABC012345 | #ABC012345 | #ABC012345 | #ABC012345 | #ABC012345 | #ABC012345 |
| 1-SUBOXONE 2mg-0.5mg | 1-SUBOXONE 2mg-0.5mg | 1-SUBOXONE 2mg-0.5mg | 1-SUBOXONE 2mg-0.5mg | 1-SUBOXONE 2mg-0.5mg | 1-SUBOXONE 2mg-0.5mg | 1-SUBOXONE 2mg-0.5mg |
| NIGHT | NIGHT | NIGHT | NIGHT | NIGHT | NIGHT | NIGHT |
| ABC PHARMACY | ABC PHARMACY | ABC PHARMACY | ABC PHARMACY | ABC PHARMACY | ABC PHARMACY | ABC PHARMACY |
| DOUG JORDAN | DOUG JORDAN | DOUG JORDAN | DOUG JORDAN | DOUG JORDAN | DOUG JORDAN | DOUG JORDAN |
| #ABC012345 | #ABC012345 | #ABC012345 | #ABC012345 | #ABC012345 | #ABC012345 | #ABC012345 |
| 1-TRANZODONE 100mg | 1-TRANZODONE 100mg | 1-TRANZODONE 100mg | 1-TRANZODONE 100mg | 1-TRANZODONE 100mg | 1-TRANZODONE 100mg | 1-TRANZODONE 100mg |

| SUSAN SMITH<br>SUN<br>MORN<br>06/01/14 | SUSAN SMITH<br>MON<br>MORN<br>06/02/14 | SUSAN SMITH<br>TUE<br>MORN<br>06/03/14 | SUSAN SMITH<br>WED<br>MORN<br>06/04/14 | SUSAN SMITH<br>THU<br>MORN<br>06/05/14 | SUSAN SMITH<br>FRI<br>MORN<br>06/06/14 | SUSAN SMITH<br>SAT<br>MORN<br>06/07/14 |
|---|---|---|---|---|---|---|
| 1 MECLIZINE HCL 20mg<br>1 GABAPENTIN 2mg | 1 MECLIZINE HCL 20mg<br>1 GABAPENTIN 2mg | 1 MECLIZINE HCL 20mg<br>1 GABAPENTIN 2mg | 1 MECLIZINE HCL 20mg<br>1 GABAPENTIN 2mg | 1 MECLIZINE HCL 20mg<br>1 GABAPENTIN 2mg | 1 MECLIZINE HCL 20mg<br>1 GABAPENTIN 2mg | 1 MECLIZINE HCL 20mg<br>1 GABAPENTIN 2mg |
| SUSAN SMITH<br>SUN<br>DAY<br>06/01/14 | SUSAN SMITH<br>MON<br>DAY<br>06/02/14 | SUSAN SMITH<br>TUE<br>DAY<br>06/03/14 | SUSAN SMITH<br>WED<br>DAY<br>06/04/14 | SUSAN SMITH<br>THU<br>DAY<br>06/05/14 | SUSAN SMITH<br>FRI<br>DAY<br>06/06/14 | SUSAN SMITH<br>SAT<br>DAY<br>06/07/14 |
| 1 MECLIZINE HCL 20mg<br>1 GABAPENTIN 2mg | 1 MECLIZINE HCL 20mg<br>1 GABAPENTIN 2mg | 1 MECLIZINE HCL 20mg<br>1 GABAPENTIN 2mg | 1 MECLIZINE HCL 20mg<br>1 GABAPENTIN 2mg | 1 MECLIZINE HCL 20mg<br>1 GABAPENTIN 2mg | 1 MECLIZINE HCL 20mg<br>1 GABAPENTIN 2mg | 1 MECLIZINE HCL 20mg<br>1 GABAPENTIN 2mg |
| SUSAN SMITH<br>SUN<br>NIGHT<br>06/01/14 | SUSAN SMITH<br>MON<br>NIGHT<br>06/02/14 | SUSAN SMITH<br>TUE<br>NIGHT<br>06/03/14 | SUSAN SMITH<br>WED<br>NIGHT<br>06/04/14 | SUSAN SMITH<br>THU<br>NIGHT<br>06/05/14 | SUSAN SMITH<br>FRI<br>NIGHT<br>06/06/14 | SUSAN SMITH<br>SAT<br>NIGHT<br>06/07/14 |
| 1 MECLIZINE HCL 20mg<br>1 GABAPENTIN 2mg | 1 MECLIZINE HCL 20mg<br>1 GABAPENTIN 2mg | 1 MECLIZINE HCL 20mg<br>1 GABAPENTIN 2mg | 1 MECLIZINE HCL 20mg<br>1 GABAPENTIN 2mg | 1 MECLIZINE HCL 20mg<br>1 GABAPENTIN 2mg | 1 MECLIZINE HCL 20mg<br>1 GABAPENTIN 2mg | 1 MECLIZINE HCL 20mg<br>1 GABAPENTIN 2mg |

| SUSAN SMITH<br>DOB 8/6/1949<br>12 ALBIN ST<br>SPRINGFIELD, MA 01778 | NDC | Rx | DRUG NAME | DOSE SIZE | DRUG DESC. | INSTRUCTIONS | CALL YOUR DOCTOR<br>FOR MEDICAL ADVICE<br>ABOUT SIDE EFFECTS.<br>CONTACT THE FDA AT 1-800-FDA-1088 |
|---|---|---|---|---|---|---|---|
| | 67-840 | 1585424 | QUINAPRIL | 20 mg | ROUND BROWN TABLET | 1 TABLET EVERY MORNING | |
| | 69-034 | 4564315 | GABAPENTIN | 20mg | WHITE TABLET | 1 TABLET NIGHT | |
| USE BY 6/6/14<br>DPT ID: KB19734672 | 56-32 | 3664215 | MECLIZINE HCL | 20mg | ROUND RED TABLET | 1 TABLET EVERY NIGHT | |

FIG. 14C

| SUSAN SMITH SUN MORN 06/01/14 | SUSAN SMITH MON MORN 06/02/14 | SUSAN SMITH TUE MORN 06/03/14 | SUSAN SMITH WED MORN 06/04/14 | SUSAN SMITH THU MORN 06/05/14 | SUSAN SMITH FRI MORN 06/06/14 | SUSAN SMITH SAT MORN 06/07/14 |
|---|---|---|---|---|---|---|
| 1 MECLIZINE HCL 25mg 1 GABAPENTIN 300mg | 1 MECLIZINE HCL 25mg 1 GABAPENTIN 300mg | 1 MECLIZINE HCL 25mg 1 GABAPENTIN 300mg | 1 MECLIZINE HCL 25mg 1 GABAPENTIN 300mg | 1 MECLIZINE HCL 25mg 1 GABAPENTIN 300mg | 1 MECLIZINE HCL 25mg 1 GABAPENTIN 300mg | 1 MECLIZINE HCL 25mg 1 GABAPENTIN 300mg |
| SUSAN SMITH SUN DAY 06/01/14 | SUSAN SMITH MON DAY 06/02/14 | SUSAN SMITH TUE DAY 06/03/14 | SUSAN SMITH WED DAY 06/04/14 | SUSAN SMITH THU DAY 06/05/14 | SUSAN SMITH FRI DAY 06/06/14 | SUSAN SMITH SAT DAY 06/07/14 |
| 1 FUROSEMIDE 40mg 1 QUINAPRIL 20mg | 1 FUROSEMIDE 40mg 1 QUINAPRIL 20mg | 1 FUROSEMIDE 40mg 1 QUINAPRIL 20mg | 1 FUROSEMIDE 40mg 1 QUINAPRIL 20mg | 1 FUROSEMIDE 40mg 1 QUINAPRIL 20mg | 1 FUROSEMIDE 40mg 1 QUINAPRIL 20mg | 1 FUROSEMIDE 40mg 1 QUINAPRIL 20mg |
| SUSAN SMITH SUN NIGHT 06/01/14 | SUSAN SMITH MON NIGHT 06/02/14 | SUSAN SMITH TUE NIGHT 06/03/14 | SUSAN SMITH WED NIGHT 06/04/14 | SUSAN SMITH THU NIGHT 06/05/14 | SUSAN SMITH FRI NIGHT 06/06/14 | SUSAN SMITH SAT NIGHT 06/07/14 |
| 1 MECLIZINE HCL 25mg 1 GABAPENTIN 300mg | 1 MECLIZINE HCL 25mg 1 GABAPENTIN 300mg | 1 MECLIZINE HCL 25mg 1 GABAPENTIN 300mg | 1 MECLIZINE HCL 25mg 1 GABAPENTIN 300mg | 1 MECLIZINE HCL 25mg 1 GABAPENTIN 300mg | 1 MECLIZINE HCL 25mg 1 GABAPENTIN 300mg | 1 MECLIZINE HCL 25mg 1 GABAPENTIN 300mg |

| SUSAN SMITH DOB 8/6/1949 12 ALBIN ST SPRINGFIELD, MA 01778 | NDC | Rx | DRUG NAME | DOSE SIZE | DRUG DESC. | INSTRUCTIONS | CALL YOUR DOCTOR FOR MEDICAL ADVICE ABOUT SIDE EFFECTS TO THE FDA AT 1-800-FDA-1088 |
|---|---|---|---|---|---|---|---|
| | 67-840 | 1585424 | QUINAPRIL | 20 mg | ROUND BROWN TABLET | 1 TABLET EVERY MORNING | |
| | 69-034 | 4564315 | GABAPENTIN | 20 mg | ROUND BROWN TABLET | 1 TABLET NIGHT | |
| USE BY 6/6/14 DPT ID: KB19734672 | 565-32 | 3664215 | MECLIZINE HCL | 20 mg | ROUND BROWN TABLET | 1 TABLET EVERY MORNING | |

FIG. 14D

| DRUG | COMPLIANCE URGENCY | DURATION | DOSAGE | FRONT IMAGE | BACK IMAGE |
|---|---|---|---|---|---|
| NEXIUM 40 mg | CRITICAL | 04/08/2009 – 04/07/2010 | TAKE ONE CAPSULE EVERY MORNING | | |
| LIPITOR 10 mg | CRITICAL | 04/08/2009 – 04/07/2010 | TAKE ONE TABLET EVERY MORNING | | |
| LISINOPRIL 20 mg | CRITICAL | 04/08/2009 – 04/07/2010 | TAKE ONE TABLET EVERY MORNING | | |

FIG. 26

MEDICATION ORGANIZER TRAY APPARATUS

CROSS-REFERENCES TO RELATED APPLICATIONS

This application is a divisional of non-provisional patent application Ser. No. 14/555,560 titled "Medication Organizer Tray Apparatus", filed on Nov. 26, 2014 in the United States Patent and Trademark Office.

The specification of the above referenced application is incorporated herein by reference in its entirety.

BACKGROUND

Poor compliance with a healthcare provider or physician-prescribed medication regimen is a significant cause of disease-related morbidity and mortality. Poor medication adherence is estimated to cause about 125.000 deaths and about 33% to about 69% of medication-related hospital admissions annually. The aggregate cost of hospital admissions related to medication non-adherence alone is estimated to be about $100 billion per year and medication non-adherence accounts for about 10% of overall hospital admissions. Currently, about 50% of prescribed medications are not taken as directed. Noncompliance with prescribed medications leads to a deterioration of the medical condition, hospitalization, and irreversible loss of function, resulting in significant human and financial costs. A growing problem, both among young people and the elderly, is overuse or abuse of certain medications, for example, pain relievers and tranquilizers. Among the elderly, about 90% of healthcare recipients make medication errors, resulting in about 40% of hospital admissions for this growing segment of the American population. Cognition also generally declines with age. Consequently, elderly healthcare recipients may experience difficulty in acquiring, organizing, and remembering to take their medications as prescribed.

Many healthcare recipients with chronic conditions, for example, elderly patients on multiple medications have difficulty adhering to prescribed therapies. Such healthcare recipients typically consume about 2 medications to about 20 medications per day. In general, when more medications have to be taken and the more times each day the healthcare recipient must use various therapies, the more likely is the probability of medication errors. Often, healthcare recipients have co-morbid conditions that interfere with their adherence to medication regimens. These conditions may include, for example, diabetes and associated complications such as blindness or a lack of mobility, various neurological conditions and dementia, arthritis and associated difficulties in manipulating devices, and other debilitating conditions. In addition to pills, healthcare recipients take other medications, for example, parenterals such as injections, inhalers, eye drops, etc., and adherence to these medications is also very low. At times, healthcare recipients do not have access to transportation or a caregiver to collect their medications. Moreover, many medications are sensitive to certain environmental conditions, for example, heat, humidity, light, or cold. Over-exposure to these environmental conditions can reduce the potency or efficacy of the medications.

The New England Healthcare Institute (NEHI) estimates that eliminating prescription non-adherence can save $290 billion annually by avoiding additional visits to a doctor, emergency room (ER) visits, hospital admissions, and additional medications. Studies have shown a total annual per capita savings of about $7,823 for congestive heart failure, about $3,908 for hypertension, about $3,757 for diabetes, and about $1,259 for dyslipidemia in adherent healthcare recipients. To improve adherence, healthcare recipients need easy access to all of their medications on a regular basis and not have to handle multiple pill bottles which expire at different times, and need to go to a pharmacy as few times as possible for their medications or refills. Various previously proposed devices for testing compliance of healthcare recipients with prescribed medication regimens are unsatisfactory in that they are relatively cumbersome, not accurate, and do not adequately cover the extended time spans for which many prescribed dosing regimens must be maintained. Hence, there is a need for an improved device, for example, a pre-filled medication tray that accurately and conveniently packages individual doses of medication, in various forms such as a liquid form or a tablet form, which are more easily manageable in a safe and convenient manner, can be easily dispatched to the healthcare recipients, and which measures the compliance of healthcare recipients with physician-prescribed medication regimens.

Although a pre-filled medication tray ensures that the right medications are loaded and that a healthcare recipient has easy access to the medications, many healthcare recipients are still non-adherent. For example, when a healthcare recipient travels or is out for a day or is on vacation, the healthcare recipient may forget to carry his/her pre-filled medication trays. Moreover, a health plan, pharmacy benefit manager (PBM), or an at risk hospital system requires healthcare recipient adherent information on a dose by dose basis, and not only on a monthly basis. Furthermore, there is a potential of tampering with the pre-filled medication tray when the pre-filled medication tray contains high priced medications and opioids. High priced and/or abusable medications, for example, pain killers, opioids, etc., are typically securely packaged in the pre-filled medication tray to preclude tampering and removal of the high priced and/or abusable medications from the pre-filled medication tray. However, these medications can be removed from the pre-filled medication tray by creating an incision or a cut on front surfaces, rear surfaces, side surfaces, and/or undersides of containers in the pre-filled medication tray.

Hence, there is a long felt but unresolved need for a secure, enhanced pre-filled medication organizer tray apparatus that increases adherence to medications with minimal cost and support by efficiently organizing the medications, providing medical information associated with the medications, providing enhanced access to the medications, continuously monitoring medication adherence by a healthcare recipient, and transmitting alerts to healthcare providers and the healthcare recipient for reducing hospitalizations, readmissions, emergency room (ER) visits, home health visits, nurse support, etc. Furthermore, there is a need for a pre-filled medication organizer tray apparatus that can be easily dispatched to healthcare recipients, and that detects tampering, theft, or abuse of high priced medications and opioids.

SUMMARY OF THE INVENTION

This summary is provided to introduce a selection of concepts in a simplified form that are further disclosed in the detailed description of the invention. This summary is not intended to identify key or essential inventive concepts of the claimed subject matter, nor is it intended for determining the scope of the claimed subject matter.

The medication organizer tray apparatus disclosed herein address the above stated need for increasing adherence to medications with minimal cost and support by efficiently organizing the medications, providing medical information associated with the medications, providing enhanced access to the medications, continuously monitoring medication adherence by a healthcare recipient, and transmitting alerts to healthcare providers and the healthcare recipient for reducing hospitalizations, readmissions, emergency room (ER) visits, home health visits, nurse support, etc. Furthermore the medication organizer tray apparatus disclosed herein detects tampering, theft, or abuse of high priced medications and opioids. Furthermore, the medication organizer tray apparatus disclosed herein can be easily dispatched to healthcare recipients. The medication organizer tray apparatus disclosed herein comprises a support frame, multiple medication bins, a bin cover layer, and a conductive circuit layer. The support frame comprises multiple apertures positioned at predefined intervals from each other. The medication bins are adapted for placement in the apertures of the support frame. The medication bins accommodate multiple medications. The medication bins are configured to be removed from the support frame. The bin cover layer is removably attached to an upper surface of the support frame. The bin cover layer comprises multiple customized bin labels removably configured therewithin. The customized bin labels comprise medical information printed thereon and are configured to seal openings of the medication bins. The conductive circuit layer comprises multiple conductive lines running along one or more of a lower surface of the bin cover layer, around each medication bin, and a lower surface of each medication bin. The conductive circuit layer electrically communicates with a receptacle base to enable detection of removal of each medication bin from the support frame and detection of tampering of the medication bins, by detecting a break in the conductive lines of the conductive circuit layer.

In one or more embodiments, related systems include but are not limited to circuitry and/or programming for effecting the methods referenced herein; the circuitry and/or programming can be any combination of hardware, software, and/or firmware configured to effect the herein-referenced methods depending upon the design choices of a system designer. Also, various structural elements may be employed depending on the design choices of the system designer.

BRIEF DESCRIPTION OF THE DRAWINGS

The foregoing summary, as well as the following detailed description of the invention, is better understood when read in conjunction with the appended drawings. For the purpose of illustrating the invention, exemplary constructions of the invention are shown in the drawings. However, the invention is not limited to the specific methods and structures disclosed herein. The description of a method step or a structure referenced by a numeral in a drawing carries over to the description of that method step or structure shown by that same numeral in any subsequent drawing herein.

FIGS. 14A-14D exemplarily illustrate top plan views of different embodiments of a bin cover layer of the medication organizer tray apparatus, showing customized bin labels removably configured within the bin cover layer.

FIG. 26 exemplarily illustrates a screenshot of an image of the medication organizer tray apparatus filled with medications, displayed on a graphical user interface provided by a pill station manager application on a user device.

DETAILED DESCRIPTION OF THE INVENTION

Figure 1A:
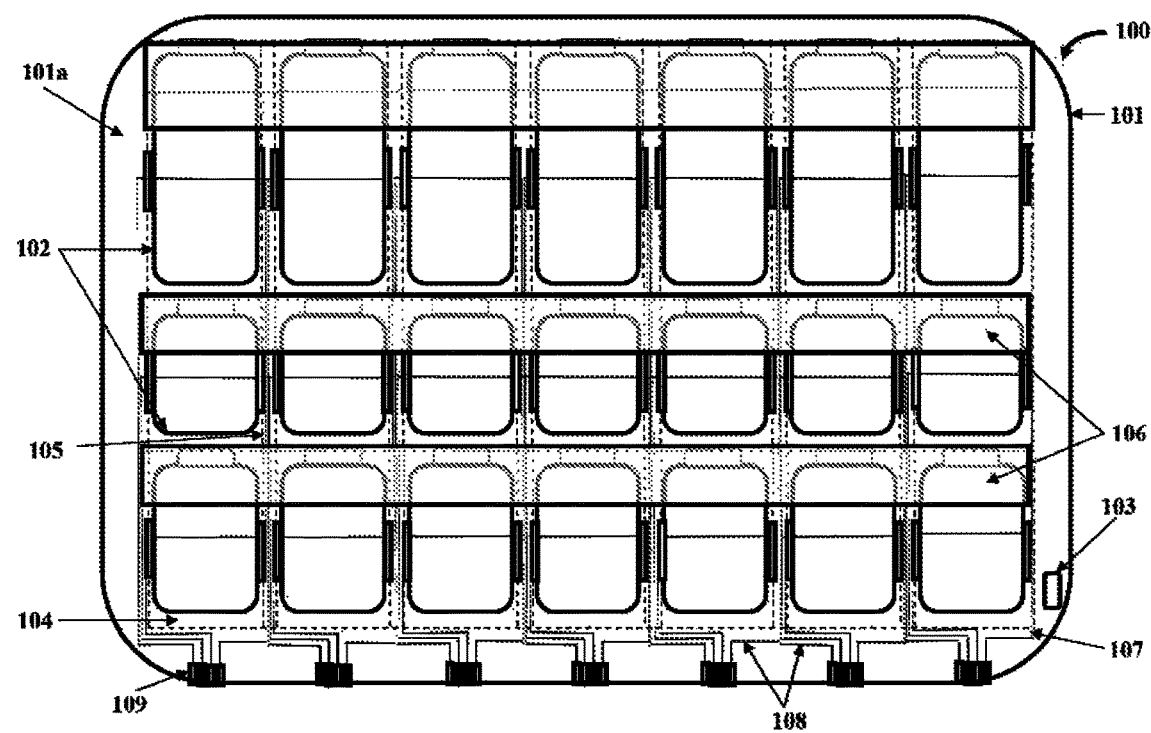
FIG. 1A exemplarily illustrates a top plan view of a medication organizer tray apparatus for organizing medications.
Figure 1B:
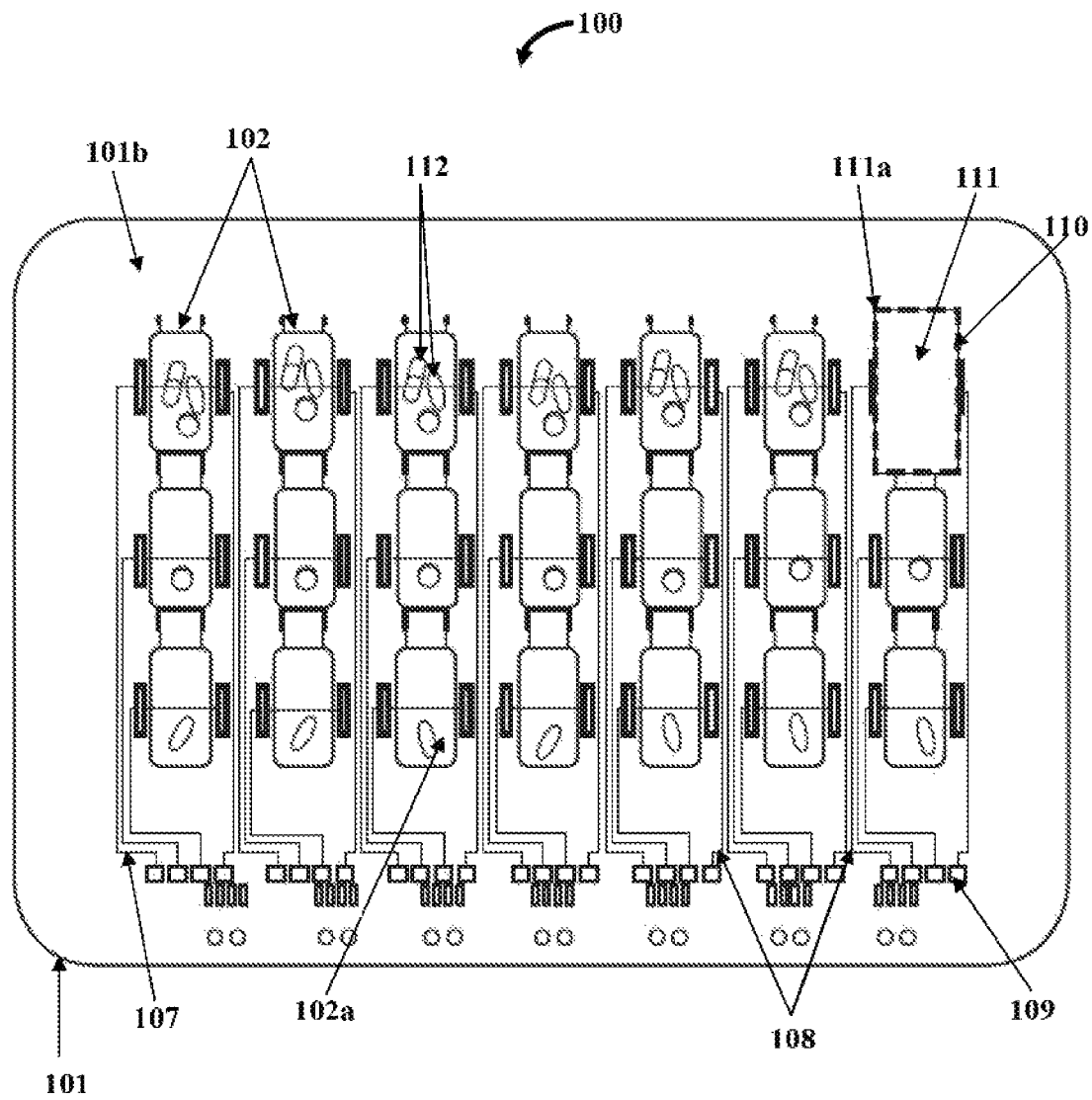
FIG. 1B exemplarily illustrates a bottom view of the medication organizer tray apparatus for organizing medications.
Figure 1C:
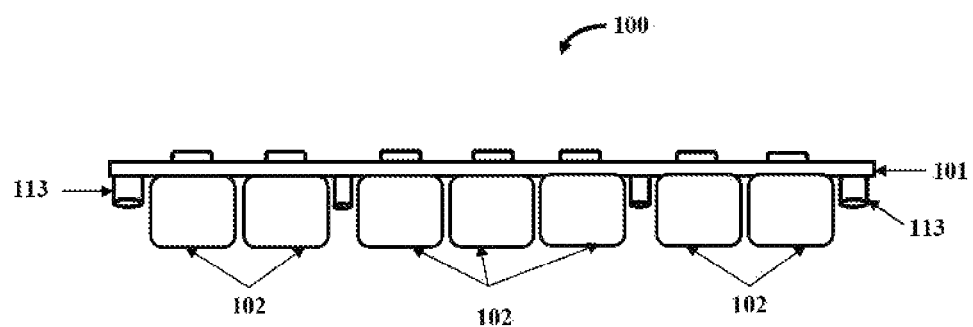
FIG. 1C exemplarily illustrates a front elevation view of the medication organizer tray apparatus.

FIGS. 1A-1C exemplarily illustrate different views of a medication organizer tray apparatus 100 for organizing medications 112 exemplarily illustrated in FIG. 1B. The medication organizer tray apparatus 100 disclosed herein is a medication tray, for example, a thermoform based pill tray or a thermoform plastic tray with sensitive circuitry that electronically alerts healthcare providers on whether medication bins 102 comprising medications 112 are opened correctly and at the right time. As used herein, "healthcare provider" refers to a person or an entity, for example, a medical practitioner, a medical specialist, a health specialist, a physician, a doctor, a dentist, a surgeon, a nurse, a therapist, a nutritionist, a pharmacist, a clinical trial professional, a clinical study professional, a healthcare institution such as a hospital, a clinic, etc., a health insurance company, a health maintenance organization, a caregiver, etc., that provides healthcare services, for example, medical treatment, dental treatment, medications 112, health insurance, etc. to a healthcare recipient. As used herein, "healthcare recipient" refers to a person or an entity, for example, a patient who receives healthcare services from a healthcare provider.

The medication organizer tray apparatus 100 disclosed herein supports a polymer filling and facilitates intact shipping of the medication organizer tray apparatus 100, and handling of the medication organizer tray apparatus 100 by healthcare recipients, for example, elderly and sick patients. The medication organizer tray apparatus 100 disclosed herein can be used by healthcare recipients of all ages and can be shipped to healthcare recipients at any location, for example, a home location, an office location, assisted living facilities, nursing homes, etc. The medication organizer tray apparatus 100 provides accurate medications 112 based on prescriptions and provides guaranteed medications 112 to healthcare recipients with medication synchronization and without the need for transportation. The medication organizer tray apparatus 100 eliminates the need for a healthcare recipient such as a patient or healthcare provider such as a caregiver to manually fill the medication organizer tray apparatus 100.

FIG. 1A exemplarily illustrates a top plan view of the medication organizer tray apparatus 100 for organizing medications 112. The medication organizer tray apparatus 100 disclosed herein comprises a support frame 101, multiple medication bins 102, a bin cover layer 104, and a conductive circuit layer 107. The support frame 101 comprises apertures 111 configured as wells positioned at predefined intervals from each other. FIG. 1B exemplarily illustrates an aperture 111 of the support frame 101 after removal of a medication bin 102 from the support frame 101. The medication bins 102 accommodate multiple medications 112 as exemplarily illustrated in FIG. 1B. The bin cover layer 104 is removably attached to an upper surface 101a of the support frame 101. The bin cover layer 104 comprises multiple customized bin labels 106 removably configured within the bin cover layer 104. The customized bin labels 106 are configured to seal openings 117 of the medication bins 102 exemplarily illustrated in FIG. 7 and FIG. 10. The bin cover layer 104 comprises perforations 105 positioned at predefined areas on the bin cover layer 104 as exemplarily illustrated in FIG. 1A, to match perforations 110 positioned proximal to outer edges 111a of the apertures 111 of the support frame 101 as exemplarily illustrated in FIG. 1B. In an embodiment, electrically conductive material, for example, conductive ink is applied on the perforations 105, 110, etc., of the medication organizer tray apparatus 100 exemplarily illustrated in FIGS. 1A-1B, for ensuring continuity around the perforations 105, 110, etc., and connectivity with conductive lines 108 of the conductive circuit layer 107 around the perforations 105, 110, etc. The conductive circuit layer 107 comprises multiple conductive lines 108 running along one or more of a lower surface 104b of the bin cover layer 104 as exemplarily illustrated in FIG. 18A, around each medication bin 102, and a lower surface 102a of each medication bin 102.

The medication organizer tray apparatus 100 disclosed herein further comprises an electronic identification component 103 embedded into the support frame 101 as exemplarily illustrated in FIG. 1A. The electronic identification component 103 is configured to electrically communicate with a receptacle base 2101 exemplarily illustrated in FIGS. 21A-21B and FIG. 22. The electronic identification component 103 is further configured to identify the medication organizer tray apparatus 100, and store and exchange medication adherence information with the receptacle base 2101 as disclosed in the detailed description of FIGS. 17A-17B.

FIG. 1B exemplarily illustrates a bottom view of the medication organizer tray apparatus 100 for organizing medications 112. The medication bins 102 are adapted for placement in the apertures 111 of the support frame 101. The medication bins 102 are configured in one of multiple sizes and shapes for accommodating medications 112 of different types as exemplarily illustrated in FIGS. 2A-2B, FIG. 6, and FIG. 14A. In an embodiment, each medication bin 102 is configured as a removable cup or a cup well containing medications 112, for example, sufficient for a day's use, and is easy to use. The medication bin 102 is, for example, made of plastic. The medications 112 comprise, for example, oral medications, parenterals, blister packed medications, individual doses of medications, pills, etc., or any combinations thereof. The parenterals comprise, for example, injections, insulin vials, syringes, inhalers, eye drops, etc. The blister packed medications have individual or multiple doses of medications 112 contained in a form of plastic packaging. In an embodiment, the medication bins 102 that accommodate oral medications 112 are of a standard size. As exemplarily illustrated in FIG. 1B, a lower surface 102a of each medication bin 102 is transparent to create a clear optical surface for facilitating imaging of the medications 112 accommodated in each medication bin 102 in the medication organizer tray apparatus 100, for example, by a camera embedded in the receptacle base 2101 exemplarily illustrated in FIGS. 21A-21B and FIG. 22, or in a medication dispensing system 2401 exemplarily illustrated in FIG. 24.

In an embodiment, the medication bins 102 are configured to be removed from the support frame 101. When the medication bins 102 are removed from the support frame 101, the medications 112 accommodated in the medication bins 102 are removed along with the medication bins 102. Healthcare recipients can remove the medication bins 102 from the support frame 101 and take medications 112 prescribed for a day from the medication bins 102. When the medication bins 102 are removed from the support frame 101, the customized bin labels 106 positioned on the medication bins 102 exemplarily illustrated in FIG. 1A, remain in contact with the medication bins 102 and are removed along with the medication bins 102 to maintain structural integrity of the medication organizer tray apparatus 100. In another embodiment, the medication bins 102 are retained in the support frame 101, and the customized bin labels 106 that seal the medication bins 102 can be removed to access the medications 112 in the medication bins 102.

Multiple conductive lines 108 and conductive pads 109 of the conductive circuit layer 107 of the medication organizer tray apparatus 100 are exemplarily illustrated in FIGS. 1A-1B. The conductive circuit layer 107 electrically communicates with the receptacle base 2101 to enable detection of removal of each medication bin 102 from the support frame 101 and detection of tampering of the medication bins 102. The conductive lines 108 of the conductive circuit layer 107 are configured in a multi-layer conductive circuit that trips when one or more medication bins 102 are removed from the support frame 101.

In an embodiment, the medication organizer tray apparatus 100 is free from the support frame 101, and is configured, for example, with a thermoform bottom. The medication organizer tray apparatus 100 is configured using existing prefilled medication trays, for example, with a thermoform design, plastic pill trays, or other types of medication trays of different shapes and sizes. In this embodiment, the bin cover layer 104 with the customized bin labels 106 and the conductive circuit layer 107 are built as a single unit and placed, pasted, and affixed onto the existing prefilled medication tray.

FIG. 1C exemplarily illustrates a front elevation view of the medication organizer tray apparatus 100. In an embodiment, the support frame 101 of the medication organizer tray apparatus 100 comprises one or more depressed button heads 113, for example, thermoform buttons based on the size of the medication organizer tray apparatus 100. The depressed button heads 113 attach the medication organizer tray apparatus 100 to the receptacle base 2101 exemplarily illustrated in FIGS. 21A-21B and FIG. 22.

Figure 2A:
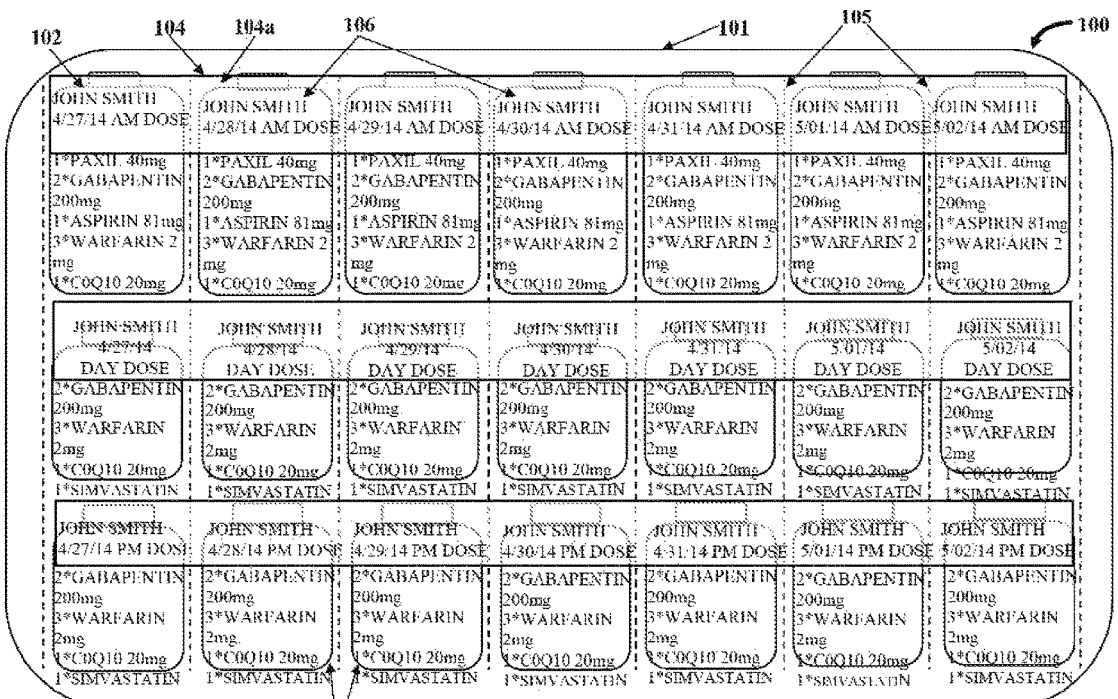
FIGS. 2A-2B exemplarily illustrate top plan views of different embodiments of the medication organizer tray apparatus for organizing medications.
Figure 2B:

FIGS. 2A-2B exemplarily illustrate top plan views of different embodiments of the medication organizer tray apparatus 100 for organizing medications 112 exemplarily illustrated in FIG. 1B. The medication organizer tray apparatus 100 comprises medication bins 102 of different sizes as exemplarily illustrated in FIGS. 2A-2B. As exemplarily illustrated in FIGS. 2A-2B, the first row of medication bins 102 is of a large size, while the second and third rows of medication bins 102 are of a smaller size than the first row. The customized bin labels 106 of the bin cover layer 104 are customized adhesive backed printouts comprising medical information printed thereon as exemplarily illustrated in FIGS. 2A-2B. The medical information printed on the customized bin labels 106 comprises, for example, one or more of a list of medications 112 in each medication bin 102, dosage information, color coding of dosage times, a time of day for administering the medications 112, drug names, directions to follow, name of a prescriber, date of preparation, description of contents of each medication bin 102, a personalized website link configured to link to a secure online interface comprising healthcare recipient information, a healthcare recipient identifier, etc. The medical information is printed on the customized bin labels 106 at a refill location and is configured to meet, for example, the United States Pharmacopeia (USP) standards. In an embodiment, the customized bin labels 106 comprise an updated medication list with images of the medications 112 inside each medication bin 102. FIGS. 2A-2B also show the perforations 105 of the bin cover layer 104.

Figure 3:
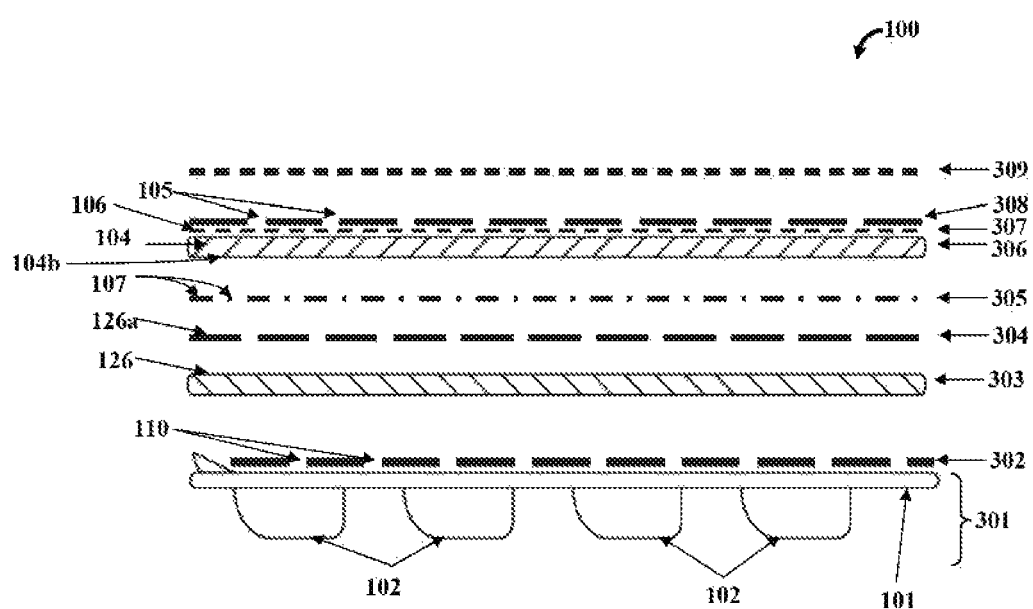
FIG. 3 exemplarily illustrates different component layers of the medication organizer tray apparatus.

FIG. 3 exemplarily illustrates different component layers 301 to 309 of the medication organizer tray apparatus 100. As exemplarily illustrated in FIG. 3, the medication organizer tray apparatus 100 comprises nine component layers 301 to 309. The first component layer 301 comprises the support frame 101, for example, a thermoform tray with apertures 111 exemplarily illustrated in FIG. 1B, and medication bins 102 placed in the apertures 111 of the support frame 101. The medication bins 102 hold the medications 112 as exemplarily illustrated in FIG. 1B and as disclosed in the detailed description of FIG. 1B. The second component layer 302 is a perforated layer comprising perforations 110 of the support frame 101. The perforations 110 of the support frame 101 are positioned proximal to the outer edges 111a of the apertures 111 of the support frame 101 exemplarily illustrated in FIG. 1B, to facilitate removal of the medication bins 102 from the support frame 101. The third component layer 303 is an adhesive protective paper layer 126 exemplarily illustrated in FIGS. 18A-18B and disclosed in the detailed description of FIGS. 18A-18B. The fourth component layer 304 represents a selectively applied adhesive 126a of the adhesive protective paper layer 126 configured to match the surface 101d exemplarily illustrated in FIG. 18B, surrounding the outer edges 11a of the apertures 111 of the support frame 101 and a lip 121 of each medication bin 102 exemplarily illustrated in FIG. 10 and FIGS. 12-13. The fifth component layer 305 is the conductive circuit layer 107 comprising etched circuitry that electrically communicates with the receptacle base 2101 exemplarily illustrated in FIGS. 21A-21B and FIG. 22 and disclosed in the detailed description of FIGS. 21A-21B and FIG. 22, for enabling detection of a break in continuity of the conductive lines 108 exemplarily illustrated in FIGS. 1A-1B, when the medication bins 102 are removed from the support frame 101 of the medication organizer tray apparatus 100.

The sixth component layer 306 is the bin cover layer 104. The bin cover layer 104 is, for example, a paper layer or a cardboard stock layer of thick stock. In an embodiment, the bin cover layer 104 is composed of a coated paper that allows conductive ink or other conductive circuitry applications to be registered in fine line thickness thereon. In another embodiment, the sixth component layer 306 comprises additional information printed thereon for the healthcare recipients. In this embodiment, the additional information is viewable in and/or around the conductive circuit layer 107. When a healthcare recipient removes the medication bin 102 from the support frame 101 and then peels the customized bin label 106 of the bin cover layer 104 exemplarily illustrated in FIGS. 2A-2B, to access the medications 112, a bottom surface 106b of each customized bin label 106 exemplarily illustrated in FIG. 11A, displays the additional information printed thereon. This additional information comprises, for example, wellness information, reminders, incentives for medication adherence such as award points, lottery tickets, gaming information, or bingo numbers, quotes such as motivational and religious quotes or a quote of the day, pictures of family members, etc. In an embodiment, a bingo card or another game card can be supplied to a healthcare recipient, and as the healthcare recipient takes his/her medications 112 and fills the bingo card, he/she can win prizes. A healthcare recipient can read the additional information printed on the bottom surface of the peeled customized bin label 106 when he or she removes and opens the medication bins 102. There is minimal to no bleeding of Food and Drug Administration (FDA) approved food grade ink printing on the lower surface 104b of the bin cover layer 104. The bin cover layer 104 allows etching of complex circuits on the lower surface 104b of the bin cover layer 104 without short circuiting issues.

The customized bin labels 106 exemplarily illustrated in FIG. 1A and FIGS. 2A-2B, on the upper surface 104a of the bin cover layer 104 constitute the seventh component layer 307. The seventh component layer 307 comprises generic information comprising, for example, color coded dosage times for days of the week, medication bins 102 of the day, a company name, contact details, other contact information, etc., printed thereon. The eighth component layer 308 is a layer of perforations 105 on the bin cover layer 104 as exemplarily illustrated in FIG. 1A, which match the perforations 110 on the support frame 101 exemplarily illustrated in FIG. 1B. The ninth component layer 309 is a final layer comprising personalized printing for healthcare recipients provided on the upper surface 104a of the bin cover layer 104. The ninth component layer 309 represents the printing of healthcare recipient specific medication information and other healthcare recipient information printed on the customized bin labels 106. The printing of the customized bin labels 106 is performed at one or more of multiple refill stations. The medication organizer tray apparatus 100 is created by attaching the component layers 309, 308, 307, 306, 305, 304, and 303 in the arrangement order shown in FIG. 3 to the component layers 302 and 301 in the arrangement order shown in FIG. 3.

Figure 4A:
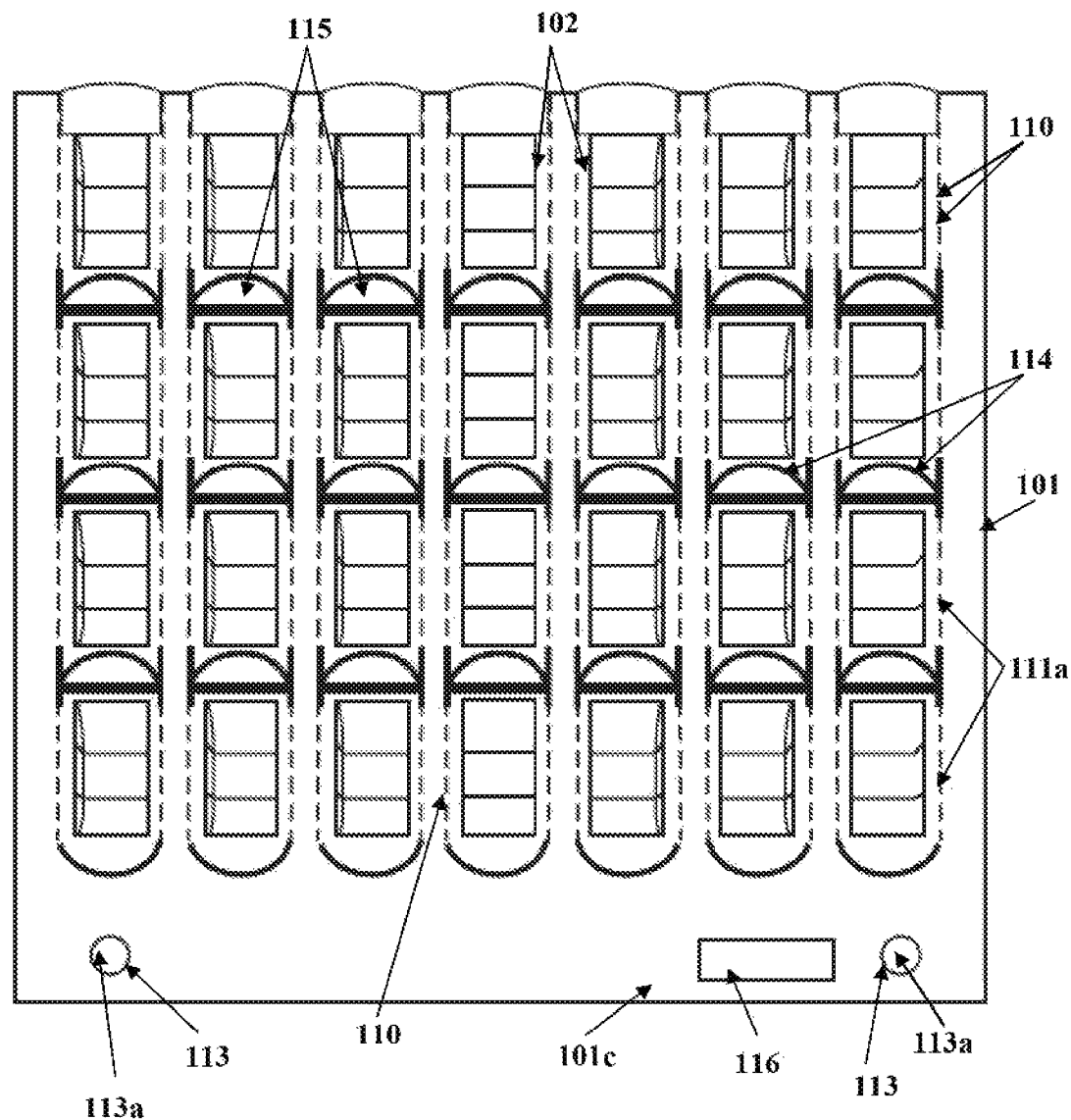
FIG. 4A exemplarily illustrates a top plan view of a support frame of the medication organizer tray apparatus.

FIG. 4A exemplarily illustrates a top plan view of the support frame 101 of the medication organizer tray apparatus 100 exemplarily illustrated in FIGS. 1A-IC and FIGS. 2A-2B. The support frame 101 is configured as a support base for supporting the other layers, for example, 303, 304, 305, 306, 307, 308, and 309 exemplarily illustrated in FIG. 3. The support frame 101 comprises multiple apertures 111 exemplarily illustrated in FIG. 1B, positioned at predefined intervals from each other. The apertures 111 of the support frame 101 are configured to house the medication bins 102. FIG. 4A also shows the perforations 110 positioned proximal to the outer edges 11a of the apertures 111 of the support frame 101. The perforations 110 on the support frame 101 are rigid and of a predefined shape to facilitate removal of the medication bins 102 from the support frame 101 without damaging the integrity of the support frame 101. The perforations 110 on the support frame 101 are configured in a shape that maintains the integrity of the medication organizer tray apparatus 100, when a majority of the medication bins 102 are removed from the support frame 101. The support frame 101 further comprises cut edges 114 for facilitating removal of the medication bins 102 from the apertures 111 of the support frame 101. Each cut edge 114 allows easy removal of a specific medication bin 102. In an embodiment, each of the medication bins 102 comprises a raised bump front edge 115 for facilitating easy removal of each of the medication bins 102 from the support frame 101. A healthcare recipient can remove a medication bin 102 from the support frame 101 by pulling the raised bump front edge 115 of the medication bin 102.

Figure 17A:
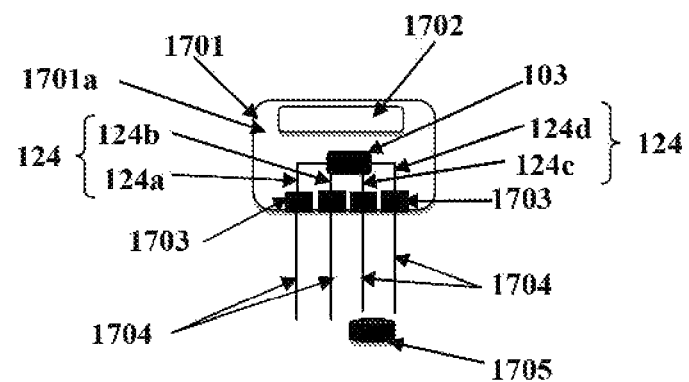
FIGS. 17A-17B exemplarily illustrate embodiments of an electronic identification component of the medication organizer tray apparatus.
Figure 17B:
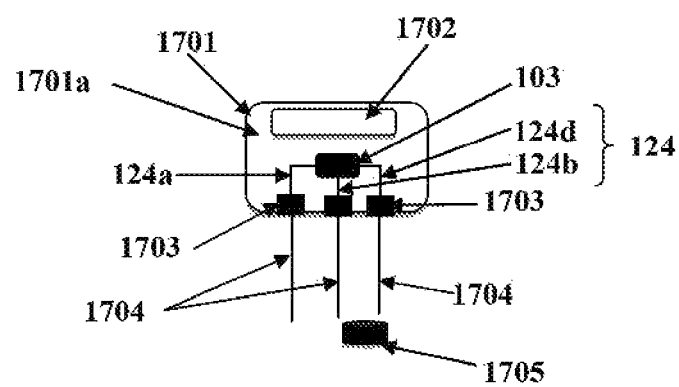

As exemplarily illustrated in FIG. 4A, the medication organizer tray apparatus 100 further comprises a receptacle 116 positioned, for example, proximal to a lower end 101c of the support frame 101 for accommodating an electronic identification component 103 exemplarily illustrated in FIGS. 17A-17B. In an embodiment, the electronic identification component 103 is placed face down in the receptacle 116 of the support frame 101 and embedded into the support frame 101. The support frame 101 further comprises one or more depressed button heads 113 exemplarily illustrated in FIG. 1C, for facilitating attachment and alignment of the medication organizer tray apparatus 100 to the receptacle base 2101 as exemplarily illustrated in FIGS. 21A-21B and FIG. 22. FIG. 4A exemplarily illustrates an upper portion 113a of each depressed button head 113. The medication organizer tray apparatus 100 is aligned with the receptacle base 2101 via the depressed button heads 113 of the support frame 101 to ensure that proper electrical contact is established between the medication organizer tray apparatus 100 and the receptacle base 2101.

Figure 4B:
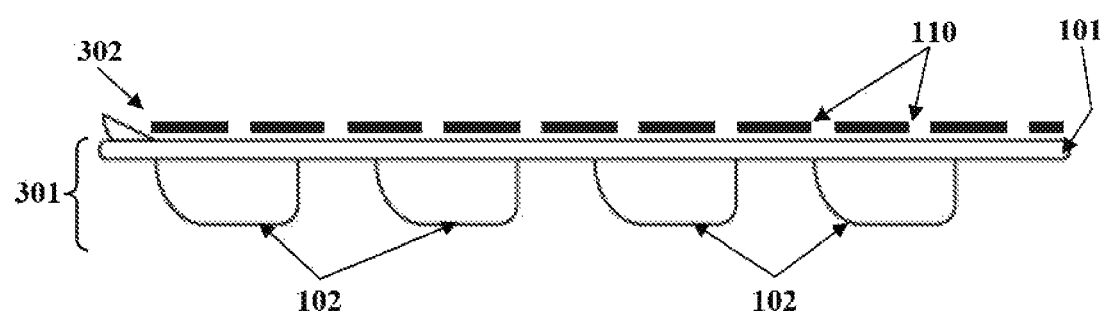
FIG. 4B exemplarily illustrates a side elevation view of the support frame of the medication organizer tray apparatus, showing medication bins.

FIG. 4B exemplarily illustrates a side elevation view of the support frame 101 of the medication organizer tray apparatus 100 exemplarily illustrated in FIGS. 1A-1C and FIGS. 2A-2B, showing medication bins 102. The support frame 101 exemplarily illustrated in FIG. 4B, is configured by combining the first component layer 301 and the second component layer 302 of the medication organizer tray apparatus 100 as disclosed in the detailed description of FIG. 3. The first component layer 301 of the medication organizer tray apparatus 100 comprises the support frame 101 with the medication bins 102 placed in the apertures 111 of the support frame 101 exemplarily illustrated in FIG. 1B, while the second component layer 302 comprises perforations 110 of the support frame 101 exemplarily illustrated in FIG. 3 and FIGS. 4A-4B. Each medication bin 102 is removed from the support frame 101 by pulling the medication bin 102 along with matching portions of the other component layers comprising 303, 304, 305, 306, 307, 308, and 309 exemplarily illustrated in FIG. 3, in a substantially upward direction with respect to the support frame 101 along the perforations 110 of the support frame 101 exemplarily illustrated in FIG. 4A. Each of the detached medication bins 102 is of a generally cup shaped configuration as exemplarily illustrated in FIGS. 9-13.

Figure 5:
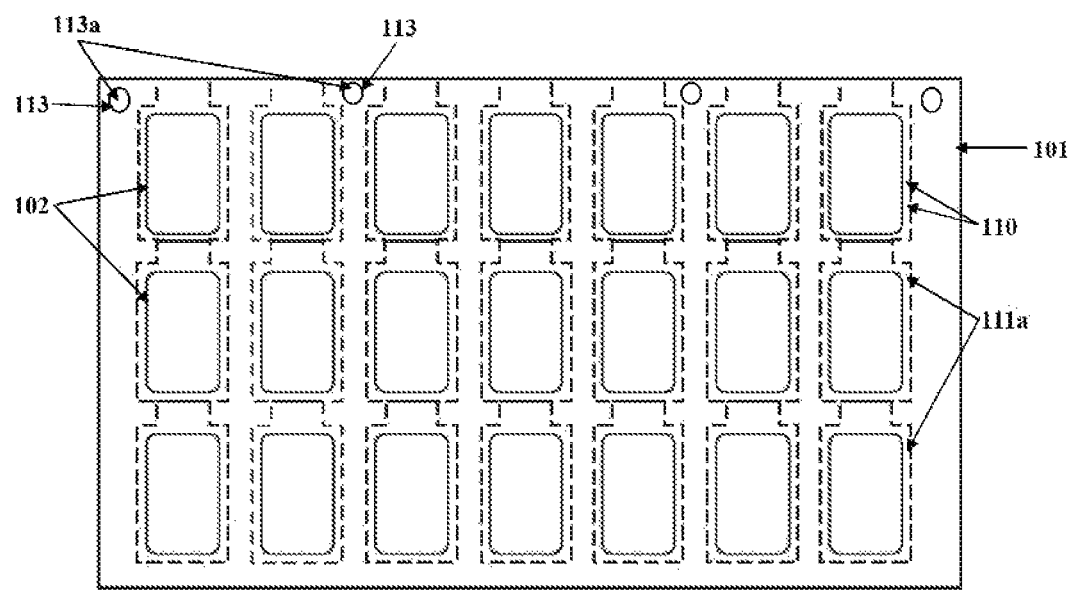
FIG. 5 exemplarily illustrates a top plan view of an embodiment of the support frame of the medication organizer tray apparatus.

FIG. 5 exemplarily illustrates a top plan view of an embodiment of the support frame 101 of the medication organizer tray apparatus 100 exemplarily illustrated in FIGS. 1A-1C and FIGS. 2A-2B. FIG. 5 shows the support frame 101 housing the medication bins 102 in the apertures 111 exemplarily illustrated in FIG. 1B, the perforations 110 positioned proximal to the outer edges 111a of the apertures 111 of the support frame 101, and the upper portion 113a of each depressed button head 113 exemplarily illustrated in FIG. 1C. In this embodiment, the medication bins 102 are of the same size as exemplarily illustrated in FIG. 5.

Figure 6:
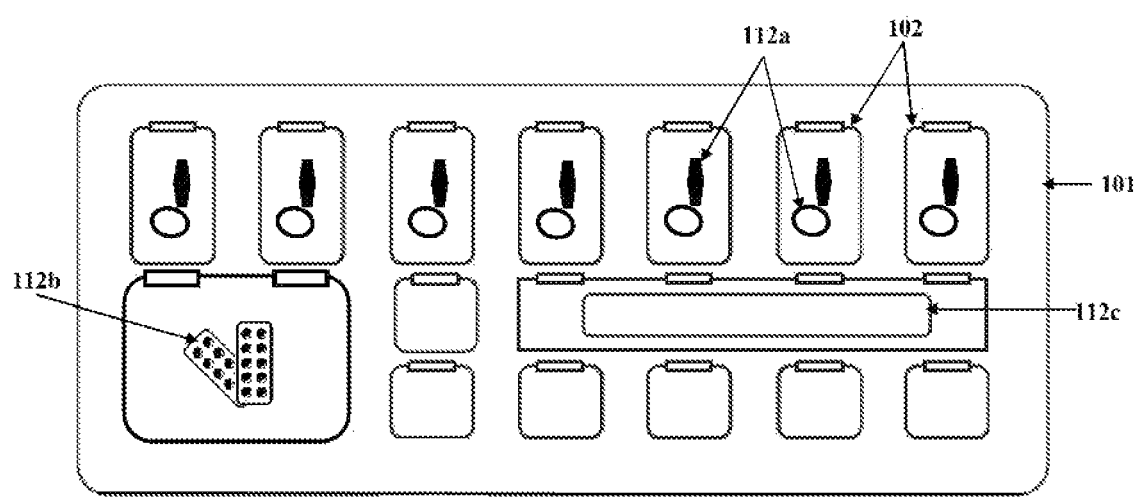
FIG. 6 exemplarily illustrates a top plan view of an embodiment of the support frame of the medication organizer tray apparatus, showing medication bins of different shapes and sizes for accommodating medications of different types.

FIG. 6 exemplarily illustrates a top plan view of an embodiment of the support frame 101 of the medication organizer tray apparatus 100 exemplarily illustrated in FIGS. 1A-1C and FIGS. 2A-2B, showing medication bins 102 of different shapes and sizes for accommodating medications, for example, 112a, 112b, and 112c of different types. In this embodiment, the support frame 101 houses medication bins 102 of different shapes. The medication bins 102 are shaped to accommodate medications, for example, pills 112a, blister packed medications 112b in the form of cards or as individual doses, parenterals 112c such as insulin vials, syringes, inhalers, small tubes or containers containing ointments, injection vials, etc. In an embodiment, the medication bins 102 are configured as vials. In another embodiment, the medication bins 102 are configured as thermoform cups.

Figure 7:
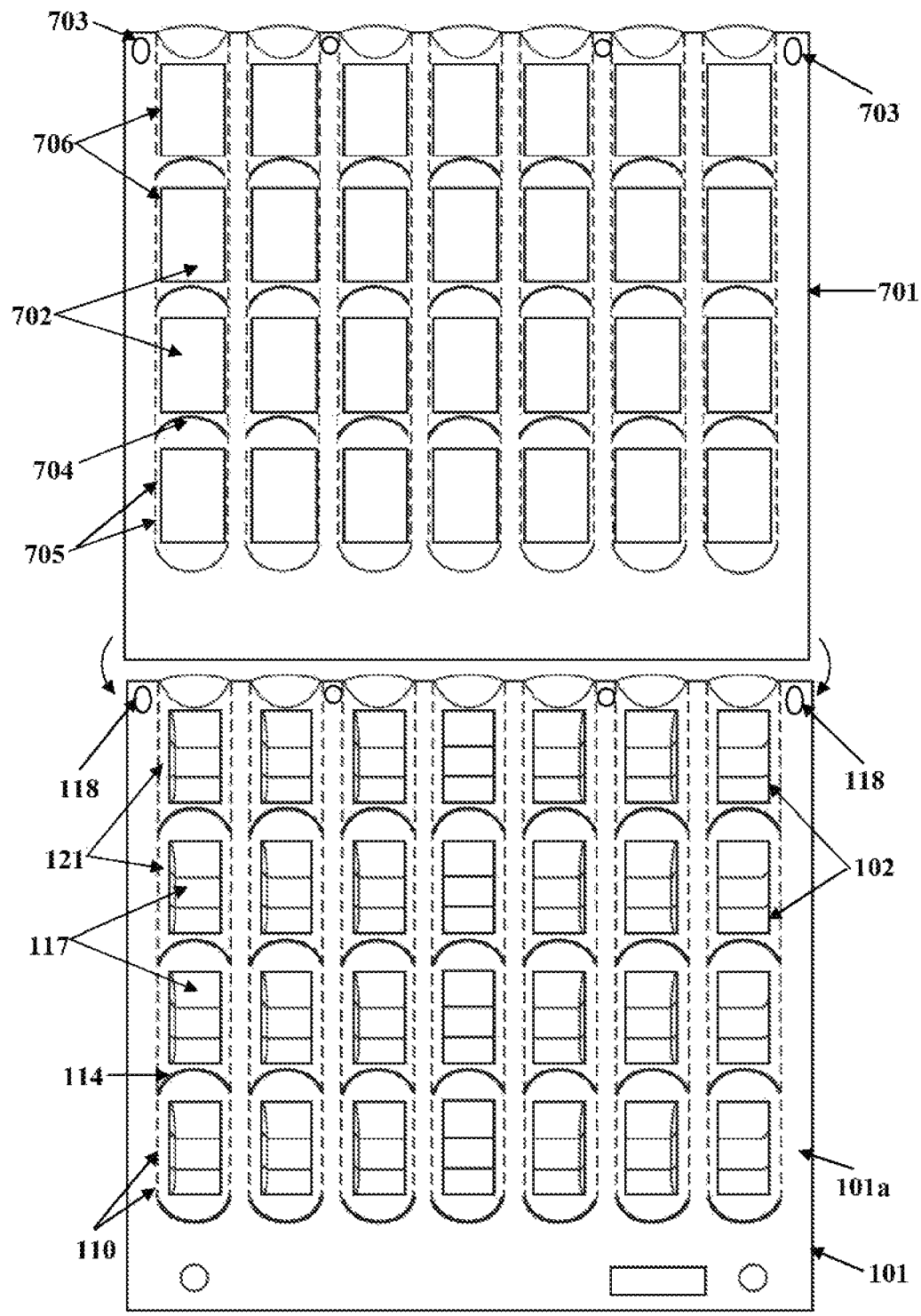
FIG. 7 exemplarily illustrates a coated layer of the medication organizer tray apparatus configured to be removably attached to the upper surface of the support frame.

FIG. 7 exemplarily illustrates a coated layer 701 of the medication organizer tray apparatus 100 exemplarily illustrated in FIGS. 1A-IC and FIGS. 2A-2B, configured to be removably attached to the upper surface 101a of the support frame 101. The medication bins 102 housed in the support frame 101 accommodate medications 112 exemplarily illustrated in FIG. 1B, comprising, for example, parenterals that have a significant weight. The weight of the medications 112 can be, for example, about 50 grams. The range of the weight of the medications 112 varies based on a type of a container used to contain the medications 112. In such situations, the support frame 101 requires additional support to maintain the integrity of the medication organizer tray apparatus 100. For accommodating medications 112 of substantially high weight, the medication organizer tray apparatus 100 is constructed, for example, in a sandwich board configuration that provides a stronger structure. For such a configuration of the medication organizer tray apparatus 100, the coated layer 701, for example, a cardboard cover is provided with openings 702 and lip sections 706 that mirror openings 117 of the medication bins 102 and the adjacent lips 121 of the medication bins 102 respectively. In an embodiment, the coated layer 701 made, for example, of paper is attached to the support frame 101 using an adhesive. In another embodiment, the coated layer 701 is attached to the support frame 101 using a clamp (not shown) on two sides of the support frame 101 to securely connect the coated layer 701 to the support frame 101 and strengthen the medication organizer tray apparatus 100. The coated layer 701 provides additional support to the support frame 101, for example, when the medications 112 to be accommodated in the medication bins 102 are heavy. The coated layer 701 comprises coated layer alignment holes 703 that mirror tray alignment holes 118 in the support frame 101 as exemplarily illustrated in FIG. 7. The coated layer 701 further comprises coated layer cut edges 704 and coated layer perforations 705 that mirror the cut edges 114 and the perforations 110 of the support frame 101 respectively, as exemplarily illustrated in FIG. 7.

In an embodiment, the coated layer 701 forms a flap or a panel that folds over the support frame 101 and offers additional surface area for various purposes. The coated layer 701 is configured to display supplementary information printed thereon, for example, patient name, patient phone number, patient address, etc. The supplementary information further comprises, for example, coupons, advertisements, incentives for medication adherence such as reward points, lottery tickets, bingo numbers, bingo cards, etc., status of incentives such as status of reward points, appointments for a week, reminders, quotes, images, wellness information, wellness messages, gaming information, quick reference telephone numbers of healthcare providers such as caregivers, case workers, physicians, etc.

Figure 8:
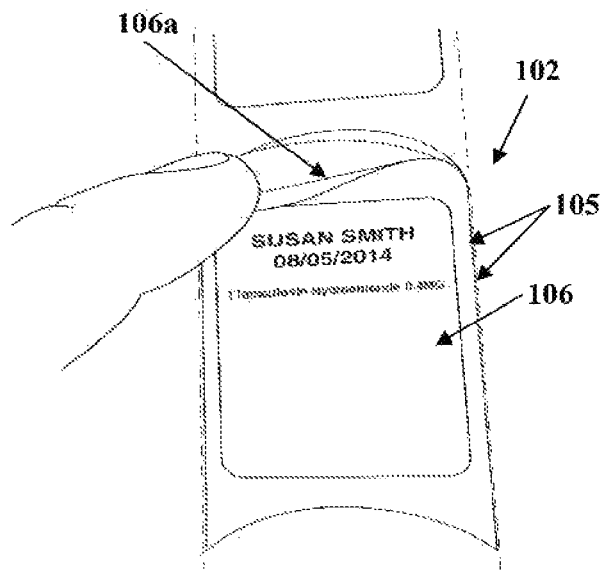
FIG. 8 exemplarily illustrates a top perspective view of a medication bin of the medication organizer tray apparatus for accommodating medications.

FIG. 8 exemplarily illustrates a top perspective view of a medication bin 102 of the medication organizer tray apparatus 100 exemplarily illustrated in FIGS. 1A-IC and FIGS. 2A-2B, for accommodating medications 112 exemplarily illustrated in FIG. 1B. As exemplarily illustrated in FIG. 8, the customized bin label 106 that seals the medication bin 102 can be removed by pulling a top edge 106a of the customized bin label 106 along the perforations 105 of the bin cover layer 104. The customized bin label 106 on the medication bin 102 is removed to access the medications 112 contained in the medication bin 102. The customized bin label 106 comprises, for example, a name of a patient, a date for consuming the medications 112 accommodated in the medication bin 102, name of each of the medications 112, etc., as exemplarily illustrated in FIG. 8.

Figure 9:
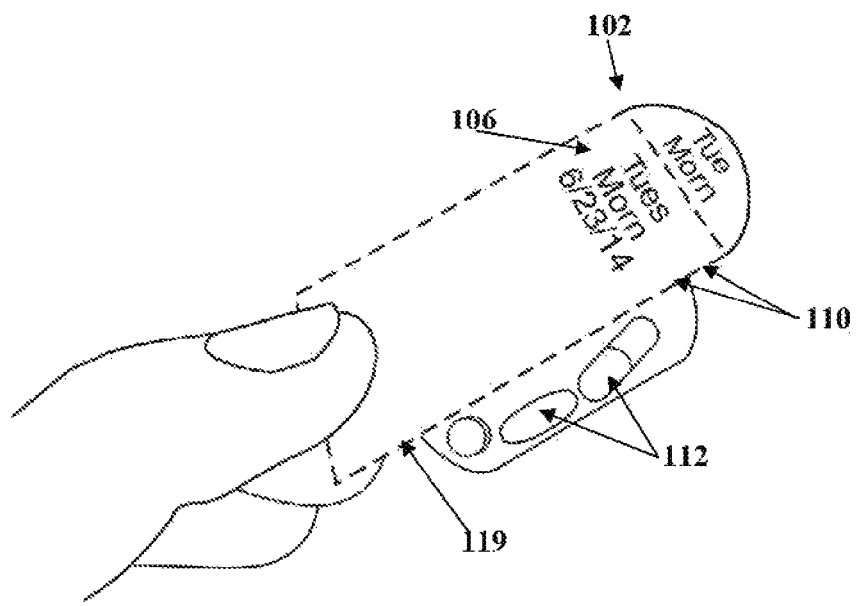
FIG. 9 exemplarily illustrates a perspective view of a medication bin of the medication organizer tray apparatus removed from a support frame of the medication organizer tray apparatus.

FIG. 9 exemplarily illustrates a perspective view of a medication bin 102 of the medication organizer tray apparatus 100 exemplarily illustrated in FIGS. 1A-IC and FIGS. 2A-2B, removed from the support frame 101 exemplarily illustrated in FIGS. 1A-7. In an embodiment, when a medication bin 102 is removed from the medication organizer tray apparatus 100 by pulling the medication bin 102 away from the support frame 101 along the perforations 110 of the support frame 101 and the perforated rims 119 of the medication bin 102, the whole medication bin 102 peels off from the support frame 101, intact with the customized bin label 106.

Figure 10:
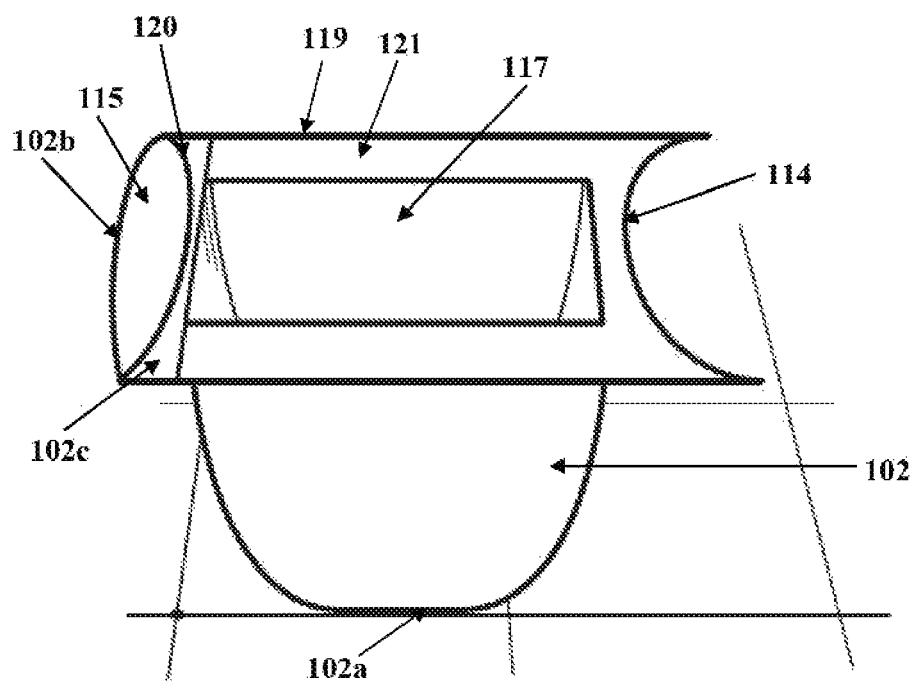
FIG. 10 exemplarily illustrates a side perspective view of a medication bin of the medication organizer tray apparatus, showing a raised bump front edge.

FIG. 10 exemplarily illustrates a side perspective view of a medication bin 102 of the medication organizer tray apparatus 100 exemplarily illustrated in FIGS. 1A-IC and FIGS. 2A-2B, showing a raised bump front edge 115. In an embodiment, each medication bin 102 comprises a cut edge 114, a bend 120, and a raised bump front edge 115 as exemplarily illustrated in FIG. 10, for facilitating removal of the medication bin 102 from the support frame 101 exemplarily illustrated in FIG. 1B. Each medication bin 102 comprises specific cut edges 114 apart from the perforated rims 119 which allow easy removal of that specific medication bin 102. The raised bump front edge 115 of each medication bin 102 is a bump or a tab that can be lifted up for facilitating removal of the medication bin 102 from the support frame 101. The raised bump front edge 115 that can be folded at a bend 120 is positioned on a top edge 102b of the upper surface 102c of the medication bin 102 to allow removal of the medication bin 102 from the support frame 101. In an embodiment, the medication bin 102 is configured as a transparent bottle such that camera images can be taken of the lower surface 102a of the medication bin 102 post robotic or pharmacist fills of medications 112. The opening 117 of the medication bin 102 is sealed with the customized bin label 106 as exemplarily illustrated in FIGS. 8-9. There is no adhesive 126a behind the portion of the adhesive protective paper layer 126 exemplarily illustrated in FIG. 18A, that contacts the raised bump front edge 115 of the medication bin 102. Upon removal of the medication bin 102 from the support frame 101, the portion of the adhesive protective paper layer 126 on the raised bump front edge 115 of the medication bin 102 is easily accessible, as that portion is not glued. The raised bump front edge 115 of the medication bin 102 allows the medication bin 102 to be easily removed from the support frame 101 and reduces the need for a larger surface area to reduce the size and bulkiness of the medication organizer tray apparatus 100.

Figure 11A:
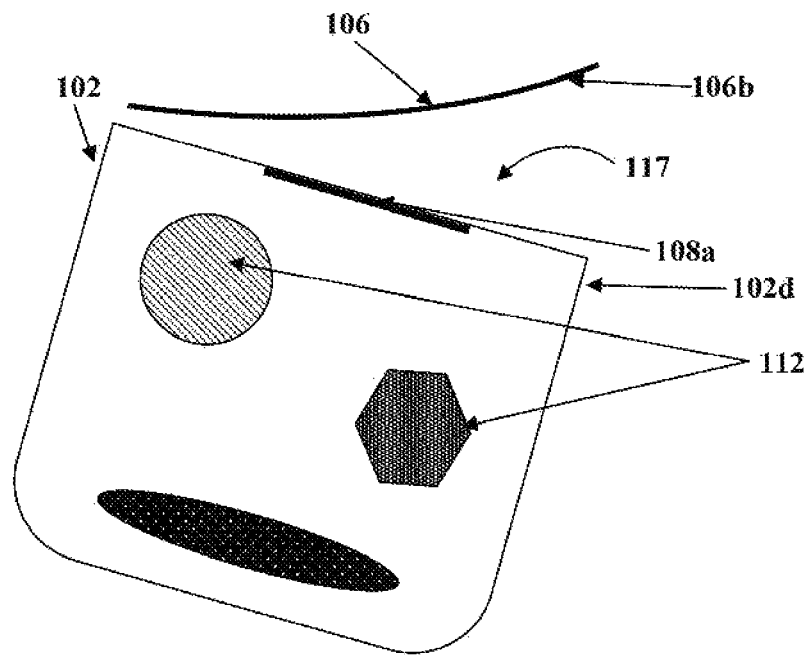
FIGS. 11A-11B exemplarily illustrate different views of embodiments of a medication bin of the medication organizer tray apparatus, showing conductive sensor circuit lines.
Figure 11B:
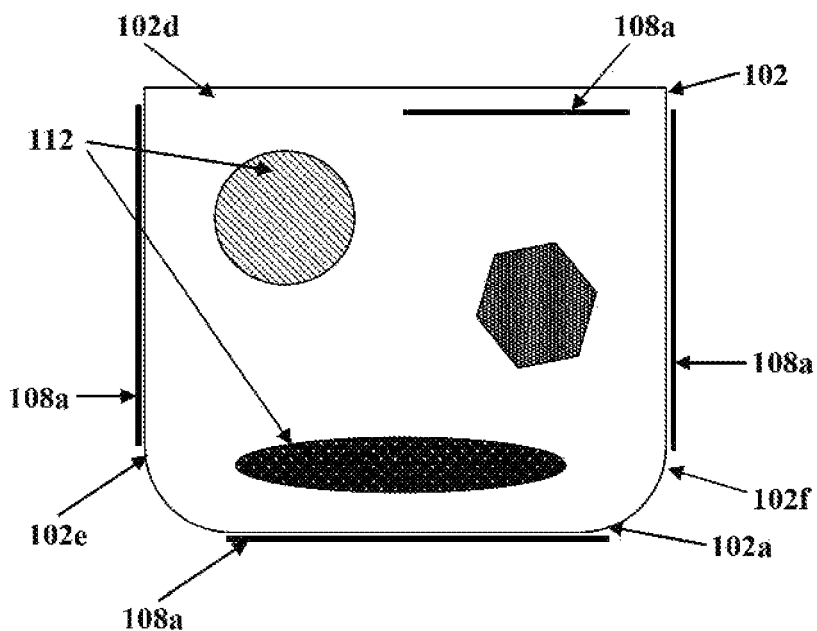

FIGS. 11A-11B exemplarily illustrate different views of embodiments of a medication bin 102 of the medication organizer tray apparatus 100 exemplarily illustrated in FIGS. 1A-IC and FIGS. 2A-2B, showing conductive sensor circuit lines 108a. FIG. 11A exemplarily illustrates a front elevation view of the medication bin 102, showing the customized bin label 106 removed from the medication bin 102. In an embodiment, the customized bin label 106 is, for example, a paper label, a plastic label, or a label made of some other material which is glued to the medication bin 102. As exemplarily illustrated in FIG. 11A, the customized bin label 106 seals the opening 117 of the medication bin 102. As exemplarily illustrated in FIG. 11A, the customized bin label 106 is peeled away to access the medications 112 contained in the medication bin 102. Furthermore, as exemplarily illustrated in FIG. 11A, a conductive sensor circuit line 108a is positioned on an upper section 102d of the medication bin 102. In an embodiment, the bottom surface 106b of each customized bin label 106 displays additional information, for example, wellness information, reminders, incentives for medication adherence such as award points, lottery tickets, gaming information, or bingo numbers, quotes such as motivational and religious quotes or a quote of the day, pictures of family members, etc.

FIG. 11B exemplarily illustrates a front elevation view of the medication bin 102, showing conductive sensor circuit lines 108a running along the side surfaces 102e and 102f of the medication bin 102, on a lower surface 102a of the medication bin 102, and at the upper section 102d of the medication bin 102. To preclude tampering of high priced and/or abusable medications 112, for example, pain killers, opioids, etc., contained in the medication bin 102 by creation of incisions or cuts on the side surfaces 102e and 102f of the medication bin 102 and on the lower surface 102a of the medication bin 102, the medication organizer tray apparatus 100 exemplarily illustrated in FIGS. 1A-IC and FIGS. 2A-2B, provides additional security via detection circuitry on the medication bins 102, for example, by adding conductive sensor circuit lines 108a on an upper section 102d of each medication bin 102, the sides surfaces 102e and 102f of the medication bin 102, and on the lower surface 102a of the medication bin 102 as exemplarily illustrated in FIGS. 11A-11B, thereby making the overall surface of the medication bin 102 completely conductive. Any incision or a cut in any part of the medication bin 102 can be detected as a change in electrical properties of the medication bin 102 as measured by sensitive detection circuitry 1601 exemplarily illustrated in FIG. 16C, of the receptacle base 2101 exemplarily illustrated in FIGS. 21A-21B and FIG. 22, that is different from a change in electrical properties of the medication bin 102 detected while removing the medication bin 102 from the support frame 101 exemplarily illustrated in FIGS. 1A-7, during standard use of the medication organizer tray apparatus 100.

Figure 12:
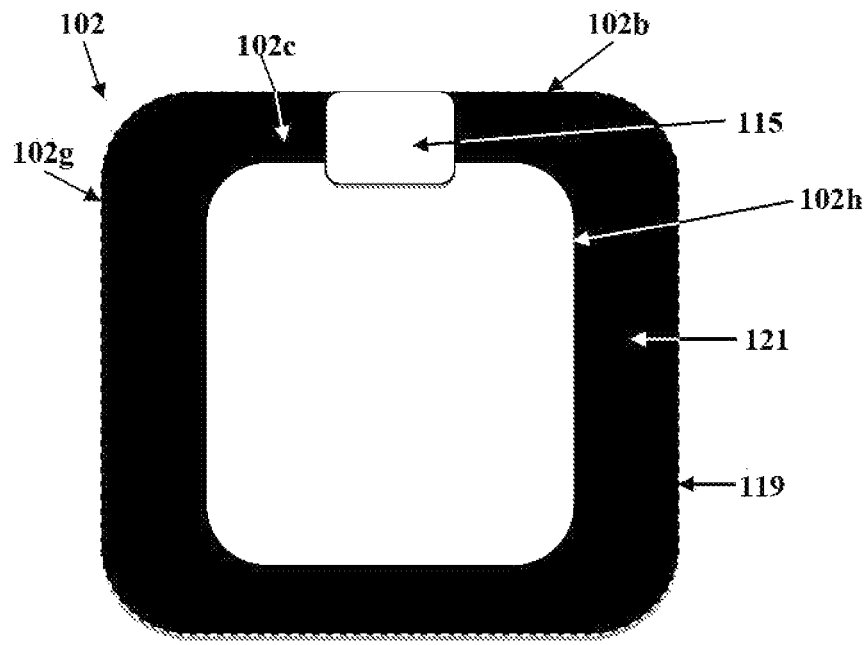
FIG. 12 exemplarily illustrates a top plan view of an embodiment of a medication bin of the medication organizer tray apparatus.

FIG. 12 exemplarily illustrates a top plan view of an embodiment of a medication bin 102 of the medication organizer tray apparatus 100 exemplarily illustrated in FIGS. 1A-1C and FIGS. 2A-2B. As exemplarily illustrated in FIG. 12, in an embodiment, the medication bin 102 comprises a raised bump front edge 115 on a top edge 102b of an upper surface 102c of the medication bin 102 for facilitating easy removal of the medication bin 102 from the support frame 101 exemplarily illustrated in FIGS. 1A-7. In an embodiment, the raised bump front edge 115 is configured as a bump on the top edge 102b of the upper surface 102c of the medication bin 102, when the medication bin 102 is configured, for example, as a plastic cup for facilitating peeling off the customized bin label 106 exemplarily illustrated in FIGS. 8-9, from the medication bin 102. In an embodiment, the raised bump front edge 115 is a configured as a slot. Each medication bin 102 comprises perforated rims 119 at upper edges 102g of the medication bin 102. The perforated rims 119 attach the medication bin 102 to perforations 110 positioned proximal to the outer edges 111a of each aperture 111 of the support frame 101 as exemplarily illustrated in FIG. 1B. The perforated rims 119 of each medication bin 102 facilitate removal of each individual medication bin 102 or a set of medication bins 102 for the day, or for multiple days from the support frame 101. Each medication bin 102 is, for example, cup shaped and comprises a lip 121 extending around a periphery 102h of the upper surface 102c of the medication bin 102. The lip 121 of the medication bin 102 facilitates enhanced access to the medication bin 102 and allows easy handling or carrying of the medication bin 102 by healthcare recipients diagnosed with certain medical conditions, for example, arthritis, nerve disorders that cause tremors, etc.

Figure 13:
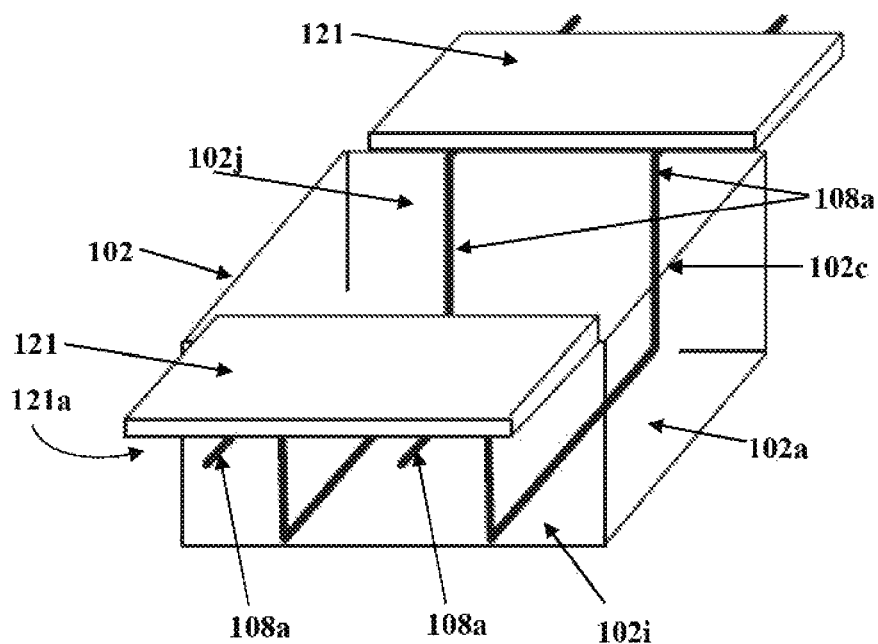
FIG. 13 exemplarily illustrates a perspective view of an embodiment of the medication bin, showing conductive sensor circuit lines running along a front surface of the medication bin, a rear surface of the medication bin, a lower surface of the medication bin, and a lower surface of a lip of the medication bin.
Figure 14A:
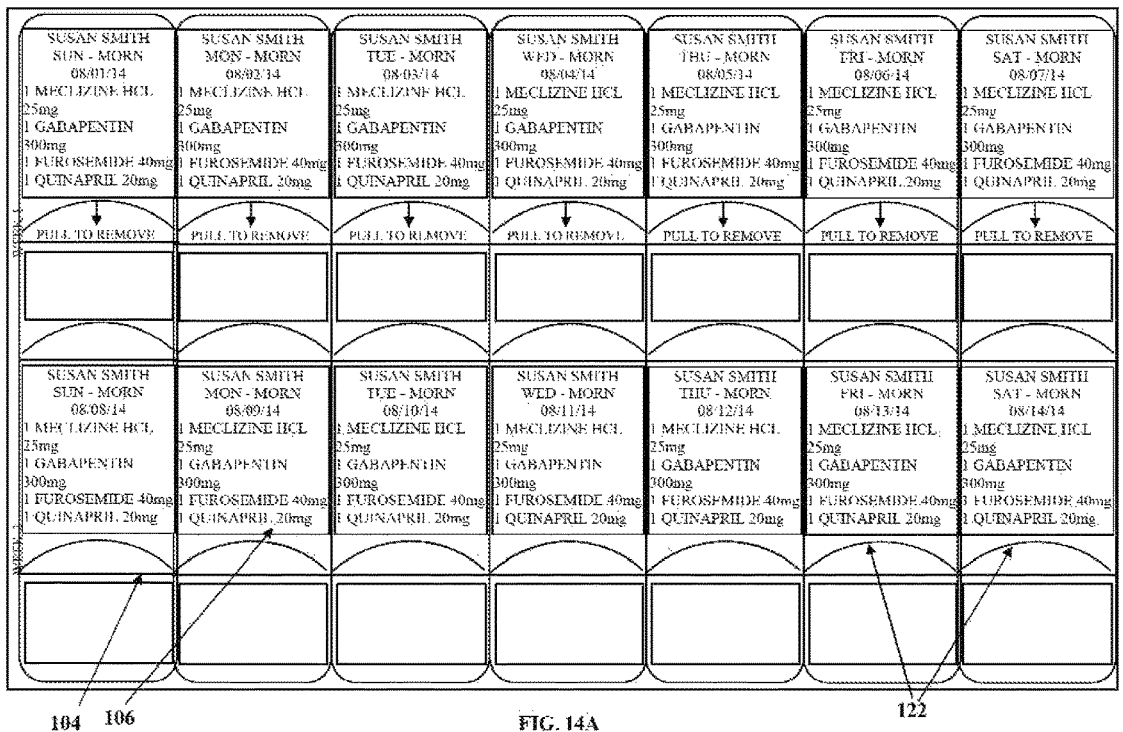
Figure 16A:
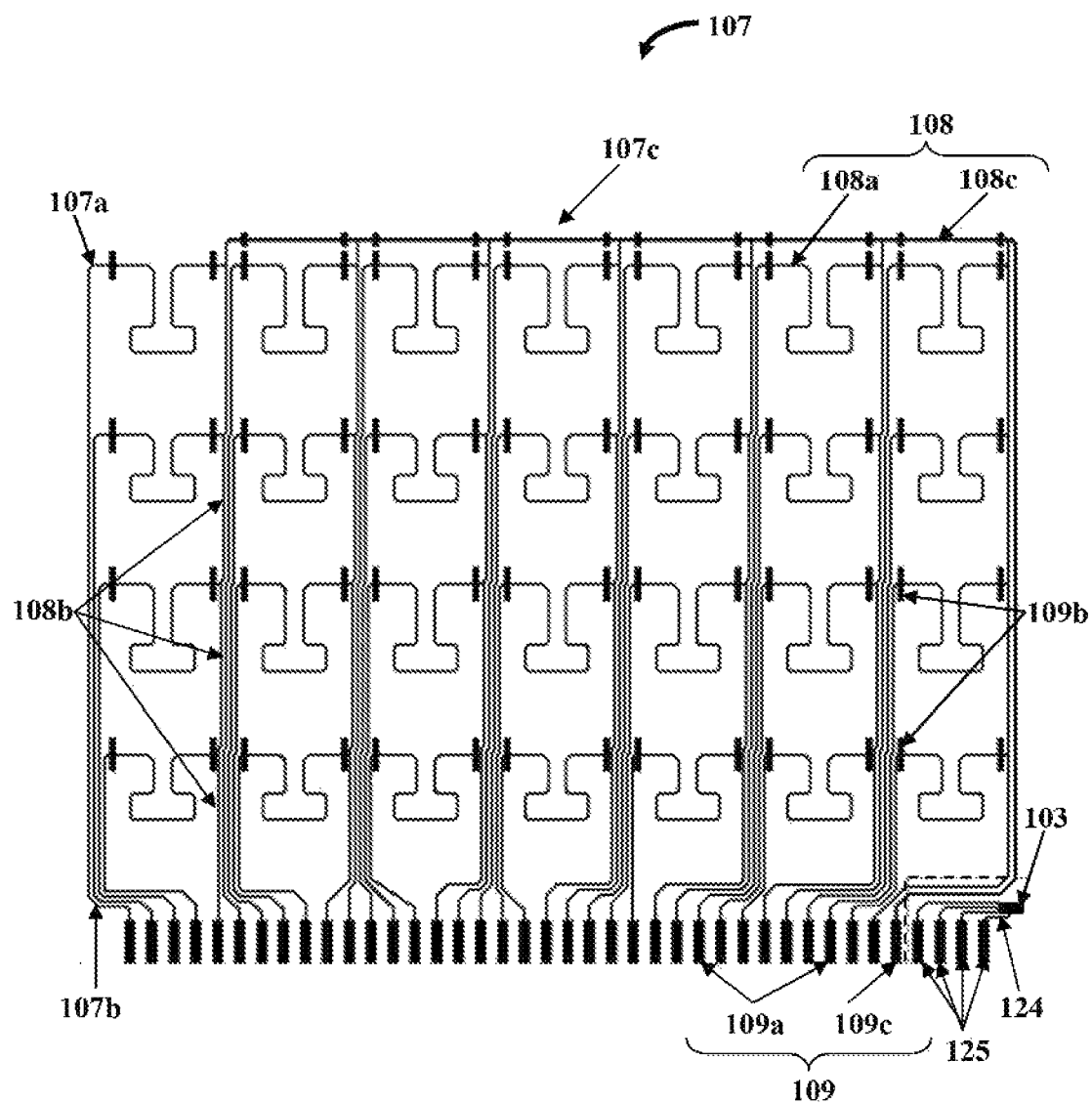
FIG. 16A exemplarily illustrates a conductive circuit layer of the medication organizer tray apparatus, showing conductive lines and conductive pads.
Figure 16B:
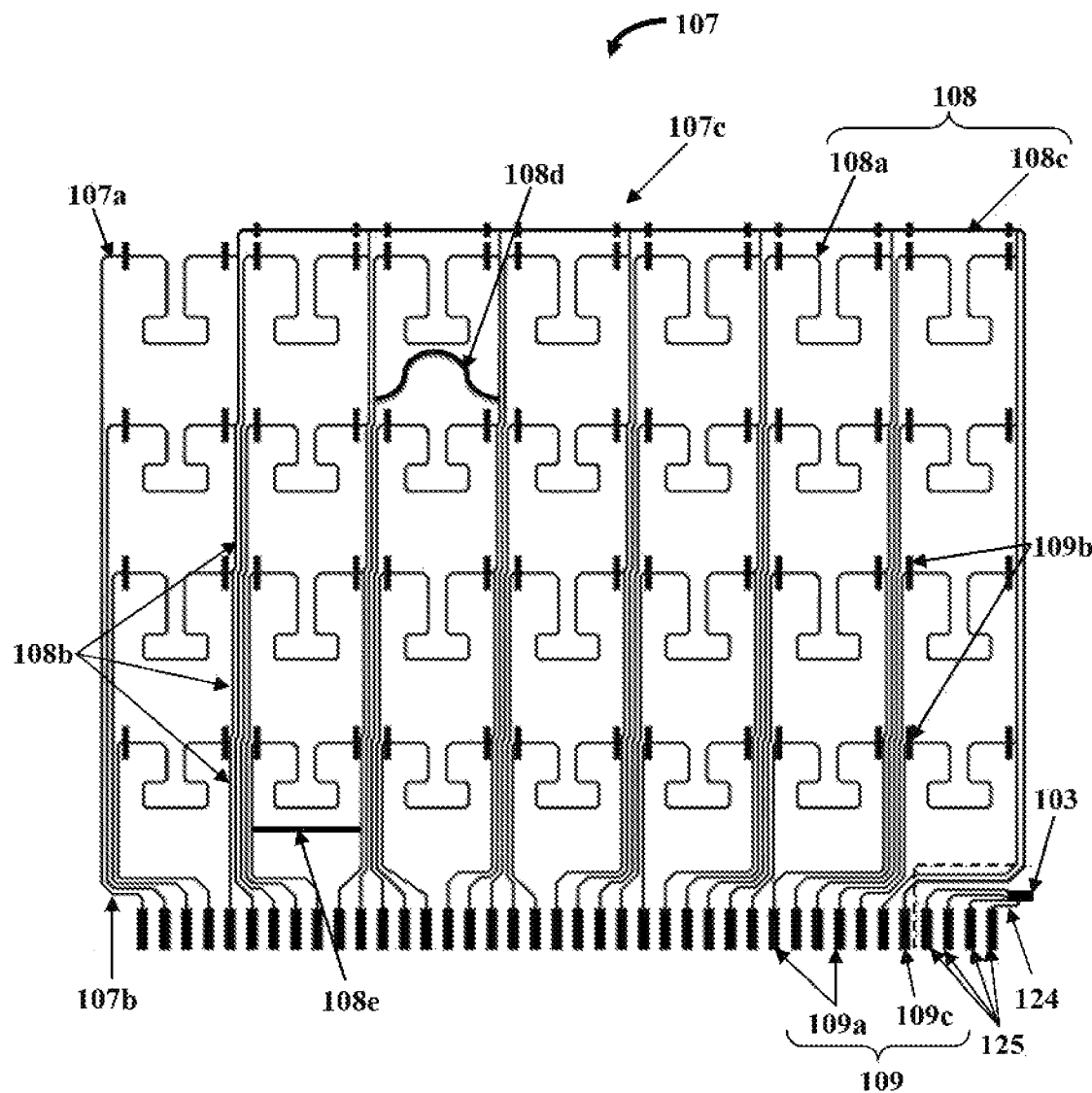
FIG. 16B exemplarily illustrates an embodiment of the conductive circuit layer of the medication organizer tray apparatus, showing conductive sensor circuit lines of different patterns.
Figure 16C:
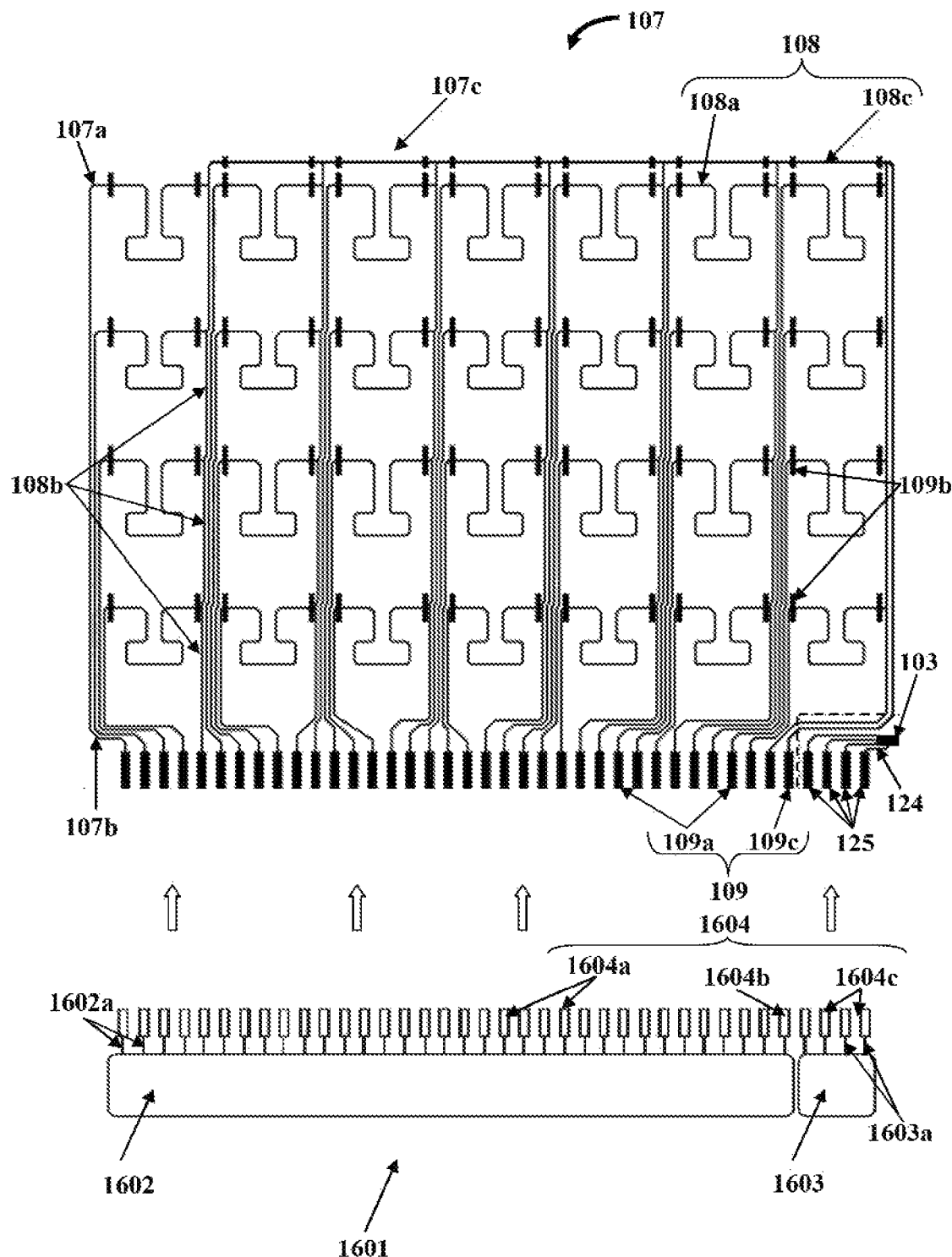
FIG. 16C exemplarily illustrates communication between the conductive circuit layer of the medication organizer tray apparatus and detection circuitry of a receptacle base.

FIG. 13 exemplarily illustrates a perspective view of an embodiment of the medication bin 102, showing conductive sensor circuit lines 108a running along a front surface 102i of the medication bin 102, a rear surface 102j of the medication bin 102, a lower surface 102a of the medication bin 102, and a lower surface 121a of a lip 121 of the medication bin 102. The circuit mechanism of the conductive circuit layer 107 disclosed in the detailed description of FIGS. 16A-16C, is activated, when a healthcare recipient removes the medication bins 102 from the medication organizer tray apparatus 100 exemplarily illustrated in FIGS. 1A-IC and FIGS. 2A-2B. The conductive sensor circuit lines 108a of the conductive circuit layer 107 exemplarily illustrated in FIGS. 1A-1B and FIGS. 16A-16C, are ruptured when the medication bins 102 are removed, which are sensed by the detection circuitry 1601 of the receptacle base 2101 exemplarily illustrated in FIG. 16C.

In an embodiment, multiple conductive sensor circuit lines 108a are applied or printed around each medication bin 102 and on the lower surface 102a of each medication bin 102 as exemplarily illustrated in FIG. 13, for example, via conductive ink printing such that any incision or a cut in the medication bin 102 can be detected by a break in the conductive sensor circuit lines 108a. In an embodiment, the layering of the conductive circuit layer 107 around the medication bin 102 is created via conductive pad printing around the medication bin 102. Multiple layers of conductive sensor circuit lines 108a are created to allow one or more of the conductive sensor circuit lines 108a to cross over another one or more of the conductive sensor circuit line 108a without short circuiting the conductive circuit layer 107. The conductive ink is selectively printed on each medication bin 102 such that the conductive circuit layer 107 on the lower surface 104b of the bin cover layer 104 exemplarily illustrated in FIG. 18A, when placed on top of the medication bins 102, makes an appropriate electrical connection with the medication bins 102 for enabling detection of any incision or any cut in the medication bins 102. For example, conductive ink is printed on the upper surface 102c of the medication bin 102, on the front surface 102i of the medication bin 102, on the rear surface 102j of the medication bin 102, and on the lower surface 102a of the medication bin 102 such that the conductive circuit layer 107 configured, for example, as a conductive paper cover can be placed on top of the medication bin 102, to allow detection of any incision or any cut in the medication bin 102. In an embodiment, conductive ink is also printed on the lower surface 121a of each lip 121 of the medication bin 102 as exemplarily illustrated in FIG. 13. When the bin cover layer 104 is placed on such a medication bin 102, the conductive lines 108 on the lower surface 104b of the bin cover layer 104 exemplarily illustrated in FIG. 18A, connects to the conductive sensor circuit lines 108a on the lips 121 of the medication bin 102 to make the circuit connection, so that removal of the medication bin 102 can be detected on breakage of the circuit connection.

In an embodiment, the medication bins 102 are made of an electrically conductive material for communicating with the receptacle base 2101 for enabling detection of removal of each medication bin 102 from the support frame 101 exemplarily illustrated in FIGS. 1A-7, and detection of tampering of the medication bins 102. The medication bins 102 are configured, for example, as thermoform cups made of a conductive material to make the medication bins 102 tamper proof. In this embodiment, electrical resistance is measured by an electronic current measuring circuit, that is, the detection circuitry 1601 of the receptacle base 2101, to detect tampering when cuts or incisions are made on one or more of the surfaces, for example, 102i, 102j, 102a, etc., of the medication bin 102. The conductive material of the medication bins 102 conducts electricity and when a small current is supplied by a power source (not shown), which is detected by the detection circuitry 1601 of the receptacle base 2101, any cuts or any incisions in one or more of the surfaces, for example, 102i, 102j, 102a, etc., of the medication bins 102 is detected by the detection circuitry 1601 of the receptacle base 2101 by measuring resistance in the conductive circuit layer 107 in a manner similar to detection of line breaks in the conductive sensor circuit lines 108a of the medication bins 102 as disclosed in the detailed description of FIGS. 16A-16C.

FIGS. 14A-14D exemplarily illustrate top plan views of different embodiments of the bin cover layer 104 of the medication organizer tray apparatus 100 exemplarily illustrated in FIGS. 1A-1C and FIGS. 2A-2B, showing customized bin labels 106 removably configured within the bin cover layer 104. The bin cover layer 104 is removably attached to the upper surface 101a of the support frame 101 exemplarily illustrated in FIG. 1A. The customized bin labels 106 of the bin cover layer 104 seal openings 117 of the medication bins 102 exemplarily illustrated in FIGS. 8-9. The lower surface 104b of the bin cover layer 104 is attached to the upper surface 101a of the support frame 101 by removing the adhesive protective paper layer 126 from the lower surface 104b of the bin cover layer 104 as disclosed in the detailed description of FIGS. 18A-18B. Adhesive used around the upper surface 101a of the support frame 101 is stronger than the adhesive used on the surface 101d surrounding the outer edges 111a of the apertures 111 of the support frame 101 between the medication bins 102 exemplarily illustrated in FIG. 18B, for facilitating easy removal of the medication bins 102 via the perforations 110 of the support frame 101 exemplarily illustrated in FIG. 1B and FIG. 4A. The bin cover layer 104 comprises perforations 105 exemplarily illustrated in FIG. 14C, positioned at predefined areas on the bin cover layer 104 to match perforations 110 positioned proximal to the outer edges 111a of the apertures 111 of the support frame 101. In an embodiment, the bin cover layer 104 further comprises cut portions 122 for accommodating the raised bump front edge 115 of each medication bin 102 exemplarily illustrated in FIG. 10 and FIG. 12.

In an embodiment, the customized bin labels 106 of the bin cover layer 104 conform to chapter 681 of the US Pharmacopeia standards. Each customized bin label 106 is, for example, a paper label sealed within or printed to the upper surface 104a of the bin cover layer 104 at a medication packaging location after a medication fill. The customized bin labels 106 comprise medication information printed according to the configuration of the medication organizer tray apparatus 100 with color coded days and times. For example, a seven day medication organizer tray apparatus 100 comprises customized bin labels 106 comprising medication information for seven days. The customized bin labels 106 comprise other information such as the name of the healthcare recipient, names of the medications 112 exemplarily illustrated in FIG. 1B, FIG. 9, and FIGS. 11A-11B, directions to be followed, name of a healthcare professional, date of preparation, date of administration, etc., as exemplarily illustrated in FIGS. 14A-14D. Furthermore, the customized bin labels 106 provide individual bin labeling with a unique printout on the individual customized bin labels 106 displaying, for example, a description of the contents of each medication bin 102, a time of day for taking the medications 112, for example, morning, noon/day, or evening, etc., as exemplarily illustrated in FIGS. 14A-14D.

In addition to the medication information, the bin cover layer 104 of the medication organizer tray apparatus 100 comprises additional information, for example, an identifier code 123 as exemplarily illustrated in FIGS. 14C-14D, a healthcare recipient picture, a personalized website link to the healthcare recipient's information, a user identifier (ID) of the healthcare recipient, past week or past month overall adherence rate or each medication adherence rate, overall or each medication possession ratio, bonus award points based on factors such as how well healthcare recipients have been adherent to the medications 112 in the medication bins 102, etc., a list of medications 112, pharmacy and $R_x$ number, healthcare provider information, instructions, etc., printed on the customized bin labels 106, or on a separate page, or on other surface areas of the bin cover layer 104.

Figure 15A:
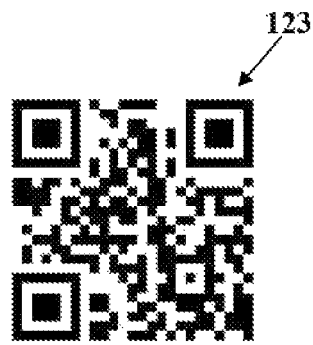
FIGS. 15A-15B exemplarily illustrate different types of identifier codes configured to be printed on the bin cover layer of the medication organizer tray apparatus.
Figure 15B:

FIGS. 15A-15B exemplarily illustrate different types of identifier codes 123 configured to be printed on the bin cover layer 104 as exemplarily illustrated in FIGS. 14C-14D. The identifier code 123 is configured, for example, as a quick response (QR) code as exemplarily illustrated in FIG. 15A, or as a barcode as exemplarily illustrated in FIG. 15B. The identifier code 123 printed on the bin cover layer 104 identifies the medication organizer tray apparatus 100 exemplarily illustrated in FIGS. 1A-1C and FIGS. 2A-2B, is configured to allow verification of the presence of each medication bin 102 and the medications 112 in each medication bin 102 exemplarily illustrated in FIG. 1B, FIG. 9, and FIGS. 11A-11B. That is, the identifier code 123 stores information of the number of medication bins 102 assigned for the medication organizer tray apparatus 100 and the number and type of medications 112 accommodated in each medication bin 102. The identifier code 123 is further configured to provide links to secure web pages with healthcare recipient information. Information associated with the medication organizer tray apparatus 100 comprising, for example, a list of medication codes, an identifier (ID) of the medication organizer tray apparatus 100, an ID of a healthcare recipient to whom the medication organizer tray apparatus 100 is issued, etc., is embedded in the identifier code 123. A healthcare recipient or a healthcare provider can use, for example, a smartphone to scan the identifier code 123 and view the information embedded in the identifier code 123.

Figure 25:
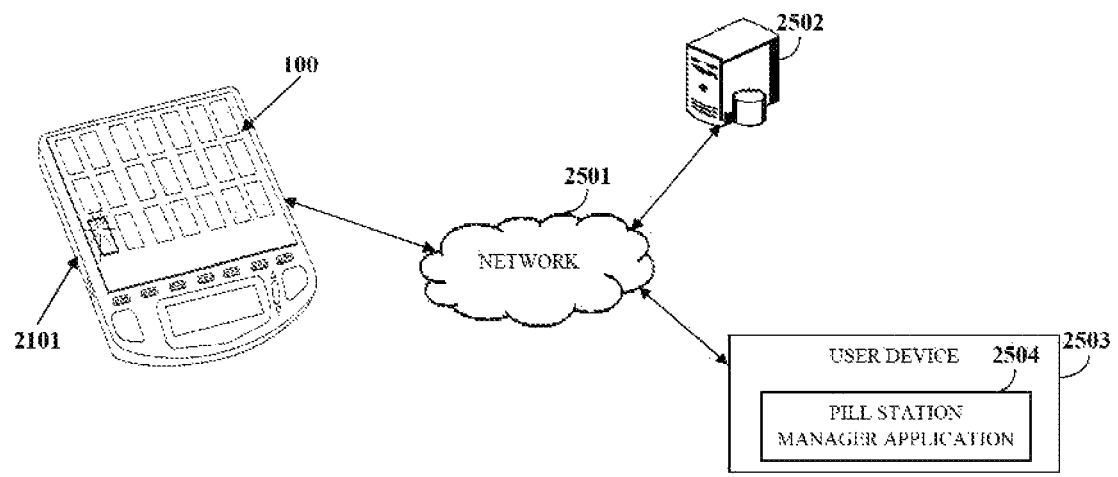
FIG. 25 exemplarily illustrates communication between the medication organizer tray apparatus inserted in a receptacle base, and a backend server and a user device via a network.

The identifier code 123 enables a pill station manager application 2504 configured as a client application executable by at least one processor on a user device 2503 exemplarily illustrated in FIG. 25 to verify that correct medication bins 102 of the medication organizer tray apparatus 100 contain the correct prescribed medications 112. The pill station manager application 2504 can be installed on the healthcare recipient's user device 2503 or the healthcare provider's user device 2503. The identifier code 123 is configured to be synchronized with the pill station manager application 2504 to confirm accuracy of alerts and messages being transmitted to a healthcare recipient. When the medication organizer tray apparatus 100 used by a healthcare recipient is connected to the receptacle base 2101 exemplarily illustrated in FIGS. 21A-21B and FIG. 22, the identifier code 123 that is scanned, for example, using the healthcare recipient's user device 2503 synchronizes with the pill station manager application 2504 to ensure that correct messages and alarms are delivered to the healthcare recipient. In an embodiment, the healthcare recipient can transmit the scanned identifier code 123 from the healthcare recipient's user device 2503 to the pill station manager application 2504 executable on the healthcare provider's user device 2503 for verification of information, messages, and alarms. In an embodiment, the bin cover layer 104 displays the identifier code 123, healthcare recipient information, etc. For example, a unique identifier (ID) such as a barcode or a QR code or a one-dimensional (1D) code or a two-dimensional (2D) code is printed on a packaging layer or the bin cover layer 104.

The identifier code 123 can be read by code reader devices, for example, smartphones and other ID readers for identifying the medication organizer tray apparatus 100 and confirming whether the correct medications 112 are filled in the medication bins 102. In an embodiment, the bin cover layer 104 displays a human readable ID for use in cases when code reader devices are not available. In another embodiment, another type of identifier code 123 is embedded in the QR code such that only the healthcare recipient's user device 2503 will be able to read the identifier code 123, decipher the content, match the identifiers, open a link, and display the content on the user device 2503. This type of identifier code 123 is useful when the healthcare recipient is located in an area where there is no network connectivity and the healthcare recipient requires a list of medications 112 stored in the medication organizer tray apparatus 100. In an embodiment, the identifier code 123 configured, for example, as a QR code links to a secure online application for verification of the healthcare recipient's information and the medical information.

FIG. 16A exemplarily illustrates a conductive circuit layer 107 of the medication organizer tray apparatus 100 exemplarily illustrated in FIGS. 1A-IC and FIGS. 2A-2B, showing conductive lines 108 and conductive pads 109. To preclude tampering of high priced and/or abusable medications 112 exemplarily illustrated in FIG. 1B, FIG. 9, and FIGS. 11A-11B, for example, pain killers, opioids, etc., by creation of incisions or cuts on the side surfaces 102e and 102f of the medication bin 102, and the lower surface 102a of the medication bin 102, the medication organizer tray apparatus 100 provides additional security via detection circuitry on the lower surface 104b of the bin cover layer 104 as exemplarily illustrated in FIG. 18A. The conductive lines 108 and the conductive pads 109 constitute the detection circuitry or the multi-layer conductive circuit of the conductive circuit layer 107. The conductive lines 108 of the conductive circuit layer 107 comprise, for example, conductive sensor circuit lines 108a, a common return line 108b, and a redundant circuit common return line 108c as exemplarily illustrated in FIGS. 16A-16C. The conductive pads 109 of the conductive circuit layer 107 comprise edge conductive pads 109a, medication bin conductive pads 109b, and a redundant conductive pad 109c as exemplarily illustrated in FIGS. 16A-16C.

Figure 18A:
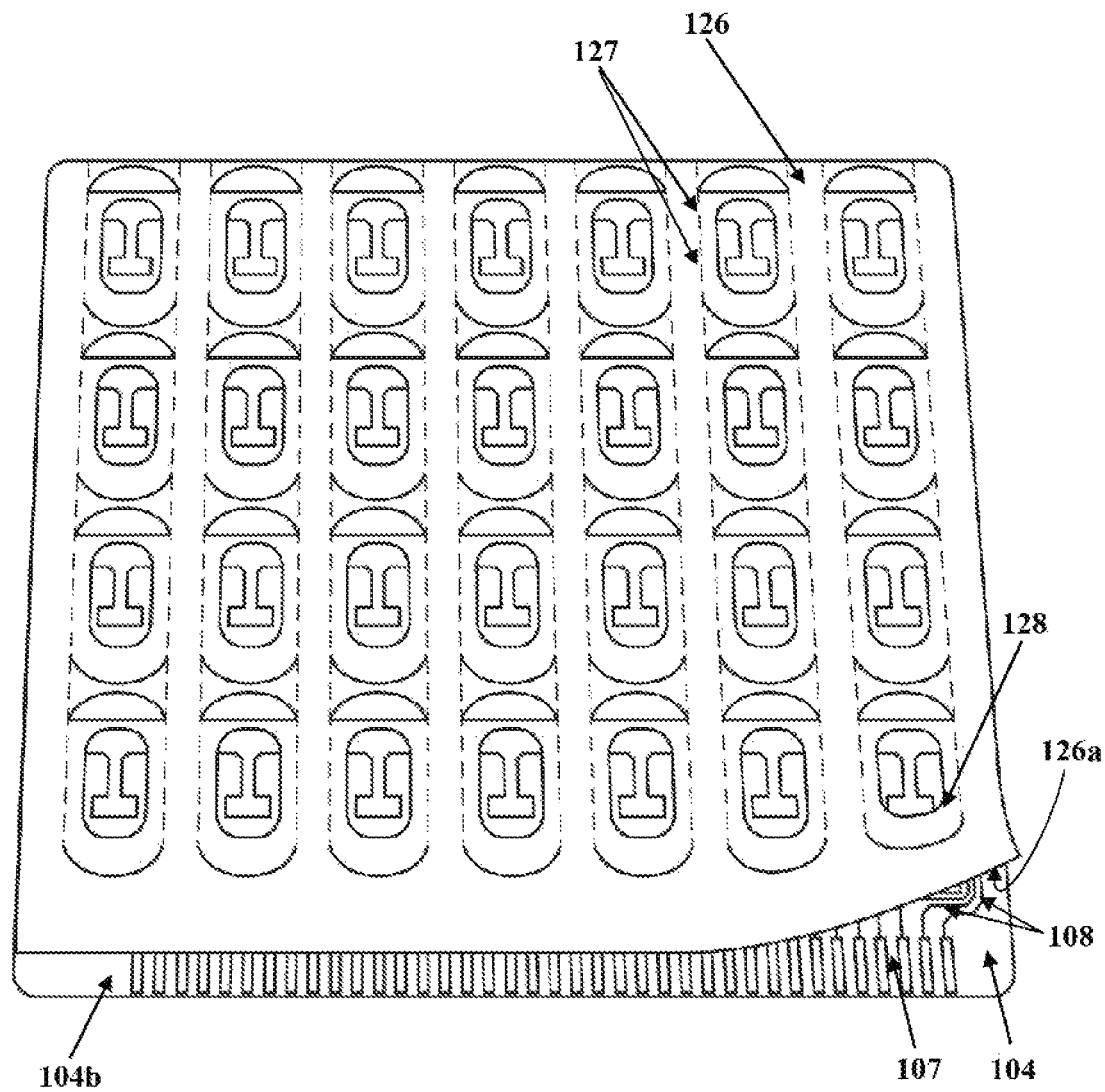
FIG. 18A exemplarily illustrates an adhesive protective paper layer removably attached to a lower surface of a bin cover layer of the medication organizer tray apparatus.

In an embodiment, the conductive circuit layer 107 is printed and embedded on the lower surface 104b of the bin cover layer 104 as exemplarily illustrated in FIG. 18A, and around each medication bin 102 and on the lower surface 102a of each medication bin 102 as exemplarily illustrated in FIG. 13. In an embodiment, the conductive lines 108 of the conductive circuit layer 107 running along one or more of the lower surface 104b of the bin cover layer 104, around each medication bin 102, and the lower surface 102a of each medication bin 102 are printed using one or more of multiple conductive print technologies to allow etching of complex electric circuits without causing short circuit issues. In another embodiment, the conductive circuit layer 107 is printed using conductive ink. In an embodiment, the conductive ink is an invisible ink. In an embodiment, the conductive ink is printed on each medication bin 102. In another embodiment, the conductive lines 108 of the conductive circuit layer 107 running along one or more of the lower surface 104b of the bin cover layer 104, around each medication bin 102, and the lower surface 102a of each medication bin 102 are created by applying an electrically conductive material, for example, copper on one or more of the lower surface 104b of the bin cover layer 104, around the medication bins 102 exemplarily illustrated in FIGS. 11A-11B, and the lower surface 102a of the medication bins 102, and removing excess of the electrically conductive material by an etching process or using chemicals such that only the conductive lines 108 remain. In an embodiment, the conductive lines 108 are color coded such that the conductive lines 108 appear as a design element of the medication organizer tray apparatus 100 and enhance the aesthetics of the medication organizer tray apparatus 100.

The multi-layer conductive circuit of the conductive circuit layer 107 is configured to trip when one or more of the medication bins 102 are removed from the support frame 101 exemplarily illustrated in FIGS. 1A-7. The multi-layer conductive circuit comprises the conductive sensor circuit lines 108a, the conductive connection pads, that is, the edge conductive pads 109a, the medication bin conductive pads 109b, the common return lines 108b, the redundant circuit common return line 108c, the redundant conductive pad 109c, and additional conductive sensor circuit lines 108d and 108e exemplarily illustrated in FIG. 16B. In an embodiment, the edges 107a and 107b of the conductive circuit layer 107 form large conductive regions as exemplarily illustrated in FIGS. 16A-16C.

The conductive sensor circuit lines 108a of the conductive circuit layer 107 are signal lines for each medication bin 102. The conductive sensor circuit lines 108a ensure connectivity of each medication bin 102 with the conductive circuit layer 107. Each medication bin 102 has a closed loop circuit comprising a conductive sensor circuit line 108a and common return lines 108b passing through the edge conductive pads 109a. The common return lines 108b are configured for one or more medication bins 102. The common return lines 108b increase circuit reliability against incorrect registration of the conductive sensor circuit line 108a of each medication bin 102 in the conductive circuit layer 107. Sharing of common return lines 108b increases circuit reliability against incorrect registration of the conductive sensor circuit line 108a, for example, while printing, deposition, etc., or tearing beyond medication bin perforations 110 exemplarily illustrated in FIG. 1B, FIG. 4A, FIG. 5, FIG. 7, and FIG. 9. Since each medication bin 102 is independent from another medication bin 102 of the medication organizer tray apparatus 100, single or multiple line breaks in the conductive sensor circuit lines 108a of the conductive circuit layer 107 representing removal of single or multiple medication bins 102 from the support frame 101 of the medication organizer tray apparatus 100 can be detected simultaneously.

The edge conductive pads 109a are configured for each conductive sensor circuit line 108a of each medication bin 102. The edge conductive pads 109a ensure connectivity to the detection circuitry 1601 exemplarily illustrated in FIG. 16C, of the receptacle base 2101 exemplarily illustrated in FIGS. 21A-21B and FIG. 22. The edge conductive pads 109a electrically communicate with one or more base conductive pads 1604 of the receptacle base 2101 as exemplarily illustrated in FIG. 16C, to enable detection of removal of each medication bin 102 from the support frame 101 and detection of tampering of the medication bins 102. In an embodiment, the edge conductive pads 109a are formed by depositing a larger amount of conductive ink in certain regions of the bin cover layer 104. The conductive sensor circuit lines 108a are initiated and terminated through the edge conductive pads 109a which are larger in size to maximize electrical connectivity in the medication organizer tray apparatus 100. In an embodiment, the medication bin conductive pads 109b detect a medication bin 102 being opened. The medication bin conductive pads 109b are configured as large and wide lines for each of the medication bins 102 and maintain their conductive integrity even after the perforations 105 of the bin cover layer 104 pass through the medication bin conductive pads 109b. The medication bin conductive pads 109b maintain conductive integrity of the conductive sensor circuit line 108a of each medication bin 102 when perforations 105 positioned at predefined areas on the bin cover layer 104 cut through the conductive sensor circuit line 108a.

To further strengthen connectivity and protection against premature tearing during removal of the medication bins 102, a redundant circuit common return line 108c is provided in the conductive circuit layer 107. The redundant circuit common return line 108c is positioned on a periphery 107c of the conductive circuit layer 107 and terminates on a different terminating edge conductive pad 109a as exemplarily illustrated in FIGS. 16A-16C. The redundant circuit common return line 108c ensures electrical conductivity in the conductive circuit layer 107 if a common return line 108b of the multi-layer conductive circuit is compromised. All conductive circuit layers 107 can share one redundant circuit common return line 108c and reduce the number of overall edge conductive pads 109a. For example, the common return lines 108b of four day medication bins 102 comprising medications 112 exemplarily illustrated in FIG. 1B, to be consumed, for example, on a Monday, share a redundant circuit common return line 108c as exemplarily illustrated in FIGS. 16A-16C. The common return lines 108b for each day's medication bin 102 share the redundant circuit common return line 108c. The redundant conductive pad 109e is configured for the redundant circuit common return line 108c. The redundant conductive pad 109c of the redundant circuit common return line 108c connects to one or more of the base conductive pads 1604 of the receptacle base 2101 as exemplarily illustrated in FIG. 16C.

FIG. 16B exemplarily illustrates an embodiment of the conductive circuit layer 107 of the medication organizer tray apparatus 100 exemplarily illustrated in FIGS. 1A-1C and FIGS. 2A-2B, showing conductive sensor circuit lines 108d and 108e of different patterns. In an embodiment, the conductive circuit layer 107 comprises additional conductive sensor circuit lines 108d and 108e of multiple patterns for the medication bins 102 exemplarily illustrated in FIGS. 11A-11B. The additional conductive sensor circuit lines 108d and 108e are configured to communicate with the receptacle base 2101 exemplarily illustrated in FIGS. 21A-21B and FIG. 22, to detect tampering of the medication bins 102 and the bin cover layer 104 exemplarily illustrated in FIGS. 1A-1B. In an embodiment, the additional conductive sensor circuit lines 108d and 108e are configured in different shapes as exemplarily illustrated in FIG. 16B, to prevent tampering by creation of cuts or incisions in the medication bins 102 to remove the medications 112 exemplarily illustrated in FIGS. 11A-11B. In an embodiment, additional redundant circuitry formed by the additional conductive sensor circuit lines 108d and 108e may be embedded on the bin cover layer 104 in case one conductive circuit layer 107 is compromised. A second conductive sensor circuit line, for example, 108e is provided for additional circuit connections as a backup as exemplarily illustrated in FIG. 16B. The conductive circuit layer 107 is configured with additional conductive sensor circuit lines 108d and 108e or circuit connections as backups, thereby forming complex patterns of conductive lines 108, for example, loops on predefined areas of the bin cover layer 104 that cover the openings 117 of the medication bins 102 exemplarily illustrated in FIG. 7, FIG. 10, FIG. 11A, and FIG. 18B. These additional conductive sensor circuit lines 108d and 108e and circuit connections are provided to preclude patients from stealing medications 112, by creating a small incision or a cut in the medication bin 102 and taking the medications 112 out. This configuration of the conductive circuit layer 107 allows detection of any method of accessing the medication bins 102, for example, removal of the medication bins 102 from the support frame 101 exemplarily illustrated in FIGS. 1A-7, as well as tampering of the bin cover layer 104 in any manner, for example, by puncturing the bin cover layer 104 and removing the medications 112 from the upper surface 102c of the medication bin 102 exemplarily illustrated in FIG. 10 and FIGS. 12-13. This configuration of the conductive circuit layer 107 allows detection when a person accesses the medication bin 102 by removing the medication bin 102 from the support frame 101 or by removing the medications 112 by puncturing the bin cover layer 104 at the upper surface 102c of the medication bin 102.

Figure 21A:
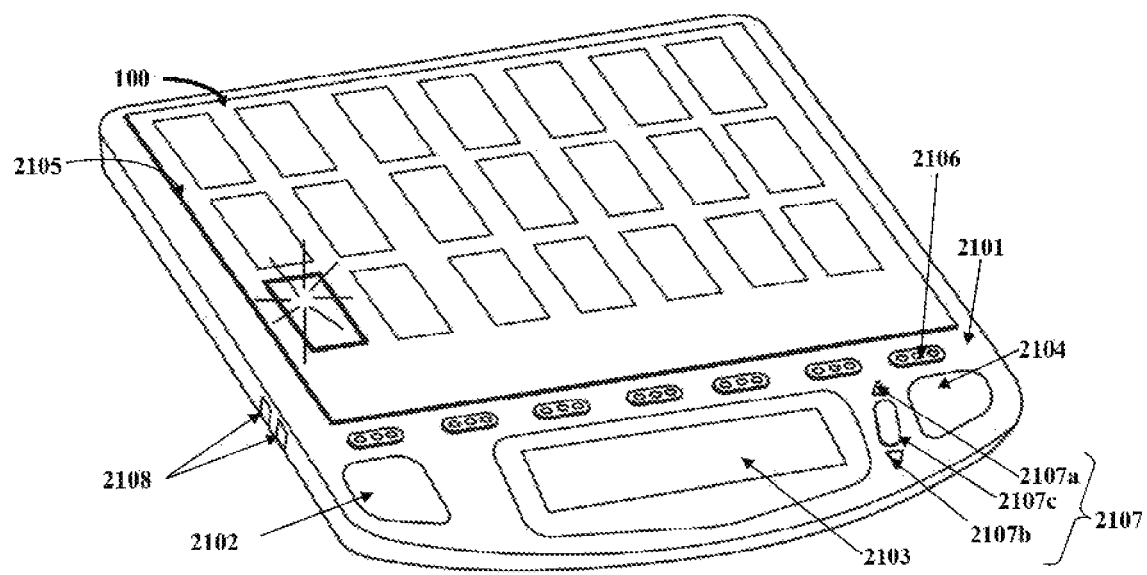
FIGS. 21A-21B exemplarily illustrate different views showing the medication organizer tray apparatus inserted into a receptacle base.
Figure 21B:
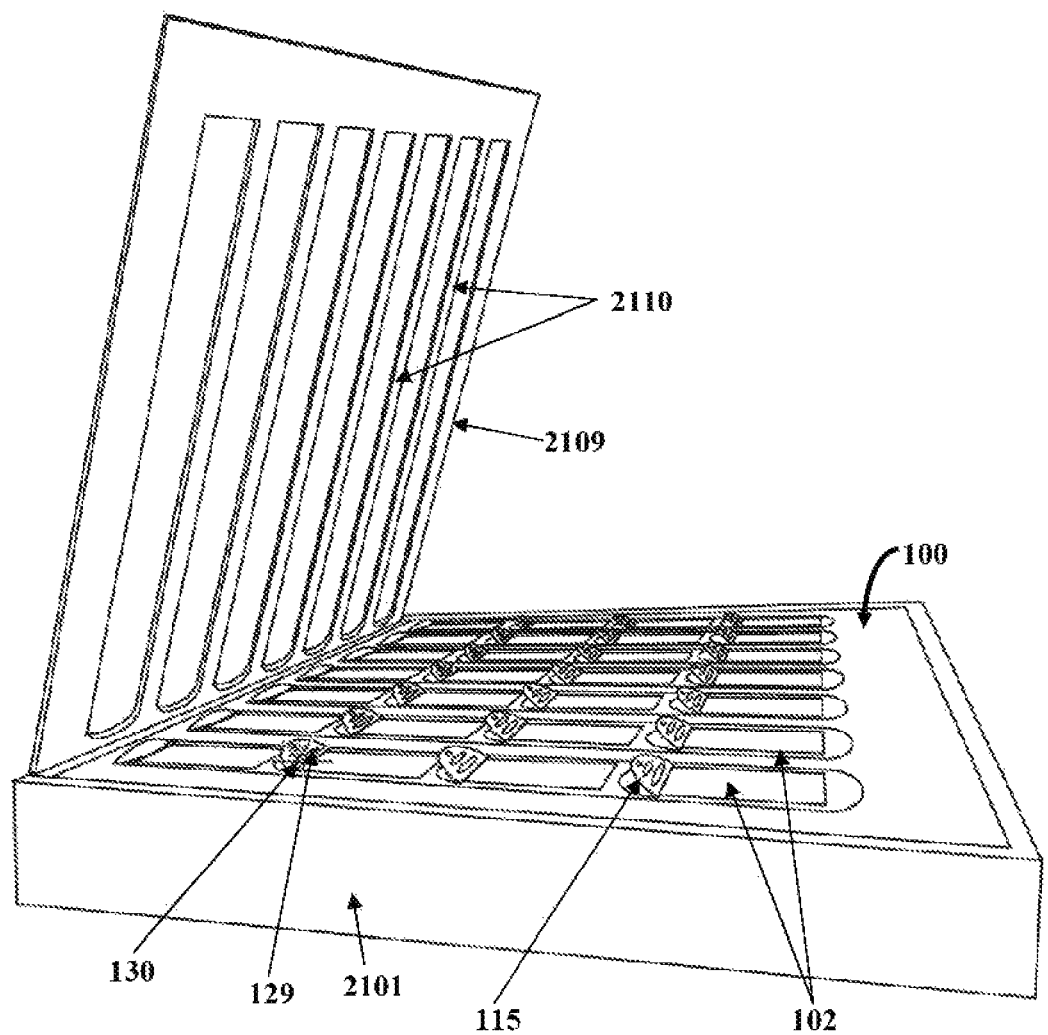
Figure 22:
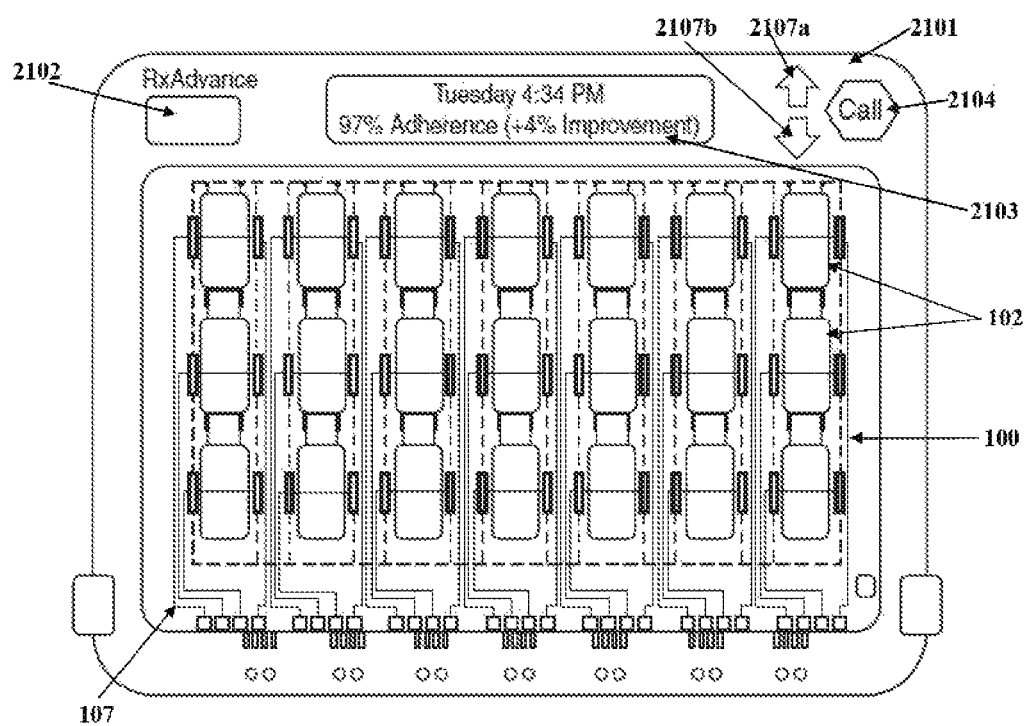
FIG. 22 exemplarily illustrates a top plan view of an embodiment of a receptacle base accommodating the medication organizer tray apparatus.

FIG. 16C exemplarily illustrates communication between the conductive circuit layer 107 of the medication organizer tray apparatus 100 exemplarily illustrated in FIGS. 1A-1C and FIGS. 2A-2B, and detection circuitry 1601 of the receptacle base 2101 exemplarily illustrated in FIGS. 21A-21B and FIG. 22. The conductive circuit layer 107 is printed and embedded in the medication organizer tray apparatus 100 such that when one or more of the medication bins 102 containing medications 112 exemplarily illustrated in FIGS. 8-9, that are scheduled to be consumed by a healthcare recipient in a day are removed, the conductive circuit layer 107 is tripped. The tripped conductive circuit layer 107 is detected by the detection circuitry 1601 of the receptacle base 2101. The conductive circuit layer 107 communicates with the receptacle base 2101 to enable detection of removal of each medication bin 102 from the support frame 101 and detection of tampering of the medication bins 102. As exemplarily illustrated in FIG. 16C, the detection circuitry 1601 of the receptacle base 2101 comprises a detection circuitry processing component 1602 and an electronic identification processing component 1603. The detection circuitry processing component 1602 is configured to communicate with the conductive circuit layer 107 of the medication organizer tray apparatus 100. The electronic identification processing component 1603 is configured to communicate with the electronic identification component 103 of the medication organizer tray apparatus 100. The conductive pads 109 of the conductive circuit layer 107 comprising the edge conductive pads 109a and the redundant conductive pad 109e positioned on the lower surface 104b of the bin cover layer 104 exemplarily illustrated in FIGS. 1A-1B and FIG. 18B, electrically connect to connector pins 1602a that extend from the detection circuitry processing component 1602 of the receptacle base 2101 via multiple base conductive pads 1604a and 1604b of the receptacle base 2101. The electronic identification component pads 125 positioned on the lower surface 104b of the bin cover layer 104 electrically connect to connector pins 1603a that extend from the electronic identification processing component 1603 of the receptacle base 2101 via base conductive pads 1604e of the receptacle base 2101. The base conductive pads 1604 comprise base edge conductive pads 1604a, a base redundant conductive pad 1604b, and base identification component pads 1604c. Each base edge conductive pad 1604a is aligned with each edge conductive pad 109a. Each base redundant conductive pad 1604b is aligned with the redundant conductive pad 109c. Each electronic identification component pad 125 is aligned with each base identification component pad 1604c. These alignments of the conductive pads 109 of the conductive circuit layer 107 with the base conductive pads 1604 make an electrical connection between the receptacle base 2101 and the medication organizer tray apparatus 100 as exemplarily illustrated in FIG. 16C.

In an embodiment, the detection circuitry processing component 1602 of the receptacle base 2101 comprises, for example, about 35 connector pins 1602a electrically connected to the edge conductive pads 109a of the conductive circuit layer 107 via about 35 base edge conductive pads 1604a. In an embodiment, the detection circuitry processing component 1602 provides, for example, about 5 connector pins 1602a and base edge conductive pads 1604a for making electrical connection to the medication bins 102 of the medication organizer tray apparatus 100. The conductive sensor circuit lines 108a running along the lower surface 104b of the bin cover layer 104, around each medication bin 102, and on the lower surface 102a of each medication bin 102, via the edge conductive pads 109a, connect to the connector pins 1602a of the detection circuitry processing component 1602 via the base edge conductive pads 1604a. The redundant circuit common return line 108c, via the redundant conductive pad 109c of the conductive circuit layer 107, connects to the base redundant conductive pad 1604b of the detection circuitry processing component 1602. The electronic identification processing component 1603 of the detection circuitry 1601 comprises, for example, about 4 base identification component pads 1604c extending from the connector pins 1603a and configured to align with and electrically connect to connector pins 124 of the electronic identification component 103 via electronic identification component pads 125 of the medication organizer tray apparatus 100 as exemplarily illustrated in FIG. 16C.

The conductive sensor circuit lines 108a connect to the edge conductive pads 109a. The edge conductive pads 109a connect to the detection circuitry 1601 of the receptacle base 2101 as exemplarily illustrated in FIG. 16C. Each time a medication bin 102 is opened, the conductive sensor circuit line 108a corresponding to that medication bin 102 is tripped, thereby resulting in a tripped conductive circuit layer 107 on the medication organizer tray apparatus 100. The detection circuitry 1601 of the receptacle base 2101 that is connected to the edge conductive pads 109a of the medication organizer tray apparatus 100 senses the tripped conductive sensor circuit lines 108a and intact conductive sensor circuit lines 108a of the conductive circuit layer 107. A conductive circuit layer 107 which is broken at times and intact at other times indicates tampering of the medication bins 102, for example, when a healthcare recipient may have tried to open and close the medication bin 102, but failed to make a full connection of the conductive circuit layer 107 due to improper removal and/or insertion of the medication bin 102 from the support frame 101 exemplarily illustrated in FIGS. 1A-7. When a healthcare recipient inserts the medication organizer tray apparatus 100 in the receptacle base 2101, the edge conductive pads 109a which are positioned on the lower surface 104b of the bin cover layer 104 make physical contact with the base edge conductive pads 1604a of the detection circuitry 1601 embedded in the receptacle base 2101. The positions of the base conductive pads 1604 match the positions of each of the edge conductive pads 109a, the redundant conductive pad 109c, and the electronic identification component pads 125. The physical contact makes the electrical connection for signals which connect the detection circuitry 1601 of the receptacle base 2101 to the conductive circuit layer 107 of the medication organizer tray apparatus 100.

The detection circuitry 1601 of the receptacle base 2101 collects information associated with detection of a break in the conductive sensor circuit lines 108a of the conductive circuit layer 107. The collected information comprises, for example, a time and a date of the break in the conductive sensor circuit lines 108a, the medication bin 102 that is removed from the support frame 101, etc. The receptacle base 2101 transmits the collected information to a backend server 2502 via a network 2501 exemplarily illustrated in FIG. 25. The backend server 2502 receives and uses the collected information to monitor compliance of the healthcare recipients with a medication regimen. When a patient has consumed all the prescribed medications 112 contained in the medication bins 102 of the medication organization tray apparatus 100 based on dose time information stored in the electronic identification component 103, the receptacle base 2101 further transmits the collected medication adherence information to the backend server 2502 via the network 2501. In an embodiment, the detection circuitry 1601 of the receptacle base 2101 transmits the collected information to the electronic identification component 103. For example, in cases when the patient using the medication organization tray apparatus 100 has no connectivity to the backend server 2502 for example, via the internet, a cell phone with internet connectivity, Ethernet, etc., the receptacle base 2101 stores the collected medication adherence information in the electronic identification component 103, and the patient can remove and ship the electronic identification component 103, for example, to a company, a pharmacy, or a medical entity for checking medication adherence. The pharmacy can directly access the medication adherence information stored in the electronic identification component 103, that is collected from the receptacle base 2101.

In an embodiment, the conductive circuit layer 107 is electrically connected to a power source for receiving minimal power at predetermined time intervals to enable detection of a break in the conductive circuit layer 107, in electric communication with the receptacle base 2101, when one or more of the medication bins 102 are removed from the support frame 101. In this embodiment, when the medication bin 102 is removed from the support frame 101 of the medication organizer tray apparatus 100, the detection circuitry 1601 of the receptacle base 2101 detects removal of the medication bins 102 as the circuit connection is broken, at predetermined time intervals. In another embodiment, the conductive circuit layer 107 is electrically connected to a power source for receiving a constant power supply of minimal magnitude to enable detection of a break in the conductive circuit layer 107, in communication with the receptacle base 2101, when one or more of the medication bins 102 are removed from the support frame 101. In this embodiment, the detection circuitry 1601 of the receptacle base 2101 dynamically detects removal of the medication bins 102 as the circuit connection is broken, when the medication bin 102 is removed from the support frame 101 of the medication organizer tray apparatus 100.

In an embodiment, a power drop in the conductive sensor circuit lines 108a of the conductive circuit layer 107 can be minimized, for example, reduced to zero, except for a predetermined time interval such as a few seconds at the time of sensing removal of each medication bin 102 from the support frame 101 and/or tampering of the medication bins 102. High power drop across the medication organizer tray apparatus 100 can heat up the conductive circuit layer 107. In an embodiment, a break in the conductive circuit layer 107 of the medication organizer tray apparatus 100 is detected, when a small current generating a generally small power, for example, of about 30 milliwatts (mW) is passed through the conductive sensor circuit lines 108a and the continuity of the generated power along the conductive sensor circuit lines 108a is broken. In another embodiment, the conductive circuit layer 107 is isolated with no current flowing through the conductive sensor circuit lines 108a; hence no power flows across the conductive sensor circuit lines 108a. In this embodiment, the detection circuitry 1601 of the receptacle base 2101 exemplarily illustrated in FIG. 16C, periodically polls the medication organizer tray apparatus 100 at predetermined time intervals. For example, the detection circuitry 1601 of the receptacle base 2101 polls the medication organizer tray apparatus 100 at a polling time of about 15 minutes. The conductive sensor circuit lines 108a of the medication organizer tray apparatus 100 are electrically connected at the polling time. When the conductive sensor circuit lines 108a are electrically connected, then a small amount of current is passed through the conductive sensor circuit lines 108a to detect open and close conductive sensor circuit lines 108a.

FIGS. 17A-17B exemplarily illustrate embodiments of the electronic identification component 103 of the medication organizer tray apparatus 100 exemplarily illustrated in FIGS. 1A-1C and FIGS. 2A-2B. The electronic identification component 103 is configured as an embedded identifier chip or an integrated circuit chip. In an embodiment, the electronic identification component 103 is, for example, a security and identifier (ID) chip or a hardwired chip embedded in the support frame 101 of the medication organizer tray apparatus 100 exemplarily illustrated in FIGS. 1A-IC. The electronic identification component 103 is, for example, an active chip or a passive chip or a tag and operates using one or more wired modes of communication, for example, via direct contact using cables or one or more wireless modes of communication, for example, mobile Wi-Fi® (MiFi®) of Novatel Wireless, Inc., radio frequency identification (RFID), etc. The electronic identification component 103 configured, for example, as an RFID sensor or a MiFi® sensor stores medication adherence information comprising, for example, one or more of a serial identifier that matches a healthcare recipient identifier, information to coordinate medical activities, network identifiers and passwords, dosage times, wellness instructions for providing behavioral support for ensuring medication adherence by a healthcare recipient, messages, calendar information, information associated with removal of each medication bin 102 from the support frame 101 exemplarily illustrated in FIGS. 1A-1C, and tampering of the medication bins 102, etc. The electronic identification component 103 also stores identifiers of messages for the receptacle base 2101 exemplarily illustrated in FIGS. 21A-21B and FIG. 22, to play at a specific time.

In an embodiment, the electronic identification component 103 is installed or embedded into the support frame 101 via a sticker 1701 that is placed on the support frame 101 of the medication organizer tray apparatus 100. In an embodiment, the sticker 1701 is made of plastic material. In an embodiment, a rear surface 1701a of the sticker 1701 is a conductive surface comprising conductive lines 1704 and conductive pads 1703 configured to electrically connect the electronic identification component 103 to the receptacle base 2101. In an embodiment, the conductive pads 1703 on the sticker 1701 connect through an adhesive such as glue or other means to the electronic identification component pads 125 of the conductive circuit layer 107 exemplarily illustrated in FIGS. 16A-16C, which are etched and exposed on the medication organizer tray apparatus 100. In an example, the electronic identification component 103 is placed on the sticker 1701 during a manufacturing process of the electronic identification component 103, and is tested and programmed in a laboratory. Conductive ink is then applied on the connector pins 124 of the electronic identification component 103. Large conductive pads 1703 are configured on the sticker 1701 to ensure appropriate alignment of the conductive pads 1703 to the electronic identification component pads 125 of the conductive circuit layer 107 of the medication organizer tray apparatus 100. The electronic identification component 103 connects to the detection circuitry 1601 exemplarily illustrated in FIG. 16C, of the receptacle base 2101 via the conductive pads 1703 of the sticker 1701 and validates the medication organizer tray apparatus 100 and healthcare recipient information.

The electronic identification component 103 comprises three or four connector pins 124 that connect to the conductive pads 1703 depending on the type of connector pins 124. In an embodiment, the electronic identification component 103 comprises four connector pins 124 as exemplarily illustrated in FIG. 17A. The four connector pins 124 of the electronic identification component 103 represent connections comprising, for example, two control lines 124a and 124c, a power line 124b, and a ground line 124d. In another embodiment, the electronic identification component 103 comprises three connector pins 124 as exemplarily illustrated in FIG. 17B. In this embodiment, the connector pins 124 of the electronic identification component 103 represent connections comprising, for example, a control line 124a, a power line 124b, and a ground line 124d as exemplarily illustrated in FIG. 17B. The ground line 124d is a return line which can connect, for example, to a ground line of a battery or a ground line of the receptacle base 2101. The control line 124a and 124c are signal lines through which the electronic identification component 103 exchanges information comprising, for example, an identifier code 123 exemplarily illustrated in FIGS. 15A-15B, of the medication organizer tray apparatus 100, opening and/or closing of the conductive circuit layer 107, time of opening and/or closing of the conductive circuit layer 107, etc., with the receptacle base 2101. The control line 124a and 124c are used to program and load medication adherence information in the electronic identification component 103. The rear conductive surface 1701a of the sticker 1701 comprises conductive lines 1704 that are connected to a series of conductive pads 125 of the electronic identification component 103 via matching conductive pads 1703 of the sticker 1701. In an embodiment, the electronic identification component 103 receives power from different power sources through the power line 124b. The electronic identification component 103 comprises basic information when placed via the sticker 1701. In an embodiment, the medication organizer tray apparatus 100 further comprises placement alignment markers (not shown) that enable proper placement of the sticker 1701 and the edge conductive pads 109a in the medication organizer tray apparatus 100. For example, the placement location of the sticker 1701 is printed or indented on the medication organizer tray apparatus 100 to ensure that the sticker 1701 with the electronic identification component 103 is placed accurately in the receptacle 116 configured in the support frame 101 exemplarily illustrated in FIG. 4A, and that a connection has been made between the electronic identification component pads 125 and the base identification component conductive pads 1604c of the electronic identification processing component 1603 of the detection circuitry 1601 of the receptacle base 2101.

When the medication organizer tray apparatus 100 is inserted in the receptacle base 2101, the receptacle base 2101 validates healthcare recipient information, matches day time, updates dosage instructions, updates messages, updates wellness information, updates a type of security circuitry, etc., based on the medication adherence information stored in the electronic identification component 103. The electronic identification component 103 shares the stored medication adherence information with a healthcare recipient to whom the medication organizer tray apparatus 100 is assigned. For example, the healthcare recipient can connect the electronic identification component 103, for example, to a computing device to access the stored medication adherence information. In an embodiment, the electronic identification component 103 carries a specific security type identifier configuration. In another embodiment, the security type identifier configuration is downloaded from the pill station manager application 2504 exemplarily illustrated in FIG. 25, when the medication organizer tray apparatus 100 is inserted in the receptacle base 2101. The electronic identification component 103 confirms the healthcare recipient identifier of the healthcare recipient. The electronic identification component 103 carries additional information to confirm that the right healthcare recipient is getting the right medication organizer tray apparatus 100 for the right week and provides information that offers additional behavioral support and encouragement to the healthcare recipient to encourage the healthcare recipient to adhere to the medications 112 exemplarily illustrated in FIG. 1B, FIG. 9, and FIGS. 11A-11B, and his/her wellness regimen.

In an embodiment, the electronic identification component 103 comprises a power source 1705, for example, a battery configured to power the electronic identification component 103. In this embodiment, the battery can be placed on the sticker 1701. In another embodiment, the electronic identification component 103 receives power from a power source (not shown) of the receptacle base 2101. The power source of the receptacle base 2101 connects to the electronic identification component pads 125 in the medication organizer tray apparatus 100 and powers the electronic identification component 103 on the medication organizer tray apparatus 100. Once the electronic identification component 103 receives power, the electronic identification component 103 is activated in a programming mode to store, for example, alarm information, information associated with a healthcare recipient identifier, etc. In another embodiment, the electronic identification component 103 comprises a light energy collector 1702 for powering the electronic identification component 103. When a light source illuminates the medication organizer tray apparatus 100, light energy from the light source provides a primary or a backup power source for the electronic identification component 103. If a healthcare recipient inserts the medication organizer tray apparatus 100 in the receptacle base 2101 that is not powered, the light energy collector 1702 can power up the electronic identification component 103 and turn on, for example, a green light or a red light to indicate whether a healthcare recipient identifier of the medication organizer tray apparatus 100 matches a healthcare recipient identifier of the receptacle base 2101. In an embodiment, the receptacle base 2101 comprises a hard-wired chip (not shown) configured to connect to the electronic identification component 103 positioned in the support frame 101 of the medication organizer tray apparatus 100 and also to power the electronic identification component 103. The electronic identification component 103 can then confirm that an identifier of the medication organizer tray apparatus 100 matches an identifier of the receptacle base 2101 to ensure that a right healthcare recipient receives the right medication organizer tray apparatus 100 assigned to him/her.

The electronic identification component 103 further comprises a light emitting diode (not shown) which is activated, when the electronic identification component 103 is connected to the support frame 101 and when the medication organizer tray apparatus 100 is inserted into the receptacle base 2101. The light emitting diode confirms that the connection has been made between the electronic identification component 103 and the support frame 101 of the medication organizer tray apparatus 100, and/or between the electronic identification component 103 and the receptacle base 2101, when the medication organizer tray apparatus 100 is placed in the receptacle base 2101. In an embodiment, if the electronic identification component 103 of the medication organizer tray apparatus 100 is passive then, when the medication organizer tray apparatus 100 is inserted into the receptacle base 2101, an indication such as a beep via a loudspeaker 2102, a light, or a message on a liquid crystal display (LCD) screen 2103 of the receptacle base 2101 exemplarily illustrated in FIG. 21A and FIG. 22, indicates that the connections are intact.

FIG. 18A exemplarily illustrates an adhesive protective paper layer 126 removably attached to the lower surface 104b of the bin cover layer 104 of the medication organizer tray apparatus 100 exemplarily illustrated in FIGS. 1A-1C and FIGS. 2A-2B. The adhesive protective paper layer 126 forms the third component layer 303 of the medication organizer tray apparatus 100 as exemplarily illustrated in FIG. 3. The adhesive protective paper layer 126 comprises an adhesive 126a that is selectively applied on the lower surface 104b of the bin cover layer 104. The adhesive protective paper layer 126 further comprises perforations 127 and openings 128 that mirror perforations 110 and openings 117 of the medication bins 102 respectively, as exemplarily illustrated in FIG. 18B.

Figure 18B:
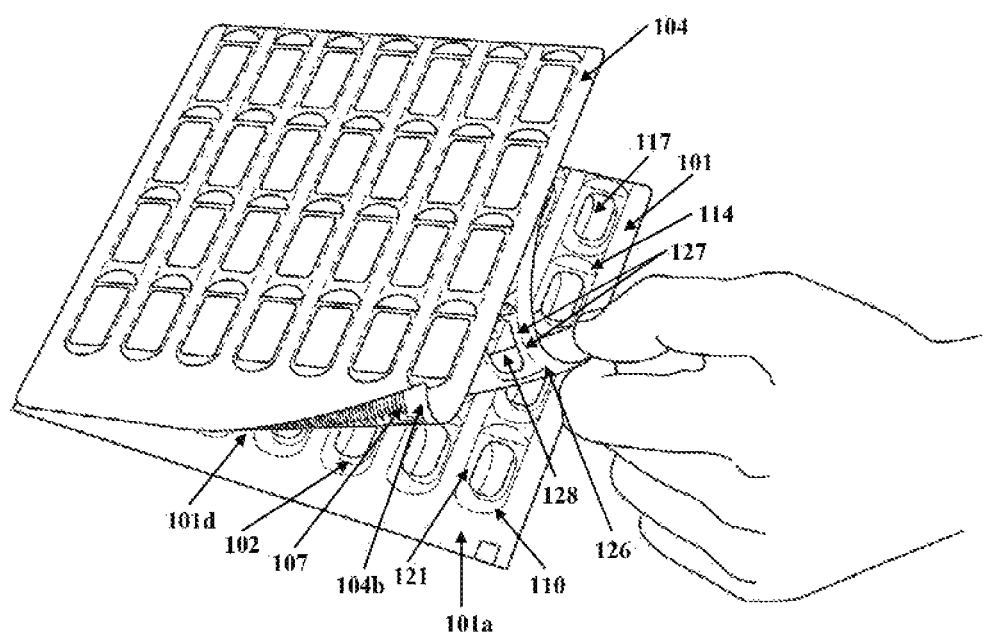
FIG. 18B exemplarily illustrates removal of the adhesive protective paper layer from the lower surface of the bin cover layer to allow attachment of the lower surface of the bin cover layer to an upper surface of a support frame.

FIG. 18B exemplarily illustrates removal of the adhesive protective paper layer 126 from the lower surface 104b of the bin cover layer 104 to allow attachment of the lower surface 104b of the bin cover layer 104 to the upper surface 101a of the support frame 101. The adhesive protective paper layer 126 comprising the adhesive 126a is removably attached to the lower surface 104b of the bin cover layer 104. After the medications 112 exemplarily illustrated in FIG. 1B, are loaded in the medication bins 102 of the medication organizer tray apparatus 100 exemplarily illustrated in FIGS. 1A-1C and FIGS. 2A-2B, the adhesive protective paper layer 126 is removed from the lower surface 104b of the bin cover layer 104. The bin cover layer 104 having the selectively applied adhesive 126a exposed on the lower surface 104b of the bin cover layer 104 is then removably attached to the upper surface 101a of the support frame 101. When the adhesive protective paper layer 126 is removed from the lower surface 104b of the bin cover layer 104, the adhesive 126a of the adhesive protective paper layer 126 is left exposed on the lower surface 104b of the bin cover layer 104. When the adhesive protective paper layer 126 is removed, the exposed adhesive 126a on the lower surface 104b of the bin cover layer 104 is used to attach the lower surface 104b the bin cover layer 104 to the upper surface 101a of the support frame 101. The exposed adhesive 126a is selectively applied on the upper surface 101a of the support frame 101 to match an outline of the lips 121 of the medication bins 102 and surfaces 101d surrounding the outer edges 111a of the apertures 111 of the support frame 101. The adhesive 126a is not applied on the cut edges 114 of the medication bins 102 and hence allows peeling and removal of the customized bin labels 106 exemplarily illustrated in FIG. 1A, FIGS. 2A-2B, FIGS. 8-9, and FIGS. 14A-14D, from the medication bins 102. The adhesive strength provided by the adhesive 126a of the adhesive protective paper layer 126 is calibrated to allow easy and clean removal of the customized bin labels 106 from the medication bins 102 and for removing medications 112 from the medication bins 102.

FIGS. 19A-19D exemplarily illustrate different configurations for organizing medications 112 in the medication organizer tray apparatus 100 exemplarily illustrated in FIGS. 1A-IC and FIGS. 2A-2B. FIGS. 19A-19D exemplarily illustrate multiple weekly configurations of organizing medications 112 in the medication organizer tray apparatus 100. The medication organizer tray apparatus 100 can be customized for holding different types of medications 112 and medication dosages. In an example, up to 4 pre-filled medication organizer tray apparatuses 100 a month or weekly pre-filled medication organizer tray apparatuses 100 are sent to a healthcare recipient as per his/her prescription with medical information printed on the customized bin labels 106 exemplarily illustrated in FIG. 1A, FIGS. 2A-2B, FIGS. 8-9, and FIGS. 14A-14D. In an embodiment, the medication organizer tray apparatus 100 is configured for holding a daily dosage, a weekly dosage for 7, 14, 21, or 28 days, or a monthly dosage of medications 112.

Figure 19A:
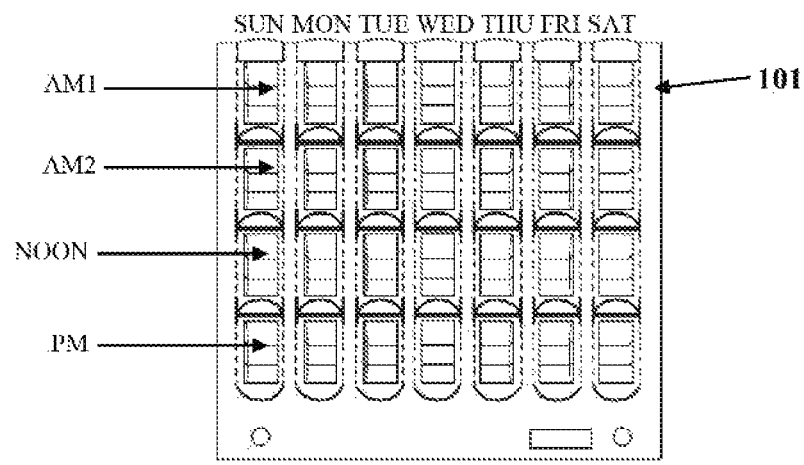
FIGS. 19A-19D exemplarily illustrate different configurations for organizing medications in the medication organizer tray apparatus.

FIG. 19A exemplarily illustrates a 4×7 medication organizer tray apparatus 100 containing a medication dosage to be taken 4 times a day, each day of the week. The first two rows of the 4×7 medication organizer tray apparatus 100 contain medications 112 that are to be taken at different times during the day, every day of the week. The third row contains medications 112 that are to be taken at noon time, every day of the week. The fourth row of the 4×7 medication organizer tray apparatus 100 contains medications 112 that are to be taken in the evening, every day of the week.

Figure 19B:
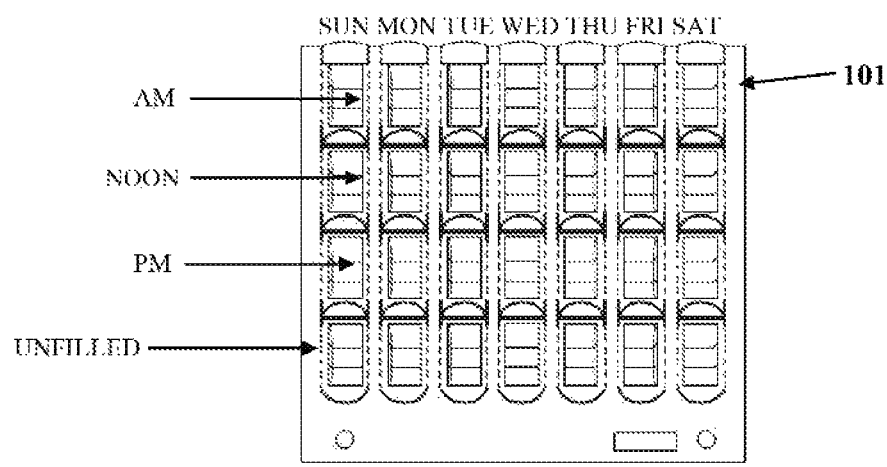

FIG. 19B exemplarily illustrates a 4×7 medication organizer tray apparatus 100 containing a medication dosage to be taken 3 times a day, each day of the week. The first row of the 4×7 medication organizer tray apparatus 100 contains medications 112 that are to be taken in the morning, every day of the week. The second row of the 4×7 medication organizer tray apparatus 100 contains medications 112 that are to be taken at noon time, every day of the week. The third row of the 4×7 medication organizer tray apparatus 100 contains medications 112 that are to be taken in the evening, every day of the week. The fourth row is not filled and is empty.

Figure 19C:
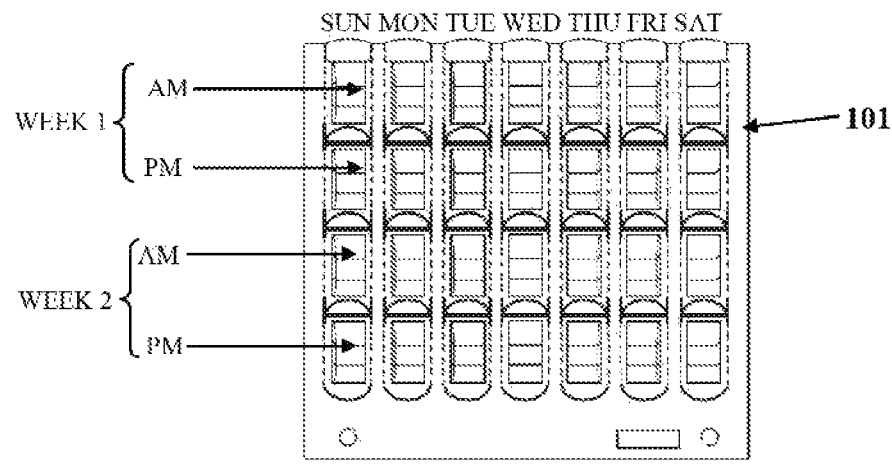

FIG. 19C exemplarily illustrates a 4×7 medication organizer tray apparatus 100 containing a medication dosage for two weeks. The first row of the 4×7 medication organizer tray apparatus 100 contains medications 112 that are to be taken in the morning, every day of week 1. The second row of the 4×7 medication organizer tray apparatus 100 contains medications 112 that are to be taken in the evening, every day of week 1. The third row of the 4×7 medication organizer tray apparatus 100 contains medications 112 that are to be taken in the morning, every day of week 2. The fourth row of the 4×7 medication organizer tray apparatus 100 contains medications 112 that are to be taken in the evening, every day of week 2.

Figure 19D:
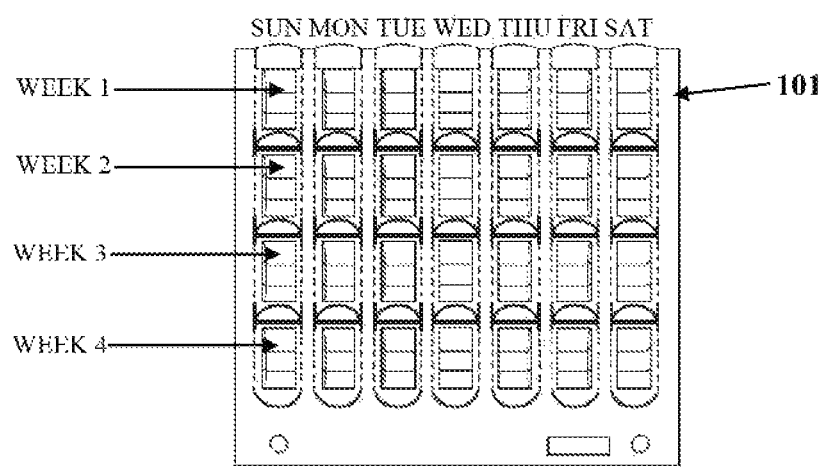

FIG. 19D exemplarily illustrates a 4×7 medication organizer tray apparatus 100 containing a medication dosage for a month or for 4 weeks. The first row of the 4×7 medication organizer tray apparatus 100 contains medications 112 that are to be taken every day of week 1, once a day. The second row of the 4×7 medication organizer tray apparatus 100 contains medications 112 that are to be taken every day of week 2, once a day. The third row of the 4×7 medication organizer tray apparatus 100 contains medications 112 that are to be taken every day of week 3, once a day. The fourth row of the 4×7 medication organizer tray apparatus 100 contains medications 112 that are to be taken every day of week 4, once a day.

Figure 20A:
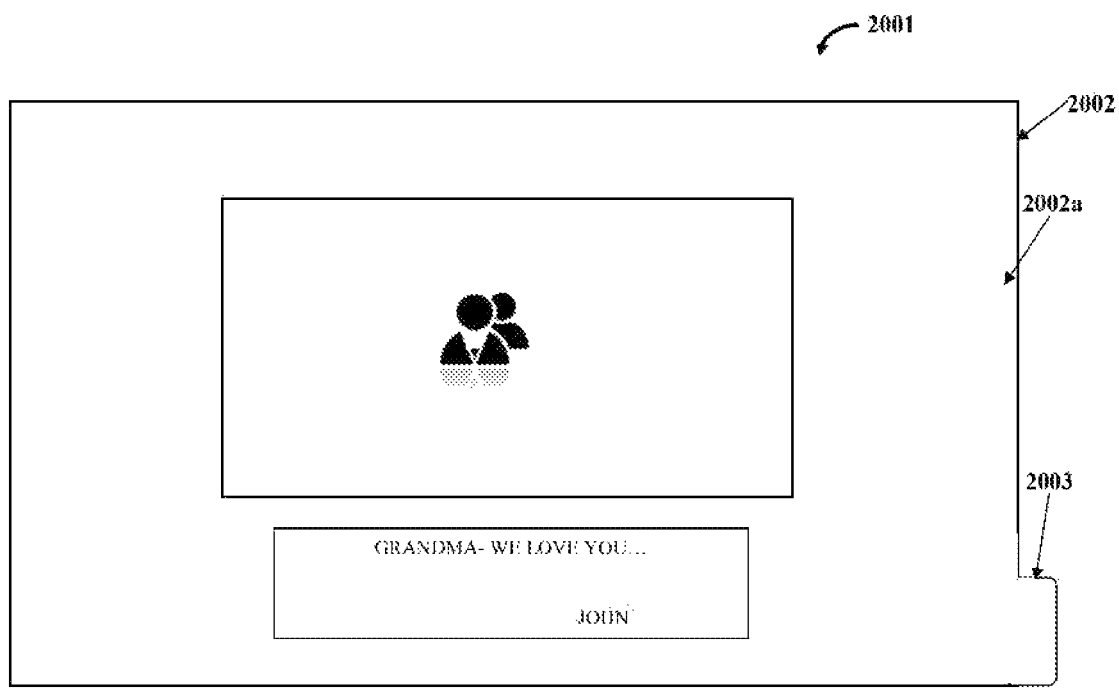
FIGS. 20A-20B exemplarily illustrate different views of a cover jacket configured to cover and accommodate the medication organizer tray apparatus.
Figure 20B:
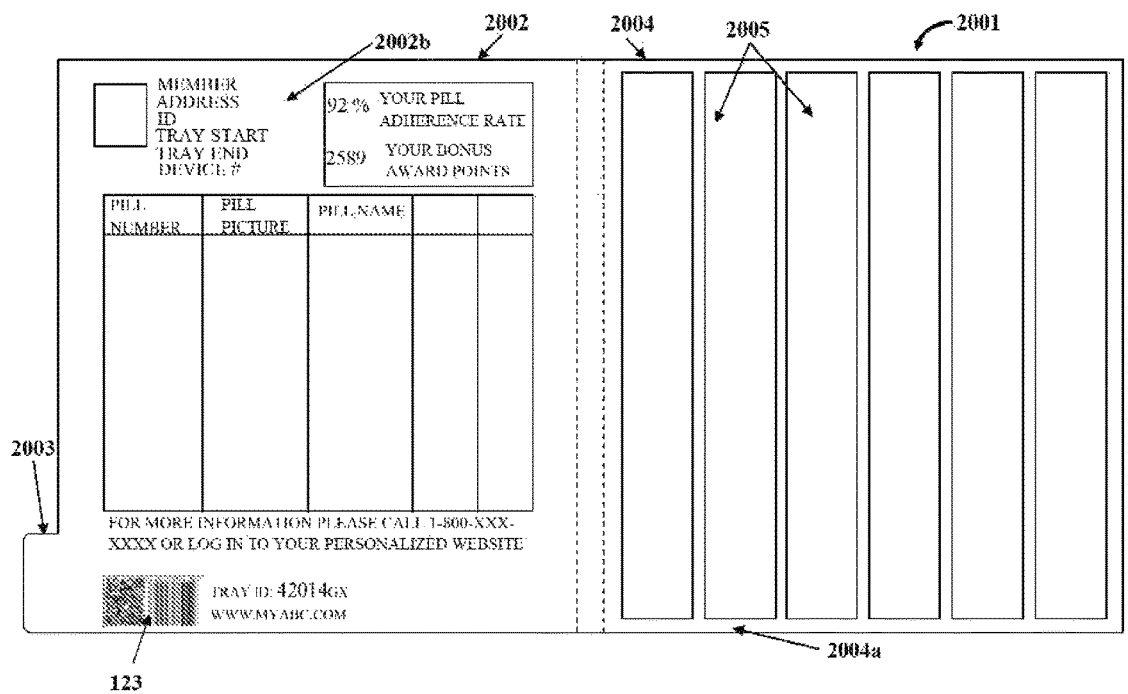
Figure 20C:
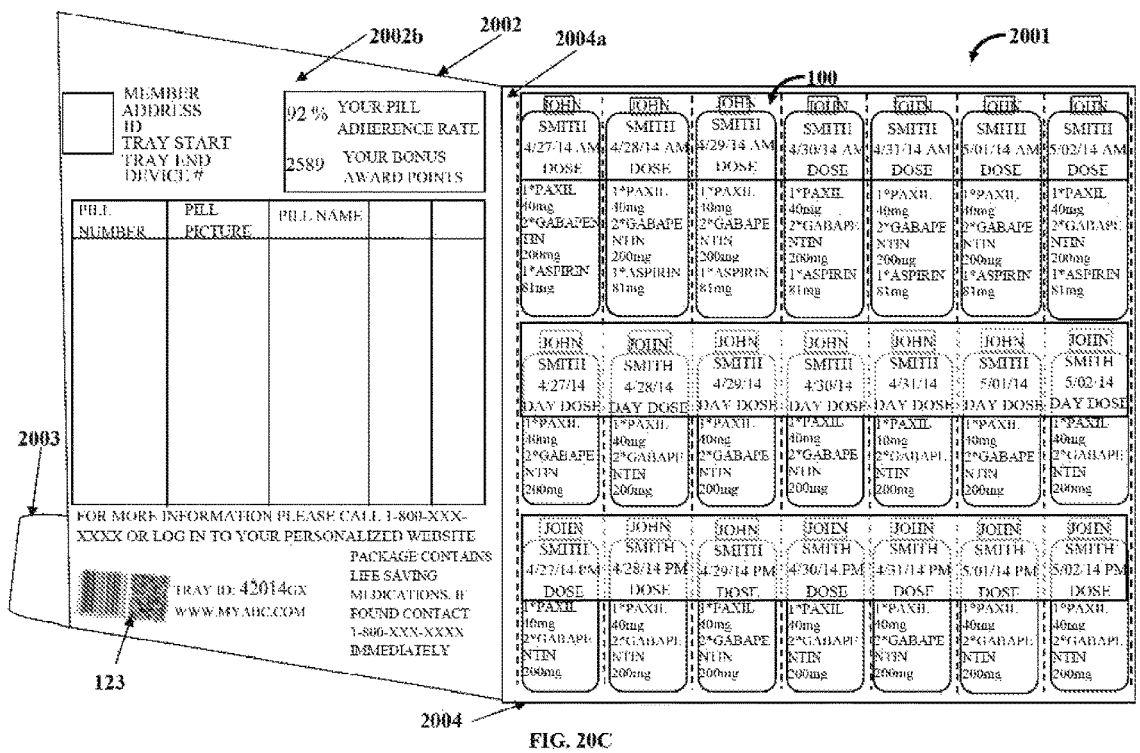
FIG. 20C exemplarily illustrates the medication organizer tray apparatus accommodated within the cover jacket.

FIGS. 20A-20B exemplarily illustrate different views of a cover jacket 2001 configured to cover and accommodate the medication organizer tray apparatus 100 exemplarily illustrated in FIG. 20C. The cover jacket 2001 securely accommodates the medication organizer tray apparatus 100, thereby facilitating easy transportation and storage of the medication organizer tray apparatus 100. FIG. 20C exemplarily illustrates the medication organizer tray apparatus 100 accommodated within the cover jacket 2001. In an embodiment, the cover jacket 2001 is configured as a foldable jacket comprising a top panel 2002 exemplarily illustrated in FIGS. 20A-20C, and a bottom panel 2004 exemplarily illustrated in FIGS. 20B-20C. FIG. 20A exemplarily illustrates a top plan view of the cover jacket 2001, showing a front surface 2002a of the top panel 2002 of the cover jacket 2001. In an embodiment, the front surface 2002a of the top panel 2002 comprises information specific to a healthcare recipient comprising, for example, personalized images, personalized messages, a company name, healthcare recipient information, etc., printed thereon as exemplarily illustrated in FIG. 20A. The top panel 2002 comprises a tab 2003 for opening the cover jacket 2001 as exemplarily illustrated in FIGS. 20B-20C.

FIGS. 20B-20C exemplarily illustrate top perspective views of the cover jacket 2001, showing the top panel 2002 and the bottom panel 2004 of the cover jacket 2001. In an embodiment, a rear surface 2002b of the top panel 2002 comprises, for example, information specific to medications 112 contained in each medication bin 102 of the medication organizer tray apparatus 100, information specific to a patient to whom the medication organizer tray apparatus 100 is prescribed, incentives for medication adherence, status of incentives such as reward points status, the identifier code 123 of the medication organizer tray apparatus 100, etc. In an embodiment, the bottom panel 2004 of the cover jacket 2001 comprises multiple slots 2005 that allow insertion of the medication bins 102 of the medication organizer tray apparatus 100 through the slots 2005. The medication organizer tray apparatus 100 is removably attached to a front surface 2004a of the bottom panel 2004 and the medication bins 102 of the medication organizer tray apparatus 100 are inserted through the slots 2005 of the bottom panel 2004. When a healthcare recipient receives the medication organizer tray apparatus 100 in the cover jacket 2001 from a pharmacy, he/she places the medication organizer tray apparatus 100 together with the cover jacket 2001 into the receptacle base 2101 exemplarily illustrated in FIGS. 21A-21B and FIG. 22. In an embodiment, the cover jacket 2001 is removed prior to placing the medication organizer tray apparatus 100 into the receptacle base 2101.

FIGS. 21A-21B exemplarily illustrate different views showing the medication organizer tray apparatus 100 inserted into the receptacle base 2101. FIG. 21A exemplarily illustrates a perspective view of the medication organizer tray apparatus 100 inserted into the receptacle base 2101. FIG. 21B exemplarily illustrates a side perspective view of the medication organizer tray apparatus 100 inserted into the receptacle base 2101. The receptacle base 2101 is a base that holds the medication organizer tray apparatus 100 with prefilled medications 112 exemplarily illustrated in FIG. 1B. In an embodiment, the receptacle base 2101 comprises a receptacle 2105, a loudspeaker 2102, a liquid crystal display (LCD) screen 2103, and a call button 2104. The medication organizer tray apparatus 100 is inserted into the receptacle 2105 of the receptacle base 2101. The receptacle base 2101 plays personalized audio messages such as "grandma thank you for taking your medication" or chimes to communicate or talk to healthcare recipients via the loudspeaker 2102, and displays personalized text messages, adherence status, a clock interface that displays time, etc., on the LCD screen 2103. In an embodiment, the loudspeaker 2102 vocalizes a serial identifier that matches a healthcare recipient identifier. Furthermore, when the medication organizer tray apparatus 100 is inserted into the receptacle base 2101, the receptacle base 2101 extracts messages and other medication adherence information from the electronic identification component 103 and annunciates the messages at the right dose and alarm time and other times as programmed via the loudspeaker 2102. In an embodiment, the LCD screen 2103 displays a serial identifier that matches a healthcare recipient identifier. The call button 2104 of the receptacle base 2101 allows a healthcare recipient to call or connect with a healthcare provider or an advisor. The healthcare provider or the advisor responds, when the call button 2104 is pressed by the healthcare recipient. The receptacle base 2101 further comprises adherence indicators 2106 that are configured to indicate behavior of healthcare recipients based on medication adherence. The adherence indicators 2106 change colors based on medication adherence of the healthcare recipients. The receptacle base 2101 further comprises additional buttons 2107 to allow the healthcare recipients to communicate with the healthcare provider or select options. The additional buttons 2107 comprise, for example, an "up" button 2107a, a "down" button 2107b, and a "select" button 2107c as exemplarily illustrated in FIG. 21A. In an embodiment, the receptacle base 2101 allows connection, for example, to a user device 2503 exemplarily illustrated in FIG. 25, for example, a cell phone, a smartphone, etc., via universal serial bus (USB) ports 2108. The USB ports 2108 are spaced appropriately to hold, for example, two dongles at one time.

In an embodiment, the receptacle base 2101 comprises a lid 2109 with sensor bars, hereinafter referred to as "clamp bars" 2110, as exemplarily illustrated in FIG. 21B, for keeping the medication organizer tray apparatus 100 from flapping and ensuring a strong electrical connection between the medication organizer tray apparatus 100 and the receptacle base 2101, when closed. In an embodiment, the receptacle base 2101 comprises, for example, 8 clamp bars 2110. The lid 2109 with the clamp bars 2110 is pushed down by a healthcare recipient or a healthcare provider after placing the medication organizer tray apparatus 100 in the receptacle base 2101, leaving the medication bins 102 exemplarily illustrated in FIG. 21B, exposed through the clamp bars 2110. In an embodiment, a diffused material 130 is deposited on a cut 129 configured on each medication bin 102 as exemplarily illustrated in FIG. 21B. The diffused material 130 indicates one or more dosage times of the medications 112 in each medication bin 102 and/or a message specific to each medication bin 102. In an embodiment, the diffused material 130 configured as a blinking light on the medication bin 102 can indicate that there is a message for that specific medication bin 102, for example, a message indicating medications 112 in that medication bin 102 have changed, a message indicating not to take the medications 112 as that dose period has expired, some specific instructions on how to take the medications 112, etc. The raised bump front edge 115 of each of the medication bins 102 is lit using the diffused material 130 configured as a diffused light source deposited on the raised bump front edge 115 of each of the medication bins 102 as exemplarily illustrated in FIG. 21B. The lit raised bump front edge 115 of a medication bin 102 shows the healthcare recipient which raised bump front edge 115 of a medication bin 102 needs to be raised and hence which medication bin 102 needs to be opened. This lighting arrangement of the medication organizer tray apparatus 100 assists healthcare recipients with dementia and forgetfulness who may have difficulty in remembering, for example, a day, a date, or a time of consuming the medications 112 and need to be directed to remove a correct medication bin 102. In an embodiment, for proper adhesive application of the bin cover layer 104 on the medication bins 102 of the medication organizer tray apparatus 100 as exemplarily illustrated in FIGS. 2A-2B, at the pharmacy, or for stacking for storage before shipment, or transport of the medication organizer tray apparatus 100, the medication bins 102 are configured without the raised bump front edges 115. In this embodiment, the raised bump front edges 115 of the medication bins 102 are raised at the time of inserting the medication organizer tray apparatus 100 into the receptacle base 2101.

FIG. 22 exemplarily illustrates a top plan view of an embodiment of the receptacle base 2101 accommodating the medication organizer tray apparatus 100. The receptacle base 2101 disclosed herein comprises a loudspeaker 2102, a liquid crystal display (LCD) screen 2103, and a call button 2104. The receptacle base 2101 plays audio messages via the loudspeaker 2102 and displays text messages and adherence status on the LCD screen 2103. The call button 2104 of the receptacle base 2101 allows a healthcare recipient to call a healthcare provider. The receptacle base 2101 further comprises additional buttons, for example, an "up" button 2107a and a "down" button 2107b to allow the healthcare recipients to select options.

Figure 23:
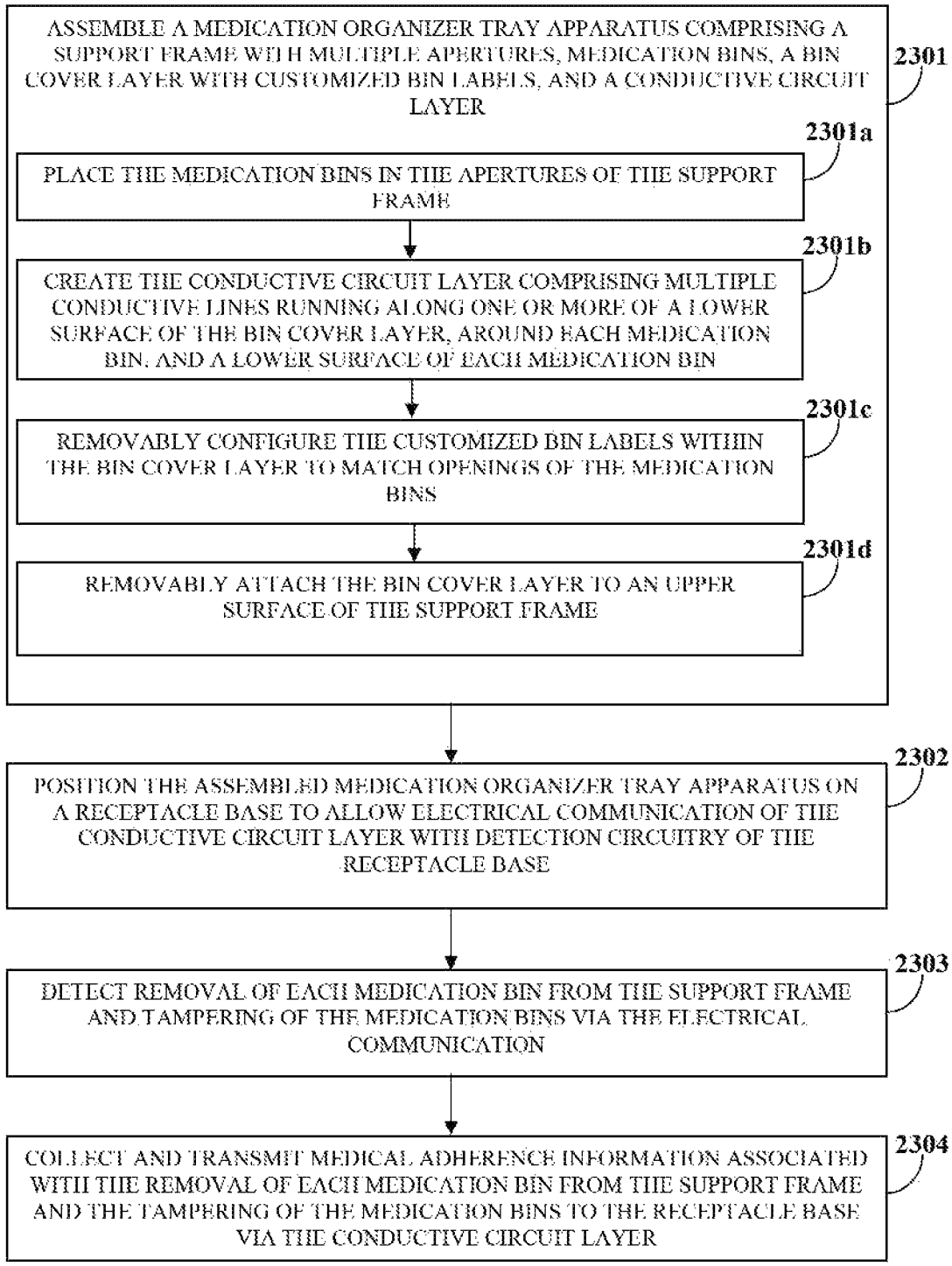
FIG. 23 illustrates a method for organizing medications and collecting medication adherence information.

FIG. 23 illustrates a method for organizing medications 112 exemplarily illustrated in FIG. 1B, FIG. 9, and FIGS. 11A-11B, and collecting medication adherence information. The method disclosed herein comprises assembling 2301 the medication organizer tray apparatus 100 comprising the support frame 101 with multiple apertures 111 positioned at predefined intervals from each other, multiple medication bins 102, the bin cover layer 104 with multiple customized bin labels 106, and the conductive circuit layer 107, as exemplarily illustrated and disclosed in the detailed description of FIGS. 1A-1C. The medication bins 102 are placed 2301a in the apertures 111 of the support frame 101. The medication bins 102 accommodate multiple medications 112. In an embodiment, a medication dispensing system 2401 exemplarily illustrated in FIG. 24 captures an image of an upper surface 101a and a lower surface 101b of the support frame 101 of the medication organizer tray apparatus 100 exemplarily illustrated in FIGS. 1A-1B, post filling of the medication organizer tray apparatus 100 with the medications 112. The images are captured before removably attaching the bin cover layer 104 to the upper surface 101a of the support frame 101. The conductive circuit layer 107 comprising multiple conductive lines 108 running along one or more of the lower surface 104b of the bin cover layer 104, around each medication bin 102, and the lower surface 102a of each medication bin 102 is created 2301b. The customized bin labels 106 exemplarily illustrated in FIG. 1A, FIGS. 2A-2B, FIGS. 8-9, and FIGS. 14A-14D, are removably configured 2301c within the bin cover layer 104 to match openings 117 of the medication bins 102 exemplarily illustrated in FIG. 7, FIG. 10, and FIG. 18B. The customized bin labels 106 comprise medical information printed thereon. The bin cover layer 104 is removably attached 2301d to the upper surface 101a of the support frame 101. The customized bin labels 106 of the bin cover layer 104 affixed to the upper surface 101a of the support frame 101 seals the openings 117 of the medication bins 102.

The assembled medication organizer tray apparatus 100 is positioned 2302 on the receptacle base 2101 exemplarily illustrated in FIGS. 21A-21B and FIG. 22 to allow electrical communication of the conductive circuit layer 107 of the assembled medication organizer tray apparatus 100 with the detection circuitry 1601 of the receptacle base 2101 exemplarily illustrated in FIG. 16C. Removal of each medication bin 102 from the support frame 101 and tampering of the medication bins 102 are detected 2303 via the electrical communication between the conductive circuit layer 107 of the assembled medication organizer tray apparatus 100 and the detection circuitry 1601 of the receptacle base 2101. In an embodiment, a power source (not shown) is electrically connected to the conductive circuit layer 107 of the assembled medication organizer tray apparatus 100. In an embodiment, the power source supplies minimal power at predetermined time intervals to the conductive circuit layer 107 to enable detection of a break in the conductive circuit layer 107 in electric communication with the receptacle base 2101, when one or more of the medication bins 102 are removed from the support frame 101. In another embodiment, the power source supplies a constant power supply of a minimal magnitude to the conductive circuit layer 107 to enable detection of a break in the conductive circuit layer 107 in electric communication with the receptacle base 2101, when one or more of the medication bins 102 are removed from the support frame 101.

The assembled medication organizer tray apparatus 100 collects and transmits 2304 the medication adherence information associated with the removal of each medication bin 102 from the support frame 101 and the tampering of the medication bins 102, to the receptacle base 2101 via the conductive circuit layer 107. The medication adherence information indicates, for example, which of the medication bins 102 is removed from the support frame 101 for ensuring medication adherence by a healthcare recipient and verifying the presence of medications 112 in each medication bin 102. The electronic identification component 103 exemplarily illustrated in FIGS. 17A-17B, is embedded into the support frame 101 during assembly of the medication organizer tray apparatus 100. The electronic identification component 103 is configured to electrically communicate with the receptacle base 2101. The electronic identification component 103 identifies the medication organizer tray apparatus 100 for verifying the presence of medications 112 in each medication bin 102, and stores and exchanges the medication adherence information with the receptacle base 2101.

Figure 24:
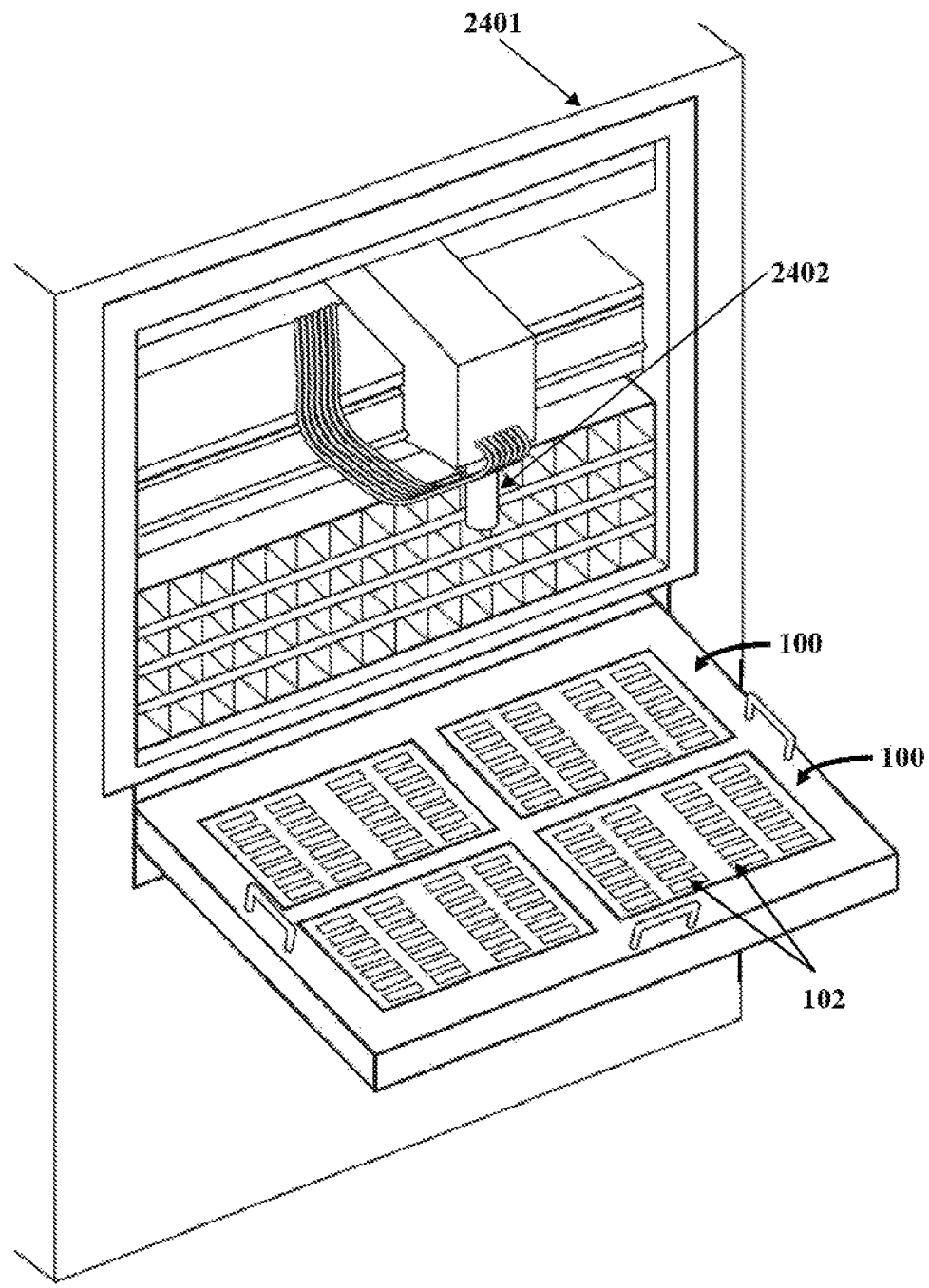
FIG. 24 exemplarily illustrates a side perspective view of a medication dispensing system for filling the medication organizer tray apparatus with medications.

FIG. 24 exemplarily illustrates a side perspective view of a medication dispensing system 2401 for filling the medication organizer tray apparatus 100 with medications 112 exemplarily illustrated in FIG. 1B. Multiple medication bins 102 of different shapes or sizes accommodate medications 112 of different types, for example, parenterals, oral medications, blister packed medications, etc., in the medication organizer tray apparatus 100 as disclosed in the detailed description of FIGS. 1A-IC and FIG. 6. In an embodiment, up to 8 medication organizer tray apparatuses 100 can be placed in the medication dispensing system 2401. The medication dispensing system 2401 fills medications 112 into the medication organizer tray apparatus 100 using a manual dispenser or a robotic dispenser 2402 as exemplarily illustrated in FIG. 24. In an embodiment, the medication dispensing system 2401 captures an image of the medication organizer tray apparatus 100 after the filling process is complete. Once the filling is complete, each medication organizer tray apparatus 100 is manually removed, checked, and sealed with the bin cover layer 104 configured with the customized bin labels 106 exemplarily illustrated in FIG. 1A. FIGS. 2A-2B, FIGS. 8-9, and FIGS. 14A-14D, and the other component layers, for example, 303, 304, 305, 307, 308, 309, etc., exemplarily illustrated in FIG. 3, of the medication organizer tray apparatus 100 by a pharmacist or a pharmacy technician.

FIG. 25 exemplarily illustrates communication between the medication organizer tray apparatus 100 inserted in the receptacle base 2101, and a backend server 2502 and a user device 2503 via a network 2501. The user device 2503 is an electronic device, for example, a personal computer, a tablet computing device, a mobile computer, a mobile phone, a smartphone, a portable computing device, a laptop, a touch centric device, a workstation, a portable electronic device, a network enabled computing device, an interactive network enabled communication device, any other suitable computing equipment, and combinations of multiple pieces of computing equipment, etc. Computing equipment, for example, one or more servers may be associated with one or more online services. The network 2501 is, for example, the internet, an intranet, a wired network, a wireless network, a communication network that implements Bluetooth® of Bluetooth Sig, Inc., a network that implements Wi-Fi® of Wi-Fi Alliance Corporation, an ultra-wideband communication network (UWB), a wireless universal serial bus (USB) communication network, a communication network that implements ZigBee® of ZigBee Alliance Corporation, a general packet radio service (GPRS) network, a mobile telecommunication network such as a global system for mobile (GSM) communications network, a code division multiple access (CDMA) network, a third generation (3G) mobile communication network, a fourth generation (4G) mobile communication network, a long-term evolution (LTE) mobile communication network, a public telephone network, etc., a local area network, a wide area network, an internet connection network, an infrared communication network, etc., or a network formed from any combination of these networks.

The conductive circuit layer 107 of the medication organizer tray apparatus 100 sends sensor signals that comprise medication adherence information to the detection circuitry 1601 of the receptacle base 2101 as exemplarily illustrated in FIGS. 16A-16C and as disclosed in the detailed description of FIGS. 16A-16C. The receptacle base 2101 then transmits the medication adherence information to the backend server 2502 via the network 2501. The backend server 2502 processes the medication adherence information and transmits the processed medication adherence information to the user device 2503 via the network 2501. In an embodiment, the backend server 2502 is implemented in a cloud computing environment. As used herein, "cloud computing environment" refers to a processing environment comprising configurable computing physical and logical resources, for example, networks, servers, storage, applications, services, etc., and data distributed over a network, for example, the internet. The cloud computing environment provides on-demand network access to a shared pool of the configurable computing physical and logical resources. The backend server 2502 is a cloud computing based platform implemented as a service for receiving medication adherence information collected from the medication organizer tray apparatus 100 and transmitting the received medication adherence information to the user device 2503 via the network 2501. The backend server 2502 is a cloud computing web based server developed, for example, using Microsoft .NET, the Oracles' database server, etc. In an embodiment, the backend server 2502 is hosted in a cloud computing environment, for example, at a customer premise, a company premise, a remote hosting center, etc.

A pill station manager application 2504 downloadable and executable on the user device 2503 displays the medication adherence information received from the backend server 2502 to the user device 2503 on a graphical user interface (GUI) 2601 exemplarily illustrated in FIG. 26, provided by the pill station manager application 2504. A user, for example, a healthcare recipient or a healthcare provider can view the medication adherence information on the GUI 2601 of the user device 2503. The user device 2503 comprises a non-transitory computer readable storage medium, for example, a memory unit configured to store computer program instructions defined by the pill station manager application 2504. As used herein, "non-transitory computer readable storage medium" refers to all computer readable media, for example, non-volatile media such as optical discs or magnetic disks, volatile media such as a register memory, a processor cache, etc., and transmission media such as wires that constitute a system bus coupled to the processor, except for a transitory, propagating signal. The user device 2503 further comprises at least one processor communicatively coupled to the non-transitory computer readable storage medium for executing the defined computer program instructions. The backend server 2502 transmits actionable information, for example, about the medications 112 exemplarily illustrated in FIG. 1B, wellness information, loyalty program information, surveys, etc., to the healthcare recipients who are using the medication organizer tray apparatus 100, via the network 2501.

FIG. 26 exemplarily illustrates a screenshot of an image of the medication organizer tray apparatus 100 exemplarily illustrated in FIGS. 1A-IC and FIGS. 2A-2B, filled with medications 112 exemplarily illustrated in FIG. 1B, displayed on the graphical user interface (GUI) 2601 provided by the pill station manager application 2504 on a user device 2503 exemplarily illustrated in FIG. 25. The pill station manager application 2504 stores images of the medication organizer tray apparatus 100 in a memory unit (not shown) of the user device 2503. At a pharmacy, when the medication organizer tray apparatus 100 is filled with medications 112, an image of the medication organizer tray apparatus 100 can be captured from different angles, for example, from the upper surface 101*a* and the lower surface 101*b* of the support frame 101 of the medication organizer tray apparatus 100 exemplarily illustrated in FIGS. 1A-1B, before placing the bin cover layer 104 exemplarily illustrated in FIG. 1A and FIGS. 2A-2B, on the upper surface 101*a* of the support frame 101. Imaging at different angles of the medication organizer tray apparatus 100 facilitates capturing of all the medications 112 in all the medication bins 102 of the medication organizer tray apparatus 100 exemplarily illustrated in FIGS. 1A-IC. In an embodiment, the receptacle base 2101 exemplarily illustrated in FIGS. 21A-21B and FIG. 22, comprises an embedded camera for capturing images of the medication organizer tray apparatus 100 from the lower surface 101*b* of the support frame 101 of the medication organizer tray apparatus 100. In this embodiment, the medication organizer tray apparatus 100 is then turned and placed face down using a temporary cover (not shown) to keep the medications 112 intact and in place during imaging of the upper surface 101*a* and the lower surface 101*b* of the support frame 101.

In another embodiment, a standard scanner is used to capture, store, and forward images to the pill station manager application 2504 for future reference. The pill station manager application 2504 displays clear views of the medication organizer tray apparatus 100 and provides enlarged views of each medication bin 102 for clarity on the GUI 2601 as exemplarily illustrated in FIG. 26. The pill station manager application 2504 further provides a detailed table providing a list of the different drugs or medications 112 in the medication organizer tray apparatus 100, compliance urgency of each of the medications 112, medication duration, dosage details, etc., on the GUI 2601. The pill station manager application 2504 also displays the latest medication images, for example, front images and back images of each of the medications 112 as exemplarily illustrated in FIG. 26, on the GUI 2601 for medication bin reconciliation.

The pill station manager application 2504 stores the captured images in the memory unit for record purposes or transmits the captured images to a remote pharmacist to confirm the right fill. Such remote checks allow robots, technicians, or a licensed pharmacist to fill the medication organizer tray apparatus 100 and get the fill approved and signed off as per standards rules and regulations. Once the medication organizer tray apparatus 100 is approved by the licensed pharmacist, the medication organizer tray apparatus 100 is shipped to the healthcare recipients. For example, the medication organizer tray apparatus 100 is filled in one place and approved by the local pharmacist to be sent to a healthcare recipient who lives in another state. The medication organizer tray apparatus 100 is sent to the healthcare recipient after verification and/or confirmation of a correct fill by a remote pharmacist of that state.

Each image of the medication organizer tray apparatus 100 that is taken is stored and shared with healthcare providers, for example, advisors through their respective user devices, for example, smartphones. The captured images can also be used by advisors or health care professionals to instruct healthcare recipients about their medications 112 and refer to the medications 112 by color, size, shape, etc., when guiding the healthcare recipients to remove a particular medication 112. In an embodiment, the image of the medication organizer tray apparatus 100 is also provided on a healthcare recipient portal and a healthcare provider portal for allowing the healthcare recipients, healthcare providers, home health staff, etc., to view the images. These images are also sent to healthcare recipients' phones, their computer, a care giver's phone, and other physicians to visually indicate what medications 112 have been loaded into the medication organizer tray apparatus 100. This image capture can be used to verify correct fill in incidences of incorrect filling reporting by healthcare recipients who may be abusing, diverting or hoarding the medications 112.

The computer programs that implement the methods and algorithms disclosed herein may be stored and transmitted using a variety of media, for example, the computer readable media in a number of manners. In an embodiment, hardwired circuitry or custom hardware may be used in place of, or in combination with, software instructions for implementation of the processes of various embodiments. Therefore, the embodiments are not limited to any specific combination of hardware and software. In general, the computer program codes comprising computer executable instructions may be implemented in any programming language. Various aspects of the method and apparatus disclosed herein may be implemented as programmed elements, or non-programmed elements, or any suitable combination thereof.

The present invention can be configured to work in a network environment comprising one or more computers that are in communication with one or more devices via a network. The computers may communicate with the devices directly or indirectly, via a wired medium or a wireless medium such as the Internet, a local area network (LAN), a wide area network (WAN) or the Ethernet, a token ring, or via any appropriate communications mediums or combination of communications mediums. Each of the devices comprises processors, some examples of which are disclosed above, that are adapted to communicate with the computers. In an embodiment, each of the computers is equipped with a network communication device, for example, a network interface card, a modem, or other network connection device suitable for connecting to a network. Each of the computers and the devices executes an operating system, some examples of which are disclosed above. While the operating system may differ depending on the type of computer, the operating system will continue to provide the appropriate communications protocols to establish communication links with the network. Any number and type of machines may be in communication with the computers.

The present invention is not limited to a particular computer system platform, processor, operating system, or network. One or more aspects of the present invention may be distributed among one or more computer systems, for example, servers configured to provide one or more services to one or more client computers, or to perform a complete task in a distributed system. For example, one or more aspects of the present invention may be performed on a client-server system that comprises components distributed among one or more server systems that perform multiple functions according to various embodiments. These components comprise, for example, executable, intermediate, or interpreted code, which communicate over a network using a communication protocol. The present invention is not limited to be executable on any particular system or group of systems, and is not limited to any particular distributed architecture, network, or communication protocol.

The foregoing examples have been provided merely for the purpose of explanation and are in no way to be construed as limiting of the present invention disclosed herein. While the invention has been described with reference to various embodiments, it is understood that the words, which have been used herein, are words of description and illustration, rather than words of limitation. Further, although the invention has been described herein with reference to particular means, materials, and embodiments, the invention is not intended to be limited to the particulars disclosed herein; rather, the invention extends to all functionally equivalent structures, methods and uses, such as are within the scope of the appended claims. Those skilled in the art, having the benefit of the teachings of this specification, may effect numerous modifications thereto and changes may be made without departing from the scope and spirit of the invention in its aspects.

We claim:

1. A medication organizer tray apparatus comprising:
a support frame comprising a plurality of apertures positioned at predefined intervals from each other;
a plurality of medication bins placed in said apertures of said support frame, said medication bins configured to accommodate a plurality of medications, said medication bins further configured to be removed from said support frame;
a bin cover layer removably attached to an upper surface of said support frame, said bin cover layer comprising a plurality of customized bin labels removably configured therewithin, said customized bin labels comprising medical information printed thereon and configured to seal openings of said medication bins; and
a conductive circuit layer comprising a plurality of conductive lines running along one or more of a lower surface of said bin cover layer, around each of said medication bins, and a lower surface of said each of said medication bins, wherein said conductive circuit layer is configured to electrically communicate with a receptacle base to enable detection of removal of said each of said medication bins from said support frame and detection of tampering of said medication bins.

2. The medication organizer tray apparatus of claim 1, further comprising an electronic identification component embedded into said support frame, wherein said electronic identification component is configured to electrically communicate with said receptacle base, and wherein said electronic identification component is further configured to identify said medication organizer tray apparatus, and store and exchange medication adherence information with said receptacle base.

3. The medication organizer tray apparatus of claim 2, wherein said medication adherence information stored in said electronic identification component comprises one or more of a serial identifier that matches a healthcare recipient identifier, information to coordinate medical activities, dosage times, wellness instructions for providing behavioral support for ensuring medication adherence by a healthcare recipient, time tagged messages, calendar information, and information associated with said removal of said each of said medication bins from said support frame and said tampering of said medication bins.

4. The medication organizer tray apparatus of claim 2, wherein said electronic identification component is embedded into said support frame via a sticker placed on said support frame, wherein said sticker comprises a conductive surface comprising conductive lines and conductive pads configured to electrically connect said electronic identification component to said receptacle base.

5. The medication organizer tray apparatus of claim 2, wherein said electronic identification component is one of an active chip and a passive chip and is configured to operate using one or more of wired modes of communication and wireless modes of communication.

6. The medication organizer tray apparatus of claim 1, wherein said support frame further comprises perforations positioned proximal to outer edges of said apertures of said support frame, wherein said perforations are configured to facilitate said removal of said medication bins from said support frame without damaging integrity of said support frame.

7. The medication organizer tray apparatus of claim 1, wherein said bin cover layer comprises perforations positioned at predefined areas on said bin cover layer to match perforations positioned proximal to outer edges of said apertures of said support frame.

8. The medication organizer tray apparatus of claim 1, wherein said each of said medication bins comprises perforated rims at upper edges of said each of said medication bins, wherein said perforated rims are configured to attach said each of said medication bins to perforations positioned proximal to outer edges of said apertures of said support frame.

9. The medication organizer tray apparatus of claim 1, wherein said bin cover layer is removably attached to said upper surface of said support frame using a selectively applied adhesive configured to match lips of said each of said medication bins and surfaces surrounding outer edges of said apertures of said support frame.

10. The medication organizer tray apparatus of claim 1, wherein said lower surface of said each of said medication bins is transparent for facilitating imaging of said medications accommodated in said each of said medication bins in said medication organizer tray apparatus.

11. The medication organizer tray apparatus of claim 1, wherein said each of said medication bins further comprises a lip extending around a periphery of an upper surface of said each of said medication bins, wherein said lip is configured to facilitate access to said each of said medication bins.

12. The medication organizer tray apparatus of claim 1, wherein said conductive circuit layer comprises a multi-layer conductive circuit configured to trip when one or more of said medication bins are removed from said support frame.

13. The medication organizer tray apparatus of claim 12, wherein said multi-layer conductive circuit comprises:
a conductive sensor circuit line for each of said medication bins, wherein said conductive sensor circuit line is configured to ensure connectivity of said each of said medication bins with said conductive circuit layer;
an edge conductive pad for said conductive sensor circuit line of said each of said medication bins, wherein said edge conductive pad is configured to electrically communicate with one or more base conductive pads of a receptacle base to enable detection of removal of said each of said medication bins from said support frame and detection of tampering of said medication bins; and
medication bin conductive pads configured for said each of said medication bins, wherein said medication bin conductive pads are configured to maintain conductive integrity of said conductive sensor circuit line of said each of said medication bins when perforations positioned at predefined areas on said bin cover layer cut through said conductive sensor circuit line.

14. The medication organizer tray apparatus of claim 13, wherein said multi-layer conductive circuit of said conductive circuit layer further comprises a common return line for one or more of said medication bins, wherein said common return line is configured to increase circuit reliability against incorrect registration of said conductive sensor circuit line for said each of said medication bins in said conductive circuit layer.

15. The medication organizer tray apparatus of claim 14, wherein said multi-layer conductive circuit of said conductive circuit layer further comprises a redundant circuit common return line, wherein said redundant circuit common return line is configured to ensure electrical conductivity in said conductive circuit layer if said common return line of said multi-layer conductive circuit is compromised.

16. The medication organizer tray apparatus of claim 15, wherein said multi-layer conductive circuit of said conductive circuit layer further comprises a redundant conductive pad for said redundant circuit common return line, wherein said redundant conductive pad is configured to connect to one or more base conductive pads of a receptacle base.

17. The medication organizer tray apparatus of claim 12, wherein said multi-layer conductive circuit of said conductive circuit layer further comprises conductive sensor circuit lines of a plurality of patterns for said one or more of said medication bins, wherein said conductive sensor circuit lines are configured to communicate with a receptacle base to detect tampering of said medication bins and said bin cover layer.

18. The medication organizer tray apparatus of claim 1, wherein said conductive lines of said conductive circuit layer running along said one or more of said lower surface of said bin cover layer, around said each of said medication bins, and said lower surface of said each of said medication bins are printed using one or more of a plurality of conductive print technologies to allow etching of electric circuits without causing short circuit issues.

19. The medication organizer tray apparatus of claim 1, wherein said conductive lines of said conductive circuit layer running along said one or more of said lower surface of said bin cover layer, around said each of said medication bins, and said lower surface of said each of said medication bins are created by selectively applying an electrically conductive material on said one or more of said lower surface of said bin cover layer, around said each of said medication bins, and said lower surface of said each of said medication bins, and removing excess of said electrically conductive material by one of an etching process and using chemicals.

20. The medication organizer tray apparatus of claim 1, wherein said medication bins are made of an electrically conductive material, wherein said medication bins are configured to communicate with said receptacle base for enabling said detection of said removal of said each of said medication bins from said support frame and said detection of said tampering of said medication bins.

21. The medication organizer tray apparatus of claim 1, further comprising electrically conductive material applied on perforations of said medication organizer tray apparatus for ensuring continuity around said perforations and connectivity with said conductive circuit layer.

22. The medication organizer tray apparatus of claim 1, further comprising a coated layer attached to said support frame, wherein said coated layer is configured to provide additional support to said support frame.

23. The medication organizer tray apparatus of claim 22, wherein said coated layer is configured to display supplementary information printed thereon, wherein said supplementary information comprises one or more of coupons, advertisements, incentives for medication adherence, status of incentives, appointments for a week, reminders, quotes, images, wellness information, wellness messages, gaming information, and quick reference telephone numbers of healthcare providers.

24. The medication organizer tray apparatus of claim 1, further comprising a diffused material deposited on a cut configured on said each of said medication bins, wherein said diffused material is configured to indicate one or more of dosage times of said medications in said each of said medication bins and a message specific to said each of said medication bins.

25. The medication organizer tray apparatus of claim 1, wherein said each of said medication bins is configured in one of a plurality of sizes and shapes to accommodate said medications of different types.

26. The medication organizer tray apparatus of claim 1, further comprising an identifier code printed on said bin cover layer, wherein said identifier code is configured to allow verification of presence of said each of said medication bins and said medications in said each of said medication bins.

27. The medication organizer tray apparatus of claim 26, wherein said identifier code is configured to be synchronized with a client application executable by at least one processor on a user device to confirm accuracy of alerts transmitted to a healthcare recipient.

28. The medication organizer tray apparatus of claim 1, wherein said each of said medication bins further comprises cut edges, bends, and raised bump front edges configured to facilitate said removal of said each of said medication bins from said support frame.

29. The medication organizer tray apparatus of claim 1, wherein said medical information printed on said customized bin labels comprises one or more of a list of said medications in said each of said medication bins, dosage information, color coding of dosage times, a time of day for administering said medications, drug names, directions to follow, name of a prescriber, date of preparation, description of contents of said each of said medication bins, a personalized website link configured to link to a secure online interface comprising healthcare recipient information, and a healthcare recipient identifier.

30. The medication organizer tray apparatus of claim 1, wherein said conductive circuit layer is electrically connected to a power source for receiving one of a constant power and a minimal power at predetermined time intervals to enable detection of a break in said conductive circuit layer, in electric communication with said receptacle base, when one or more of said medication bins are removed from said support frame.

* * * * *